(12) United States Patent
Mizuguchi et al.

(10) Patent No.: US 6,387,938 B1
(45) Date of Patent: May 14, 2002

(54) BENZIMIDAZOLE DERIVATIVES

(75) Inventors: Kiyoshi Mizuguchi; Nobuo Ohzawa, both of Tokyo; Yasuhiro Nakai, Shizuoka; Kazuyuki Matsuura, Tokyo; Shuhei Ohnishi, Tokyo; Yutaka Kato, Tokyo; Tsutomu Satoh, Tokyo, all of (JP)

(73) Assignee: Mochida Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/614,877

(22) Filed: Jul. 12, 2000

Related U.S. Application Data

(63) Continuation-in-part of application No. 09/214,274, filed as application No. PCT/JP99/22308 on Jul. 3, 1997, now abandoned.

(30) Foreign Application Priority Data

Jul. 5, 1996 (JP) .............................. 8-176711
Feb. 14, 2000 (JP) ....................... 2000-035283

(51) Int. Cl.$^7$ ................. A61K 31/4184; C07D 235/18; C07D 235/08
(52) U.S. Cl. ................. 514/394; 548/304.4; 548/306.1; 548/309.7; 548/310.1; 548/310.4; 548/310.7
(58) Field of Search ....................... 514/394; 548/304.4, 548/306.1, 309.7, 310.1, 310.4, 310.7

(56) References Cited

FOREIGN PATENT DOCUMENTS

| JP | 6165848 A | 4/1986 |
| JP | 3109378 A | 5/1991 |

*Primary Examiner*—Patricia L. Morris
(74) *Attorney, Agent, or Firm*—Birch, Stewart, Kolasch & Birch, LLP

(57) ABSTRACT

This invention provides novel benzimidazole derivatives represented by the formula (I); a process for producing the same; a drug containing at least one of such compounds as its active ingredient, in particular, a drug for preventing and/or treating diseases exhibiting eosinophilia, bronchial asthma and allergic diseases; and an enhancer for IFN-γ production, and in particular, an antitumor agent or an antiviral agent based on the action of enhancing the IFN-γ production which exhibits excellent oral bioavailability.

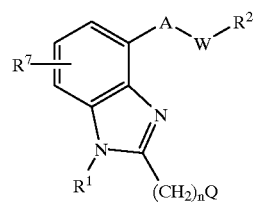

(I)

29 Claims, 8 Drawing Sheets

Ref. Ex. 1

Ref. Ex. 2

Ref. Ex. 3

Ref. Ex. 4

Ref. Ex. 5

Ref. Ex. 6

Ref. Ex. 7

Ref. Ex. 8

Ref. Ex. 9

Ref. Ex. 10

Ref. Ex. 11

Ref. Ex. 12

Ref. Ex. 13

Ref. Ex 14

Ref. Ex. 15

Ref. Ex 16

Ref. Ex. 17

Ref. Ex. 18

Ref. Ex. 19

Ref. Ex. 20

Ref. Ex. 21

Ref. Ex. 22

Ref. Ex. 23

Ref. Ex. 24

Ref. Ex. 25

Ref. Ex. 26

Ref. Ex. 27

Ref. Ex. 28

Ref. Ex. 29

Ref. Ex. 30

Ref. Ex. 31

Ref. Ex. 32

26

27

28

29

30

31

32

33

34

35

36

37

38

39

40

41

42

43

BENZIMIDAZOLE DERIVATIVES

CROSS REFERENCE TO RELATED APPLICATIONS

This application is a Continuation-In-Part of U.S. application Ser. No. 09/214,274, now abandoned, which is the national phase of PCT International Application No. PCT/JP97/02308 filed on Jul. 3, 1997, which designated the United States and on which priority is claimed under 35 USC §120, the entire contents of which are hereby incorporated by reference.

TECHNICAL FIELD

This invention relates to novel benzimidazole derivatives, and more specifically, 3-(2-(2-phenylethyl)benzimidazol-4-yl)-3-hydroxypropanoic acid and its esters, and compounds and optically active compounds thereof; a process for producing the same; drugs containing at least one of these compounds as the active ingredient, and in particular, a drug for preventing and/or treating diseases exhibiting eosinophilia, bronchial asthma or allergic diseases; otherwise an enhancer for interferon-γ production, and in particular, an antitumor agent or an antiviral agent based on the action of enhancing the production of the interferon-γ which is effective in oral administration.

BACKGROUND ART

A phenomenon in which eosinophils increase in blood or tissues, namely differentiating, Inducing or infiltrating phenomenon, is observed in many diseases. It is important from the clinical point of view to differentiate these diseases between certain diseases in which eosinophilia is frequently observed but its direct concern in pathophysiology is no and other diseases in which eosinophils are probably concerned as the main immune cell in the pathophysiology of such diseases. Addison disease, ulcerative colitis and the like diseases can be exemplified as diseases which correspond to the former case. Examples of the latter case include parasite infection, hypereosinophilic syndrome (HES), eosinophilic pneumonia, eosinophilic enterogastritis, bronchial asthma and the like diseases. Since eosinophils are closely related to the pathophysiology of bronchial asthma, so-called eosinophilic bronchitis is recently taking root as a pathophysiology concept. Particularly, there are some common points among movements of eosinophils which are concerned in these diseases. That is, they are summarized into three points of 1) acceleration of eosinophil production and differentiation by eosinophil growth lymphokines mainly including interleukin 5 (IL-5), 2) migration and accumulation of eosinophils into an involved organ by eosinophil chemotactic activity and 3) activation of eosinophils and prolongation of their life survival in the morbid sites. It is considered that the just described three factors or matters exert tissue damage and inflammation inducing actions of eosinophils in these diseases, thereby concerning in their pathophysiology, though there are differences in terms of foci and the degree of clinical symptoms. Also, though there are differences in terms of the increasing degree of eosinophils, atopic dermatitis, allergic rhinitis and the like various diseases can be exemplified as the diseases which exhibit eosinophilia (S. Nakajima and J. Shigehara, Meaning of the Clinical Diagnoses of eosinophils, "Eosinophils" ed. by S. Makino and K. Ishikawa, pp. 165–173, Kokusai Igaku Shuppan, 1991).

In consequence, a compound which controls eosinophils, or inhibits increment or activation of eosinophils in blood or tissues, could be applied to parasite infection, hypereosinophilic syndrome (HES), eosinophilic pneumonia, eosinophilic enterogastritis, bronchial asthma, atopic dermatitis, allergic rhinitis and the like diseases that exhibit eosinophilia.

Under the present situation, only the administration of steroid drugs is attempted as a symptomatic therapy for the treatment of diseases which exhibit eosinophilia, and there are no therapeutic methods which target eosinophils. It is extremely difficult to use steroid drugs, because they frequently cause peculiar side effects such as reduction of resistance against bacterial infection, hyperglycemia, diabetes, gastric ulcer, hyperkalemia, osteoporosis, obesity and the like, and their use is strictly stipulated such as prohibition of sudden termination of their administration. In addition, conventional asthma-treating drugs have been developed mainly based on histamine release inhibition action and the like, and it has been revealed that eosinophils are closely concerned also in this pathophysiology, so that the use of eosinophils as a target could be applied to certain types of asthma which cannot be treated by the conventional method. Under such situation, a compound which has high safety and can strongly control eosinophils seems to be markedly useful in a method of fundamental medical treatment of various diseases in which eosinophilia is concerned, so that realization of such a compound as a pharmaceutical preparation is strongly desired.

With regard to a compound of benzimidazole skeleton having a phenylethyl side chain on its partial structure, JP-A-3-109378 discloses that certain compounds having actions to inhibit both cyclooxygenase (CO) and lipoxygenase (LO) enzymes are useful in treating or alleviating allergic or inflammatory conditions, but it does not disclose their pharmacological data so that the strength of action of each compound and its detailed action mechanism are not clear (the term "JP-A" as used herein means an "unexamined published Japanese patent application"). Also, JP-A-61-65848 discloses a compound which selectively inhibits 5-lipoxygenase and discloses that it is effective in a rat adjuvant arthritis model and inhibits release of SRS-A in rat passive peritoneal anaphylaxis (PPA). However, these prior art benzimidazole derivatives are different from the compounds of the present invention in terms of their structures, and these patents do not disclose about the effect of these derivatives to inhibit increment or activation of eosinophils.

With regard to a compound of benzimidazole skeleton having a carboxylic acid or ester structure on its side chain, U.S. Pat. No. 5,216,003 discloses a compound which is useful as an NMDA antagonist in neurodegenerative diseases and neurotoxin disorders. Structure of this prior art benzimidazole derivative is also different from that of the compound of the present invention, and the patent does not disclose actions against eosinophils.

With regard to the compounds which enhance the production of interferon-γ (hereinafter abbreviated as IFN-γ), JP-A 10-251148 discloses that 1-(carbozole-4-iloxy)-3-[[2-(o-methoxyphenoxy)ethyl]amino]-2-propanol and the optically active compounds thereof which are the promoters of the IFN-γ production have the action of eliminating viral infection, and in particular, that such compounds are capable of reliably eliminating the cause of acute myocarditis associated with viral infection, and effectively treating the acute myocarditis. JP-A 8-143592 discloses that the peptides having the action of promoting the IFN-γ production promote cell propagation in the cell culture of normal mouse hepatic cell line (NCTC Clone 1469) and such peptides specifically promote the IFN-γ production of the cell in such cell culture. Furthermore, JP-A 4-208271 discloses that a promoter for the production of IFN-γ and the compound having the action of promoting interleukine-2 (hereinafter abbreviated as to as IL-2) are capable of producing IFN-γ and IL-2 from the monocyte of human peripheral blood, and such compounds are effective as a therapeutic agent for viral infection.

However, the compounds which promote the IFN-γ production as described above are different in their structure from the compounds of the present invention. In addition, in spite of the disclosure of promoting the cytokine production by directly stimulating the immunocompetent cell, there is no indication of providing the immunocompetent cell with the character of increased basal production rate of IFN-γ under stationary conditions without any immuno stimulation.

With regard to the benzimidazole derivatives, and in particular, 3-(2-(2-phenylethyl)benzimidazol-4-yl)-3-hydroxypropanoic acid and its esters, Kato et al. (The Journal of Immunology, vol.162, pages 7470–7479, 1999) reports that, when such compounds are orally administered and the splenocytes are cultured in the presence of an antigenic stimulant such as concanavalin A and ascarid extract, production of IL-4 and IL-5 is suppressed with simultaneous enhancement in the production of IFN-γ. However, there is no indication or teaching that such compound exhibits enhancement of the IFN-γ production of immunocompetent cells when such compound is orally administered to a tumor-bearing mouse.

In developing pharmaceutical preparations, it is important in general that these medicaments show excellent results not only in pharmacological tests but also in safety tests such as a subacute toxicological test (for example, a two week drug tolerance test in rats), a chronic toxicological test, a reproductive/developmental toxicological test, a mutagenicity test, an experimental carcinogenicity test, a metabolism test and the like. It is very important to provide a drug having excellent pharmakokinetics such as absence of cytochrome P450-related drug metabolism in the liver, serological or pathological abnormality and the like, namely a drug which has high safety, is effective in a small amount and can be handled easily. However, no compound has been disclosed in the prior art that resolves such problems while inhibiting the increment or activation of eosinophils, or the compound that resolves such problems while exhibiting the enhancement of the IFN-γ production.

In view of such situation, there is a strong desire of a drug which has oral bioavailability and high safety with no side effects and which can be handled with ease.

An object of the present invention is to provide compounds or a salt thereof which are effective against diseases exhibiting eosinophilia (parasite infection, hypereosinophilic syndrome (HES), eosinophilic pneumonia (PIE syndrome), eosinophilic enterogastritis, bronchial asthma, atopic dermatitis, allergic rhinitis and the like) or various allergic diseases (hay fever, pollinosis, allergic enterogastritis, food allergy, drug allergy and the like), through the regulation of eosinophils, namely inhibition of the increment or activation of eosinophils in blood or tissues, or through the inhibition of IgE antibody production; and compounds or a salt thereof which have the action of enhancing IFN-γ production and which is useful as an antitumor agent. A further object of the present invention is to provide benzimidazole derivatives, and in particular 3-(2-(2-phenylethyl)benzimidazol-4-yl)-3-hydroxypropanoic acid and its esters, optically active compounds thereof, and a salt thereof.

A still further object of the present invention is to provide a process for producing the compounds as described above, and drugs and pharmaceutical compositions containing the such compound, and in particular, a prophylactic and/or therapeutic agent for diseases exhibiting eosinophilia, bronchial asthma and allergic diseases, in which at least one of the aforementioned problems involved in the prior art is resolved; or an enhancer for IFN-γ production which exhibits oral bioavailability and excellent safety, and more specifically, an agent for enhancing IFN-γ production, and in particular, an antitumor agent or an antiviral agent containing a compound which exhibits the action of enhancing IFN-γ production in oral administration.

DISCLOSURE OF THE INVENTION

It is known that the number of eosinophils in blood or tissues increases in the case of parasite infection, hypereosinophilic syndrome (HES), eosinophilic pneumonia, eosinophilic enterogastritis, bronchial asthma, atopic dermatitis, allergic rhinitis and various other diseases in which eosinophils seem to be concerned in the pathophysiology of these diseases, and increment and activation of eosinophils are closely related to the worsening of such pathophysiology. In view of such situation, it is estimated that a compound which inhibits increment of eosinophils will be markedly useful in treating diseases in which eosinophils are closely taking part in their pathophysiology.

A compound which is capable of enhancing the IFN-γ production of splenocytes of a mammal including human by oral administration is also estimated to be useful as an antitumor agent or an antiviral agent.

Taking the aforementioned situation into consideration, the inventors of the present invention have conducted studies for many years on the screening of compounds capable of strongly inhibiting increment of eosinophils. As a result of such efforts, it has been found that a compound having a specific benzimidazole skeleton can inhibit increment of eosinophils strongly and has high safety with less side effects. The present invention has been completed on the bases of such finding.

The inventors of the present invention have also conducted an intensive study on the compounds having a specific benzimidazole skeleton and found that such compounds have the action of promoting the IFN-γ production of splenocytes of a mammal including human by oral administration. The present invention has also been completed on the bases of such finding.

A first aspect of the present invention is a compound represented by the following formula (I)

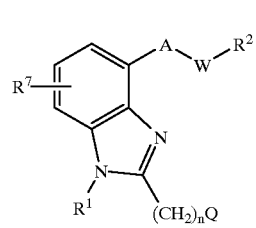

(I)

(wherein $R^1$ represents hydrogen atom or a straight- or branched-chain alkyl group having 1 to 4 carbon atoms, $R^2$ represents cyano group, hydroxymethyl group, 2-(2-imidazolyl)ethenyl group, a phenyl group substituted by one or two —COOR$^3$ groups, or a group —COOR$^3$ or —CONR$^4$R$^5$, R$^3$ represents hydrogen atom or a straight- or branched-chain alkyl group having 1 to 4 carbon atoms, each of $R^4$ and $R^5$ represents hydrogen atom, an alkyl group having 1 or 2 carbon atoms or a group —$CH_2COOR^6$ or —$CH(CH_2Ph)COOR^6$, wherein $R^4$ and $R^5$ may be the same or different from each other but, when one of $R^4$ and $R^5$ is a group —$CH_2COOR^6$ or —$CH(CH_2Ph)COOR^6$, the other one is hydrogen atom, A represents any one of groups selected from the class consisting of —CO—, —CH($OR^8$)—, —$CH_2O$—, —$CH(NHR^9)CH_2$—, —CH=CH— and —$CH_2CH_2$—, W represents a group —$CH_2$— or a single bond, Q represents a phenyl group which may be substituted by one hydroxyl group, n is from 0 to 2, $R^6$ represents a straight- or branched-chain alkyl group having 1 to 4 carbon atoms, $R^7$ represents hydrogen atom, hydroxyl group, a halogen atom or a straight- or branched-chain alkoxyl group having 1 to 4 carbon atoms, $R^8$ represents hydrogen atom or acetyl group and $R^9$ represents hydrogen atom, acetyl group, phenylsulfonyl group or a benzoyl group which may be substituted by one methoxy group) or a salt thereof or a medicament which contains the same as the active ingredient.

The following shows preferred substituent groups or preferred combinations thereof in the compound of the aforementioned formula (I), though the present invention is not restricted thereby. $R^1$ is preferably hydrogen atom. $R^2$ is preferably a phenyl group substituted by one or two —$COOR^3$ groups or a group —$COOR^3$ or —$CONR^4R^5$, more preferably a phenyl group substituted by one or two —$COOR^3$ groups or a group —$COOR^3$. $R^3$ is preferably a straight- or branched-chain alkyl group having 1 to 4 carbon atoms. A is preferably any one of —CO—, —CH($OR^8$)—, —$CH_2O$—. W is preferably a group —$CH_2$—. Q is preferably unsubstituted phenyl group. The symbol n is preferably 1 or 2, more preferably 2. $R^7$ is preferably hydrogen atom, a halogen atom or a straight- or branched-chain alkoxyl group having 1 to 4 carbon atoms.

In a preferred combination of the substituent groups, $R^1$ is hydrogen atom, W is a group —$CH_2$—, A is any one of groups selected from the class consisting of —CO—, —CH($OR^8$)— and —$CH_2O$— and $R^2$ is —$COOR^3$ or a phenyl group substituted by one or two — $COOR^3$ groups, and in a particularly preferred combination, $R^1$ is hydrogen atom, W is a group —$CH_2$— and the combination of A and $R^2$ is respectively a group —CO— or —CH($OR^8$)— and a group —$COOR^3$, or a group —$CH_2O$— and a phenyl group substituted by one or two —$COOR^3$ groups.

In a more preferable embodiment, the compound is a compound represented by the following formula (I)-v

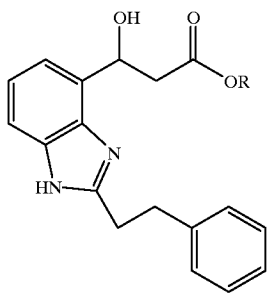
(I)-v (wherein R represents hydrogen atom or a lower alkyl groups) or a pharmaceutically acceptable salt thereof.

A second aspect of the present invention is an optically active compound represented by the following formula (I)-w

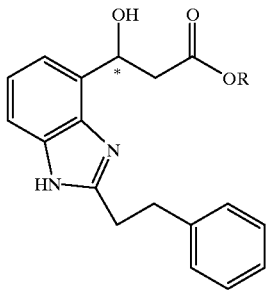
(I)-w (wherein R represents hydrogen atom or a lower alkyl group, and * is an asymmetric carbon atom) or a pharmaceutically acceptable salt thereof. In a more preferable embodiment, the compound is a (−) isomer.

A third aspect of the present invention is a process for producing the compound of formula (I) of claim 1 or a salt thereof, which comprises treating a compound represented by the following formula (III)

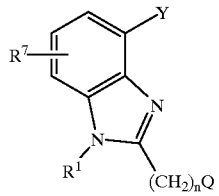
(III)

(wherein Y represents acetyl group, —$COOR^3$, a halogen atom, formyl group, chloroformyl group or bromoformyl group, $R^1$ and $R^3$ independently represents hydrogen atom or a straight- or branched-chain alkyl group having 1 to 4 carbon atoms, $R^7$ represents hydrogen atom, hydroxyl group, a halogen atom or a straight- or branched-chain alkoxyl group having 1 to 4 carbon atoms, Q represents a phenyl group which may be substituted by one hydroxyl group and n is from 0 to 2) or a salt thereof in accordance with any one of the steps selected from the group consisting of the following steps (a) to (k):

(a) the compound is allowed to react with carbon dioxide in the presence of an inorganic base or an organic base or with a carbamato complex in an inert solvent, thereby obtaining corresponding carboxylic acid derivatives, (b) the compound is allowed to react with halogenoformic acid ester, dialkyl carbonate, phosphonoformic acid ester or oxalic acid ester in the presence of a base, (c) the compound is allowed to react with malonic acid ester in the presence of a base, and then subjected to hydrolysis and subsequent decarboxylation, (d) an acetic acid or an acetic acid ester is prepared into a metal reagent using a metalating agent, and then the compound is allowed to react with the reagent, (e) a halogeno-acetic acid derivative is prepared into Reformatsky reagent, and then the compound is allowed to react with the reagent, (f) the compound is allowed to react with Meldrum's acid in the presence of a base to convert it into acyl Meldrum's acid which is then subjected to solvolysis and decarboxylation using an alcohol, ( g) the compound is allowed to react with a malonic acid ester, (h) using a transition metal complex, the compound is allowed to undergo cross-coupling reaction with an acetylene compound, and then hydration is carried out, (i) the compound is subjected to halogen-metal exchange reaction using an organic lithium reagent, allowed to react with ethylmalonyl chloride and then subjected to hydrolysis and decarboxylation, (j) the compound is reduced using a metal hydride, allowed to react with substituted benzyl halides in the presence of a base, (k) the compound is allowed to react with hydrogen cyanide or trimethylsilyl cyanide in the presence of a Lewis acid, and then hydrolyzed.

A fourth aspect of the present invention is a medicament, particularly a pharmaceutical composition, which contains at least one of the compounds represented by the formula (I) or a salt thereof as the active ingredient.

A fifth aspect of the present invention is agents for preventing and/or treating diseases exhibiting eosinophilia, which contains a compound represented by the formula (I) or a salt thereof as the active ingredient.

A sixth aspect of the present invention is agents for preventing and/or treating bronchial asthma, which contains a compound represented by the formula (I) or a salt thereof as the active ingredient.

A seventh aspect of the present invention is agents for preventing and/or treating allergic diseases, which contains a compound represented by the formula (I) or a salt thereof as the active ingredient.

In the specification of this invention, the term "diseases exhibiting eosinophilia" means diseases in which eosinophils seem to be concerned in the pathophysiology of these diseases such as parasite infection, hypereosinophilic syndrome (HES), eosinophilic pneumonia (PIE syndrome), eosinophilic enterogastritis, bronchial asthma, atopic dermatitis, allergic rhinitis, urticaria, hypersensitivity pneumonitis, pulmonary aspergillosis, eosinophilic leukemia and the like.

An eighth aspect of the present invention is an enhancer for interferon γ production containing at least one of the compounds represented by the formula (I) or a pharmaceutically acceptable salt thereof, and in particular, such an enhancer for oral administration.

A ninth aspect of the present invention is an enhancer for interferon γ production of an immunocompetent cell containing at least one of the compounds represented by the formula (I) or a pharmaceutically acceptable salt thereof, and in particular, such an enhancer for oral administration.

A tenth aspect of the present invention is an antitumor agent containing at least one of the compounds represented by the formula (I) or a pharmaceutically acceptable salt thereof, and in particular, such an antitumor agent for oral administration.

An eleventh aspect of the present invention is an antiviral agent containing at least one of the compounds represented by the formula (I) or a pharmaceutically acceptable salt thereof, and in particular, such an antiviral agent for oral administration.

According to further aspects of the present invention, there are provided a use of a substance containing at least one of the compounds represented by the formula (I) or a pharmaceutically acceptable salt thereof for a prophylactic/therapeutic agent for diseases exhibiting eosinophilia, a prophylactic/therapeutic agent for bronchial asthma, a prophylactic/therapeutic agent for allergic diseases, an enhancer for interferon γ production, an antitumor agent, or an antiviral agent; a method for preventing and/or treating diseases exhibiting eosinophilia, bronchial asthma, allergic diseases, tumor, or viral diseases comprising the step of administering a substance selected from the group consisting of the compounds represented by the formula (I), an optically active compound thereof, and a pharmaceutically acceptable salt thereof to a mammal including human.

BEST MODE OF CARRYING OUT THE INVENTION

Figure 1:
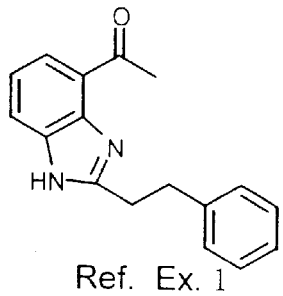
FIGS. 1 to 8 are drawings showing chemical structures of the benzimidazole derivatives produced in Reference Examples and Inventive Examples.
Figure 1:
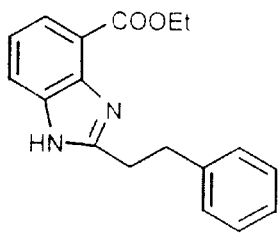
Figure 1:
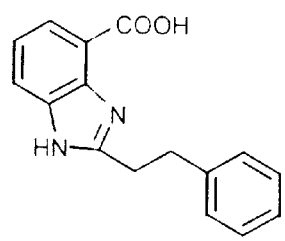
Figure 1:
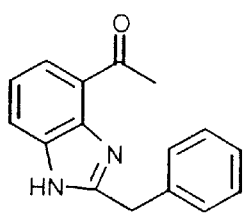
Figure 1:
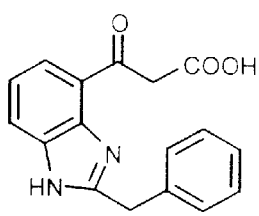
Figure 1:
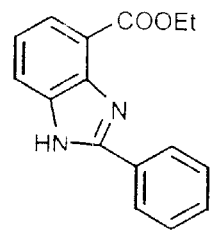
Figure 1:
Figure 1:
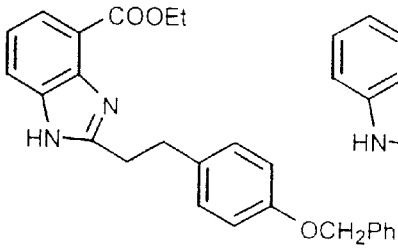
Figure 1:
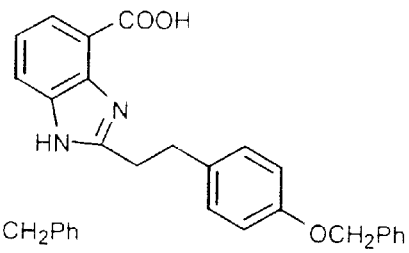
Figure 1:
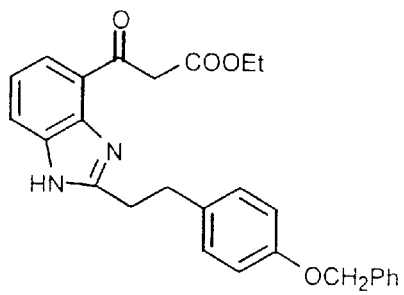
Figure 1:
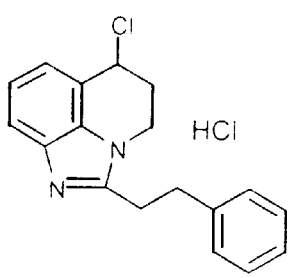
Figure 1:
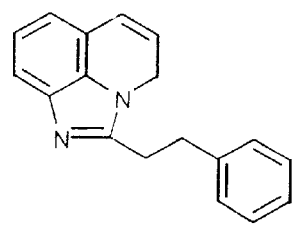

The following describes the present invention in detail.

The compound of the present invention is represented by the following formula (I).

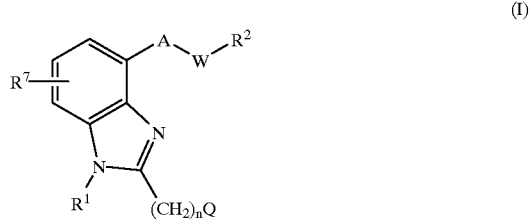

In the above formula, $R^1$ represents hydrogen atom or a straight- or branched-chain alkyl group having 1 to 4 carbon atoms. More illustratively, the straight- or branched-chain alkyl group having 1 to 4 carbon atoms means methyl group, ethyl group, n-propyl group, isopropyl group, n-butyl group, s-butyl group, isobutyl group, t-butyl group or the like. Preferably, $R^1$ is hydrogen atom or methyl group. More preferably, $R^1$ is hydrogen atom.

$R^2$ represents cyano group, hydroxymethyl group, 2-(2-imidazolyl)ethenyl group, a phenyl group substituted by one or two —$COOR^3$ groups, or a group —$COOR^3$ or —$CONR^4R^5$, $R^3$ represents hydrogen atom or a straight- or branched-chain alkyl group having 1 to 4 carbon atoms, each of $R^4$ and $R^5$ represents hydrogen atom, an alkyl group having 1 or 2 carbon atoms or a group —$CH_2COOR^6$ or —$CH(CH_2Ph)COOR^6$, wherein $R^4$ and $R^5$ may be the same or different from each other with the proviso that, when one of $R^4$ and $R^5$ is a group —$CH_2COOR^6$ or —$CH(CH_2Ph)COOR^6$, the other one is hydrogen atom, and $R^6$ represents a straight- or branched-chain alkyl group having 1 to 4 carbon atoms. More illustratively, the straight- or branched-chain alkyl group having 1 to 4 carbon atoms means methyl group, ethyl group, n-propyl group, isopropyl group, n-butyl group, s-butyl group, isobutyl group, t-butyl group or the like; the alkyl group having 1 or 2 carbon atoms means methyl group or ethyl group. Illustratively, the group —$COOR^3$ is carboxyl group, methoxycarbonyl group, ethoxycarbonyl group, n-propoxycarbonyl group, isopropoxycarbonyl group, n-butoxycarbonyl group, s-butoxycarbonyl group, isobutoxycarbonyl group or t-butoxycarbonyl group; the phenyl group substituted by one or two —$COOR^3$ groups is 2-carboxyphenyl group, 3-carboxyphenyl group, 4-carboxyphenyl group, 2,3-dicarboxyphenyl group, 2,4-dicarboxyphenyl group, 2,5-dicarboxyphenyl group, 2,6-dicarboxyphenyl group, 3,4-dicarboxyphenyl group, 2-methoxycarbonylphenyl group, 3-methoxycarbonylphenyl group, 4-methoxycarbonylphenyl group, 2,3-bis(methoxycarbonyl)

phenyl group, 2,4-bis(methoxycarbonyl)phenyl group, 2,5-bis(methoxycarbonyl)phenyl group, 2,6-bis(methoxycarbonyl)phenyl group, 3,4-bis(methoxycarbonyl)phenyl group, 2-ethoxycarbonylphenyl group, 3-ethoxycarbonylphenyl group, 4-ethoxycarbonylphenyl group, 2,3-bis(ethoxycarbonyl)phenyl group, 2,4-bis(ethoxycarbonyl)phenyl group, 2,5-bis(ethoxycarbonyl)phenyl group, 2,6-bis(ethoxy carbonyl)phenyl group, 3,4-bis(ethoxycarbonyl)phenyl group, 2-n-propoxycarbonylphenyl group, 3-n-propoxycarbonylphenyl group, 4-n-propoxycarbonylphenyl group, 2,3-bis(n-propoxycarbonyl)phenyl group, 2,4-bis(n-propoxycarbonyl)phenyl group, 2,5-bis(n-propoxycarbonyl)phenyl group, 2,6-bis(n-propoxycarbonyl)phenyl group, 3,4-bis(n-propoxycarbonyl)phenyl group, 2-isopropoxycarbonylphenyl group, 3-isopropoxycarbonylphenyl group, 4-isopropoxycarbonylphenyl group, 2,3-bis(isopropoxycarbonyl)phenyl group, 2,4-bis(isopropoxycarbonyl)phenyl group, 2,5-bis(isopropoxycarbonyl)phenyl group, 2,6-bis(isopropoxycarbonyl)phenyl group, 3,4-bis(isopropoxycarbonyl)phenyl group, 2-n-butoxycarbonylphenyl group, 3-n-butoxycarbonylphenyl group, 4-n-butoxycarbonylphenyl group, 2,3-bis(n-butoxycarbonyl)phenyl group, 2,4-bis(n-butoxycarbonyl)phenyl group, 2,5-bis(n-butoxycarbonyl)phenyl group, 2,6-bis(n-butoxycarbonyl)phenyl group, 3,4-bis(n-butoxycarbonyl)phenyl group, 2-s-butoxycarbonylphenyl group, 3-s-butoxycarbonylphenyl group, 4-s-butoxycarbonylphenyl group, 2,3-bis(s-butoxycarbonyl)phenyl group, 2,4-bis(s-butoxycarbonyl)phenyl group, 2,5-bis(s-butoxycarbonyl)phenyl group, 2,6-bis(s-butoxycarbonyl)phenyl group, 3,4-bis(s-butoxycarbonyl)phenyl group, 2-isobutoxycarbonylphenyl group, 3-isobutoxycarbonylphenyl group, 4-isobutoxycarbonylphenyl group, 2,3-bis(isobutoxycarbonyl)phenyl group, 2,4-bis(isobutoxycarbonyl)phenyl group, 2,5-bis(isobutoxycarbonyl)phenyl group, 2,6-bis(isobutoxycarbonyl)phenyl group, 3,4-bis(isobutoxycarbonyl)phenyl group, 2-t-butoxycarbonylphenyl group, 3-t-butoxycarbonylphenyl group, 4-t-butoxycarbonylphenyl group, 2,3-bis(t-butoxycarbonyl)phenyl group, 2,4-bis(tbutoxycarbonyl)phenyl group, 2,5-bis(t-butoxycarbonyl)phenyl group, 2,6-bis(t-butoxycarbonyl)phenyl group or 3,4-bis(tbutoxycarbonyl)phenyl group; and the group —CONR$^4$R$^5$ is carbamoyl group, N-methylcarbamoyl group, N-ethylcarbamoyl group, N,N-ethylmethylcarbamoyl group, N,N-diethylcarbamoyl group, N,N-dimethylcarbamoyl group, N-(methoxycarbonylmethyl)carbamoyl group, N-(ethoxycarbonylmethyl)carbamoyl group, N-(propoxycarbonylmethyl)carbamoyl group, N-(isopropoxycarbonylmethyl)carbamoyl group, N-(butoxycarbonylmethyl)carbamoyl group, N-(butoxycarbonylmethyl)carbamoyl group, N-(isobutoxycarbonylmethyl)carbamoyl group, N-(t-butoxycarbonylmethyl)carbamoyl group, N-(1-methoxycarbonyl-2-phenylethyl)carbamoyl group, N-(1-ethoxycarbonyl-2-phenylethyl)carbamoyl group, N-(1-propoxycarbonyl-2-phenylethyl)carbamoyl group, N-(1-isopropoxycarbonyl-2-phenylethyl)carbamoyl group, N-(1-butoxycarbonyl-2-phenylethyl)carbamoyl group, N-(1-s-butoxycarbonyl-2-phenylethyl)carbamoyl group, N-(1-isobutoxycarbonyl-2-phenylethyl)carbamoyl group or N-(1-t-butoxycarbonyl-2-phenylethyl)carbamoyl group.

Preferably, R$^2$ is a phenyl group substituted by one or two —COOR$^3$ groups or a group —COOR$^3$ or —CONR$^4$R$^5$, illustratively, the phenyl group substituted by one or two —COOR$^3$ groups is 2-carboxyphenyl group, 3-carboxyphenyl group, 4-carboxyphenyl group, 2,3-dicarboxyphenyl group, 2,4-dicarboxyphenyl group, 2,5-dicarboxyphenyl group, 2,6-dicarboxyphenyl group, 3,4-dicarboxyphenyl group, 2-methoxycarbonylphenyl group, 3-methoxycarbonylphenyl group, 4-methoxycarbonylphenyl group, 2,3-bis(methoxycarbonyl)phenyl group, 2,4-bis(methoxycarbonyl)phenyl group, 2,5-bis(methoxycarbonyl)phenyl group, 2,6-bis(methoxycarbonyl)phenyl group, 3,4-bis(methoxycarbonyl)phenyl group, 2-ethoxycarbonyl phenyl group, 3-ethoxycarbonylphenyl group, 4-ethoxycarbonylphenyl group, 2,3-bis(ethoxycarbonyl)phenyl group, 2,4-bis(ethoxycarbonyl)phenyl group, 2,5-bis(ethoxycarbonyl)phenyl group, 2,6-bis(ethoxycarbonyl)phenyl group, 3,4-bis(ethoxycarbonyl)phenyl group, 2-n-propoxycarbonylphenyl group, 3-n-propoxycarbonylphenyl group, 4-n-propoxycarbonylphenyl group, 2,3-bis(n-propoxycarbonyl)phenyl group, 2,4-bis(n-propoxycarbonyl)phenyl group, 2,5-bis(n-propoxycarbonyl)phenyl group, 2,6-bis(n-propoxycarbonyl)phenyl group, 3,4-bis(n-propoxycarbonyl)phenyl group, 2-isopropoxycarbonylphenyl group, 3-isopropoxycarbonylphenyl group, 4-isopropoxycarbonylphenyl group, 2,3-bis(isopropoxycarbonyl)phenyl group, 2,4-bis(isopropoxycarbonyl)phenyl group, 2,5-bis(isopropoxycarbonyl)phenyl group, 2,6-bis(isopropoxycarbonyl)phenyl group, 3,4-bis(isopropoxycarbonyl)phenyl group, 2-n-butoxycarbonylphenyl group, 3-n-butoxycarbonylphenyl group, 4-n-butoxycarbonylphenyl group, 2,3-bis(n-butoxycarbonyl)phenyl group, 2,4-bis(n-butoxycarbonyl)phenyl group, 2,5-bis(n-butoxycarbonyl)phenyl group, 2,6-bis(n-butoxycarbonyl)phenyl group, 3,4-bis(n-butoxycarbonyl)phenyl group, 2-s-butoxycarbonylphenyl group, 3-s-butoxycarbonylphenyl group, 4-s-butoxycarbonylphenyl group, 2,3-bis(s-butoxycarbonyl)phenyl group, 2,4-bis(s-butoxycarbonyl)phenyl group, 2,5-bis(s-butoxycarbonyl)phenyl group, 2,6-bis(s-butoxycarbonyl)phenyl group, 3,4-bis(s-butoxycarbonyl)phenyl group, 2-isobutoxycarbonylphenyl group, 3-isobutoxycarbonylphenyl group, 4-isobutoxycarbonylphenyl group, 2,3-bis(isobutoxycarbonyl)phenyl group, 2,4-bis(isobutoxycarbonyl)phenyl group, 2,5-bis(isobutoxycarbonyl)phenyl group, 2,6-bis(isobutoxycarbonyl)phenyl group, 3,4-bis(isobutoxycarbonyl)phenyl group, 2-t-butoxycarbonylphenyl group, 3-t-butoxycarbonylphenyl group, 4-t-butoxycarbonylphenyl group, 2,3-bis(t-butoxycarbonyl)phenyl group, 2,4-bis(tbutoxycarbonyl)phenyl group, 2,5-bis(t-butoxycarbonyl)phenyl group, 2,6-bis(t-butoxycarbonyl)phenyl group or 3,4-bis(t-butoxycarbonyl)phenyl group; the group —COOR$^3$ is carboxyl group, methoxycarbonyl group, ethoxycarbonyl group, n-propoxycarbonyl group, isopropoxycarbonyl group, n-butoxycarbonyl group, s-butoxycarbonyl group, isobutoxycarbonyl group or t-butoxycarbonyl group; and the group —CONR$^4$R$^5$ is carbamoyl group, N-methylcarbamoyl group, N-ethylcarbamoyl group, N,N-ethylmethylcarbamoyl group, N,N-diethylcarbamoyl group, N,N-dimethylcarbamoyl group, N-(methoxycarbonylmethyl)carbamoyl group, N-(ethoxycarbonylmethyl)carbamoyl group, N-(propoxycarbonylmethyl)carbamoyl group, N-(isopropoxycarbonylmethyl)carbamoyl group, N-(butoxycarbonylmethyl)carbamoyl group, N-(s-butoxycarbonylmethyl)carbamoyl group, N-(isobutoxycarbonylmethyl)carbamoyl group, N-(t-butoxycarbonylmethyl)carbamoyl group, N-(1-methoxycarbonyl-2-phenylethyl)carbamoyl group, N-(1-ethoxycarbonyl-2-phenylethyl)carbamoyl group, N-(1-propoxycarbonyl-2-phenylethyl)carbamoyl group, N-(1-isopropoxycarbonyl-2-phenylethyl)carbamoyl group, N-(1-butoxycarbonyl-2-phenylethyl)carbamoyl group, N-(-s-butoxycarbonyl-2-phenylethyl)carbamoyl group, N-(1-isobutoxycarbonyl-2-phenylethyl)carbamoyl group or N-(1-t-butoxycarbonyl-2-phenylethyl)carbamoyl group.

More preferably, $R^2$ is a phenyl group substituted by one or two —COOR$^3$ groups or a group —COOR$^3$, illustratively, the phenyl group substituted by one or two —COOR$^3$ groups is 2-carboxyphenyl group, 3-carboxyphenyl group, 4-carboxyphenyl group, 2,3-dicarboxyphenyl group, 2,4-dicarboxyphenyl group, 2,5-dicarboxyphenyl group, 2,6-dicarboxyphenyl group, 3,4-dicarboxyphenyl group, 2-methoxycarbonylphenyl group, 3-methoxycarbonylphenyl group, 4-methoxycarbonylphenyl group, 2,3-bis(methoxycarbonyl)phenyl group, 2,4-bis(methoxycarbonyl)phenyl group, 2,5-bis(methoxycarbonyl)phenyl group, 2,6-bis(methoxycarbonyl)phenyl group, 3,4-bis(methoxycarbonyl)phenyl group, 2-ethoxycarbonylphenyl group, 3-ethoxycarbonylphenyl group, 4-ethoxycarbonylphenyl group, 2,3-bis(ethoxycarbonyl)phenyl group, 2,4-bis(ethoxycarbonyl)phenyl group, 2,5-bis(ethoxycarbonyl)phenyl group, 2,6-bis(ethoxycarbonyl)phenyl group, 3,4-bis(ethoxycarbonyl)phenyl group, 2-n-propoxycarbonylphenyl group, 3-n-propoxycarbonylphenyl group, 4-n-propoxycarbonylphenyl group, 2,3-bis(n-propoxycarbonyl)phenyl group, 2,4-bis(n-propoxycarbonyl)phenyl group, 2,5-bis(n-propoxycarbonyl)phenyl group, 2,6-bis(n-propoxycarbonyl)phenyl group, 3,4-bis(n-propoxycarbonyl)phenyl group, 2-isopropoxycarbonylphenyl group, 3-isopropoxycarbonylphenyl group, 4-isopropoxycarbonylphenyl group, 2,3-bis(isopropoxycarbonyl)phenyl group, 2,4-bis(isopropoxycarbonyl)phenyl group, 2,5-bis(isopropoxycarbonyl)phenyl group, 2,6-bis(isopropoxycarbonyl)phenyl group, 3,4-bis(isopropoxycarbonyl)phenyl group, 2-n-butoxycarbonylphenyl group, 3-n-butoxycarbonylphenyl group, 4-n-butoxycarbonylphenyl group, 2,3-bis(n-butoxycarbonyl) phenyl group, 2,4-bis(n-butoxycarbonyl)phenyl group, 2,5-bis(n-butoxycarbonyl)phenyl group, 2,3-bis(n-butoxycarbonyl)phenyl group, 3,4-bis(n-butoxycarbonyl)phenyl group, 2-s-butoxycarbonylphenyl group, 3-s-butoxycarbonylphenyl group, 4-s-butoxycarbonylphenyl group, 2,3-bis(s-butoxycarbonyl)phenyl group, 2,4-bis(s-butoxycarbonyl)phenyl group, 2,5-bis(s-butoxycarbonyl)phenyl group, 2,6-bis(s-butoxycarbonyl)phenyl group, 3,4-bis(s-butoxycarbonyl)phenyl group, 2-isobutoxycarbonylphenyl group, 3-isobutoxycarbonylphenyl group, 4-isobutoxycarbonylphenyl group, 2,3-bis(isobutoxycarbonyl)phenyl group, 2,4-bis(isobutoxycarbonyl)phenyl group, 2,5-bis(isobutoxycarbonyl)phenyl group, 2,6-bis(isobutoxycarbonyl)phenyl group, 3,4-bis(isobutoxycarbonyl)phenyl group, 2-t-butoxycarbonylphenyl group, 3-t-butoxycarbonylphenyl group, 4-t-butoxycarbonylphenyl group, 2,3-bis(t-butoxycarbonyl)phenyl group, 2,4-bis(t-butoxycarbonyl)phenyl group, 2,5-bis(t-butoxycarbonyl)phenyl group, 2,6-bis(t-butoxycarbonyl)phenyl group or 3,4-bis(t-butoxycarbonyl)phenyl group; and the group —COOR$^3$ is carboxyl group, methoxycarbonyl group, ethoxycarbonyl group, n-propoxycarbonyl group, isopropoxycarbonyl group, n-butoxycarbonyl group, s-butoxycarbonyl group, isobutoxycarbonyl group or t-butoxycarbonyl group.

A represents any one of groups selected from the class consisting of —CO—, —CH(OR$^8$)—, —CH$_2$O—, —CH(NHR$^9$)CH$_2$—, —CH=CH— and —CH$_2$CH$_2$—, R$^8$ represents hydrogen atom or acetyl group and R$^9$ represents hydrogen atom, acetyl group, phenylsulfonyl group or a benzoyl group which may be substituted by one methoxy group. More illustratively, —CH(OR$^8$)— is —CH(OH)— or —CH(OCOCH$_3$)—, and —CH(NHR$^9$)CH$_2$— is —CH(NH$_2$)CH$_2$—, —CH(NHCOCH$_3$)CH$_2$—, —CH(NHSO$_2$Ph)CH$_2$—, —CH(NHCOPh)CH$_2$—, —CH(NHCO(2-OCH$_3$—C$_6$H$_4$)CH$_2$—, —CH(NHCO(3-OCH$_3$— C$_6$H$_4$)CH$_2$— or —CH(NHCO(4-OCH$_3$—C$_6$H$_4$)CH$_2$—.

Preferably, A is —CO—, —CH(OH)—, —CH(OCOCH$_3$)— or —CH$_2$O—.

W represents a group —CH$_2$— or a single bond. Preferably, W is a group —CH$_2$—.

Q represents a phenyl group which may be substituted by one hydroxyl group. More illustratively, the phenyl group which may be substituted by one hydroxyl group is unsubstituted phenyl group, 2-hydroxyphenyl group, 3-hydroxyphenyl group or 4-hydroxyphenyl group. Preferably, Q is unsubstituted phenyl group or 4-hydroxyphenyl group. More preferably, Q is unsubstituted phenyl group.

The numeral n is from 0 to 2. Preferably, n is 1 or 2, more preferably 2. In consequence, illustrative examples of —(CH$_2$)n-Q include unsubstituted phenyl group, 2-hydroxyphenyl group, 3-hydroxyphenyl group, 4-hydroxyphenyl group, unsubstituted benzyl group, 2-hydroxybenzyl group, 3-hydroxybenzyl group, 4-hydroxybenzyl group, unsubstituted phenylethyl group, 2-(2-hydroxyphenyl)ethyl group, 2-(3-hydroxyphenyl)ethyl group and 2-(4-hydroxyphenyl)ethyl group. Preferably, —(CH$_2$)n-Q is unsubstituted benzyl group, 2-hydroxybenzyl group, 3-hydroxybenzyl group, 4-hydroxybenzyl group, unsubstituted phenylethyl group, 2-(2-hydroxyphenyl)ethyl group, 2-(3-hydroxyphenyl)ethyl group or 2-(4-hydroxyphenyl)ethyl group. More preferably, —(CH$_2$)n-Q is unsubstituted phenylethyl group, 2-(2-hydroxyphenyl)ethyl group, 2-(3-hydroxyphenyl)ethyl group or 2-(4-hydroxyphenyl)ethyl group, and unsubstituted phenylethyl group is particularly preferred.

R$^7$ represents hydrogen atom, hydroxyl group, a halogen atom or a straight- or branched-chain alkoxyl group having 1 to 4 carbon atoms. More illustratively, the halogen atom is fluorine atom, chlorine atom, bromine atom or iodine atom, and the straight- or branched-chain alkoxyl group having 1 to 4 carbon atoms is methoxy group, ethoxy group, n-propoxy group, isopropoxy group, n-butoxy group, s-butoxy group, isobutoxy group, t-butoxy group or the like. Preferably, R$^7$ is hydrogen atom, fluorine atom, chlorine atom, bromine atom, iodine atom, methoxy group, ethoxy group, n-propoxy group, isopropoxy group, n-butoxy group, s-butoxy group, isobutoxy group or t-butoxy group. More preferably, R$^7$ is hydrogen atom.

In the aforementioned formula (I), preferred combination of —A—W— is CO—CH$_2$—, —CH(OH)—CH$_2$—, —CH(OCOCH$_3$)—CH$_2$— or —CH$_2$O—CH$_2$—.

Preferred combination of —A—W— and R$_2$ is one of the groups CO—CH$_2$—, —CH(OH)—CH$_2$— and —CH (OCOCH₃)—CH₂— and the group —COOR³, or the group —CH₂O—CH₂— and the phenyl group substituted by one or two —COOR³ groups.

In a preferred combination of the aforementioned substituent groups, R¹ is a hydrogen atom, W is group —CH₂—, A is any one of groups selected from the class consisting of —CO—, —CH(OR)— and —CH₂O—, and R² is —COOR³ or a phenyl group substituted by one or two —COOR³ groups, and in a particularly preferred combination, R¹ is hydrogen atom, W is the group —CH₂— and the combination of A and R² is the group —CO— or —CH(OR⁸)— and —COOR³ or the group —CH₂O— and the phenyl group substituted by one or two —COOR³ groups.

In a more preferable embodiment, the compound is a compound represented by the following formula (I)-v

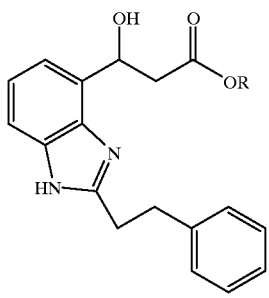

(I)-v (wherein R represents hydrogen atom or a lower alkyl groups) or a pharmaceutically acceptable salt thereof.

Unless otherwise noted, the term "lower" designates straight-chain or branched carbon chain containing 1 to 4 carbon atoms. Accordingly, "lower alkyl group or alkyl group containing 1 to 4 carbon atoms" include methyl, ethyl, propyl, isopropyl, butyl, isobutyl, sec-butyl, tert-butyl, and the like. When R is a lower alkyl group, R is preferably ethyl group.

Protecting groups of the compound of formula (I) can be introduced optionally during the reaction steps, and said protecting groups can be removed at the final step. Examples of the protecting group of hydroxyl group or carboxyl group include lower alkyl groups such as methyl group, ethyl group, t-butyl group, aralkyl groups such as benzyl group, 4-nitrobenzyl group, substituted silyl groups such as trimethylsilyl group, acyl groups such as acetyl group, benzoyl group, arylsulfonyl groups such as benzenesulfonyl group, tosyl group and methoxymethyl group, tetrahydropyranyl group and the like groups. Examples of the protecting group of NH group on the benzimidazole ring include benzyl group, p-methoxybenzyl group, trityl group, tosyl group, mesyl group, formyl group, chloroacetyl group, t-butoxycarbonyl group and the like. Protection of carbonyl group can be effected for example by converting it into 1,3-dioxolan or 1,3-dithian.

Next, stereoisomers of the compound of the present invention are described.

When R¹ in the formula (I) is hydrogen atom (the following formula (I)-e), equilibrium may exist in the benzimidazole ring between this formula and the following formula (I)-g as shown below. The existing ratio of each isomer in the following equilibrium varies depending on the conditions of the compound, such as its solid state or solution in an appropriate solvent.

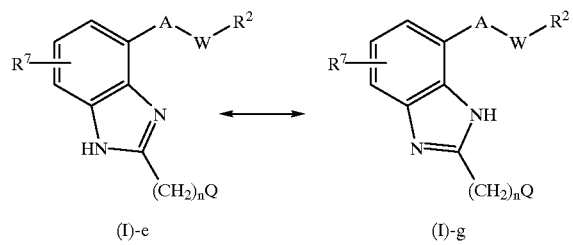

(I)-e    (I)-g

When A in the formula (I) is carbonyl group and W is methylene group (the following formula (I)-h), keto-enol equilibrium may exist between this formula and the following formula (XIV) as shown below. The existing ratio of each isomer in the following equilibrium varies depending on the conditions of the compound, such as its solid state or solution in an appropriate solvent or temperature.

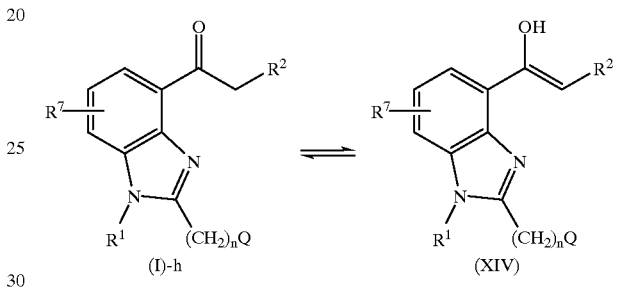

(I)-h    (XIV)

When A in the formula (I) is a group —(CH) (OR⁸)— or —CH(NHR⁹)CH₂—, an asymmetric carbon exists so that optical isomers exist. Also, diastereomers exist when A is a group —(CH) (OR⁸ )— or —CH(NHR⁹)CH₂— and R² represents —CONR⁴R⁵ at the same time wherein one of R⁴ and R⁵ is a group —CH(CH₂Ph)COOR⁶ and the other is hydrogen atom.

The present invention includes all of such optically active or inactive stereoisomer forms and equilibrium mixtures, as well as any desired mixtures thereof.

When the compounds represented by the formula (I) of the present invention contains an asymmetric carbon atom and optically active isomers are present, both the compounds exhibiting optical rotation of the value below zero (hereinafter referred to as (−) isomer) and the compounds exhibiting optical rotation of the value over zero (hereinafter referred to as (+) isomer) are present. The present invention includes racemate as well as both of such isomers.

The optically active compounds of the present invention, for example, a (−) isomer should be understood as a compound which is substantially free from the corresponding (+) isomer, and vice versa. Preferably, the optically active compounds of the present invention contains the corresponding isomer of opposite type at a content of less than 10%, more preferably at a content of less than 5%, and most preferably at a content of less than 1%. The term "single optically active compound" means one of the enantiomers of the given compound which is substantially free from the other enantiomer.

The pharmaceutical composition containing as its effective ingredient at least one of the optically active compounds represented by the formula (I) of the present invention or a pharmaceutically acceptable salt thereof may contain either the (+) isomer or the (−) isomer, and use of an optically active compounds the present invention which is a (−) isomer is more preferable.

Of the compounds represented by the formula (I) of the present invention, the preferable optically active compounds are those represented by the following formula (I)-w

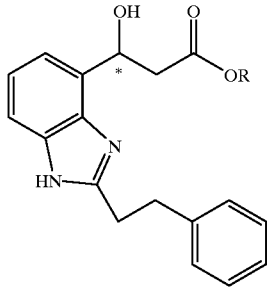

(I)-w (wherein R represents hydrogen atom or a lower alkyl group, and * is an asymmetric carbon atom) or a pharmaceutically acceptable salt thereof. More preferably, the compound is a (−) isomer.

Exemplary compounds represented by the formula (I) of the present invention include:

3-(2-(2-phenylethyl)benzimidazol-4-yl)-3-hydroxypropanoic acid; (+)-3-(2-(2-phenylethyl)benzimidazol-4-yl)-3-hydroxypropanoic acid; and (−)-3-(2-(2-phenylethyl)benzimidazol-4-yl)-3-hydroxypropanoic acid;

methyl 3-(2-(2-phenylethyl)benzimidazol-4-yl)-3-hydroxypropanoate; (+)-methyl 3-(2-(2-phenylethyl)benzimidazol-4-yl)-3-hydroxypropanoate; and (−)-methyl 3-(2-(2-phenylethyl)benzimidazol-4-yl)-3-hydroxypropanoate;

ethyl 3-(2-(2-phenylethyl)benzimidazol-4-yl)-3-hydroxypropanoate; (+)-ethyl 3-(2-(2-phenylethyl)benzimidazol- 4-yl)-3-hydroxypropanoate; and (−)-ethyl 3-(2-(2-phenylethyl)benzimidazol-4-yl)-3-hydroxypropanoate;

propyl 3-(2-(2-phenylethyl)benzimidazol-4-yl)-3-hydroxypropanoate; (+)-propyl 3-(2-(2-phenylethyl)benzimidazol-4-yl)-3-hydroxypropanoate; and (−)-propyl 3-(2-(2-phenylethyl)benzimidazol-4-yl)-3-hydroxypropanoate;

isopropyl 3-(2-(2-phenylethyl)benzimidazol-4-yl)-3-hydroxypropanoate; (+)-isopropyl 3-(2-(2-phenylethyl)benzimidazol-4-yl)-3-hydroxypropanoate; and (−)-isopropyl 3-(2-(2-phenylethyl)benzimidazol-4-yl)-3-hydroxypropanoate;

butyl 3-(2-(2-phenylethyl)benzimidazol-4-yl)-3-hydroxypropanoate; (+)-butyl 3-(2-(2-phenylethyl)benzimidazol-4-yl)-3-hydroxypropanoate; and (−)-butyl 3-(2-(2-phenylethyl)benzimidazol-4-yl)-3-hydroxypropanoate;

isobutyl 3-(2-(2-phenylethyl)benzimidazol-4-yl)-3-hydroxypropanoate; (+)-isobutyl 3-(2-(2-phenylethyl)benzimidazol-4-yl)-3-hydroxypropanoate; and (−)-isobutyl 3-(2-(2-phenylethyl)benzimidazol-4-yl)-3-hydroxypropanoate;

sec-butyl 3-(2-(2-phenylethyl)benzimidazol-4-yl)-3-hydroxypropanoate; (+)-sec-butyl 3-(2-(2-phenylethyl)benzimidazol-4-yl)-3-hydroxypropanoate; and (−)-sec-butyl 3-(2-(2-phenylethyl)benzimidazol-4-yl)-3-hydroxypropanoate; and tert-butyl 3-(2-(2-phenylethyl)benzimidazol-4-yl)-3-hydroxypropanoate; (+)-tert-butyl 3-(2-(2-phenylethyl)benzimidazol-4-yl)-3-hydroxypropanoate; and (−)-tert-butyl 3-(2-(2-phenylethyl)benzimidazol-4-yl)-3-hydroxypropanoate.

The compound of the present invention can form a salt with an inorganic or an organic acid. Examples of such salts include salts with inorganic acids such as hydrochlorides, hydrobromides, phosphates, sulfates, salts with organic acids such as acetate, oxalate, citrate, tartarate, maleate, alginate, p-toluenesulfonate, salicylate and salts with acidic amino acids such as glutamate, aspartate. The compound of the present invention can form salts with inorganic or organic bases depending on the substituent groups. Examples of such salts include alkali metal salts such as sodium salt, potassium salt, alkaline earth metal salts such as magnesium salt, calcium salt, salts with inorganic bases such as ammonium salt, salts with organic bases such as triethylamine salt, pyridine salt and salts with basic amino acids such as arginine salt, lysine salt, histidine salt. In addition, the compound of the present invention or salts thereof can form solvates with water, ethanol, glycerol and the like solvents, and such solvates are also included in the present invention.

The benzimidazole derivatives of the present invention or salts thereof can be produced by the procedures described in the following or by slight modifications thereof. In each of the following formulae, substituent groups of the formula (I) are as defined in the foregoing, and in other formulae, unless otherwise noted, $R^1$ represents hydrogen atom or a straight- or branched-chain alkyl group having 1 to 4 carbon atoms, $R^2$ represents cyano group, hydroxymethyl group, 2 -(2-imidazolyl)ethenyl group, a phenyl group substituted by one or two —$COOR^3$ groups, or a group —$COOR^3$ or —$CONR^4R^5$, $R^3$ represents hydrogen atom or a straight- or branched-chain alkyl group having 1 to 4 carbon atoms, each of $R^4$ and $R^5$ represents hydrogen atom, an alkyl group having 1 or 2 carbon atoms or a group —$CH_2COOR^6$ or —$CH(CH_2Ph)COOR^6$, wherein $R^4$ and $R^5$ may be the same or different from each other but, when one of $R^4$ and $R^5$ is a group —$CH_2COOR^6$ or —$CH(CH_2Ph)COOR^6$, the other one is hydrogen atom, A represents any one of groups selected from the class consisting of —CO—, —CH($OR^8$)—, —$CH_2O$—, —CH($NHR^9$)$CH_2$—, —CH=CH— and —$CH_2CH_2$—, W represents a group —$CH_2$— or a single bond, Q represents a phenyl group which may be substituted by one hydroxyl group, n is from 0 to 2, $R^6$ represents a straight- or branched-chain alkyl group having 1 to 4 carbon atoms, $R^7$ represents hydrogen atom, hydroxyl group, a halogen atom or a straight- or branched-chain alkoxyl group having 1 to 4 carbon atoms, $R^8$ represents hydrogen atom or acetyl group, $R^9$ represents hydrogen atom, acetyl group, phenylsulfonyl group or a benzoyl group which may be substituted by one methoxy group, and Y represents acetyl group, —$COOR^3$, a halogen atom, formyl group, chloroformyl group or bromoformyl group. The halogen atom means fluorine atom, chlorine atom, bromine atom or iodine atom.

Next, the compound of the present invention can be produced by general procedures represented by the following reaction formula. The following describes such methods in detail.

<Reaction Formula>

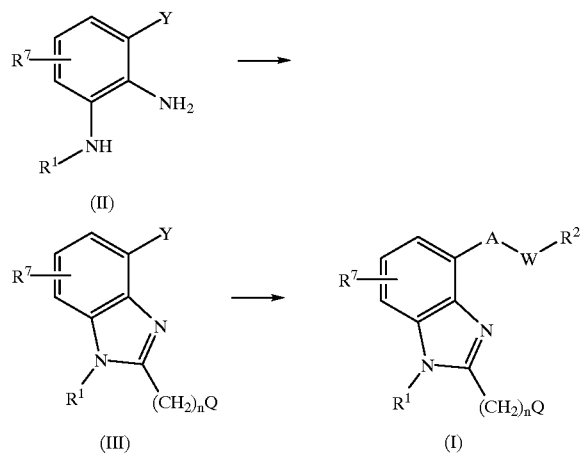

A compound represented by a formula (I)-b in which A in the formula (I) is carbonyl group, W is methylene group, $R^1$ is hydrogen atom and $R^2$ is —$COOR^3$ can be synthesized in accordance with the methods described for example in "New Experimental Chemistry Courses, Vol. 14, Synthesis and Reaction of Organic Compounds" edited by The Chemical Society of Japan (published by Maruzen), "Experimental Chemistry Courses 4th Edition, Vol. 22, Organic Synthesis IV" edited by The Chemical Society of Japan (published by Maruzen) or "Comprehensive Organic Transformations" edited by R. C. Larock (published by VCH, 1989).

<Procedure A>

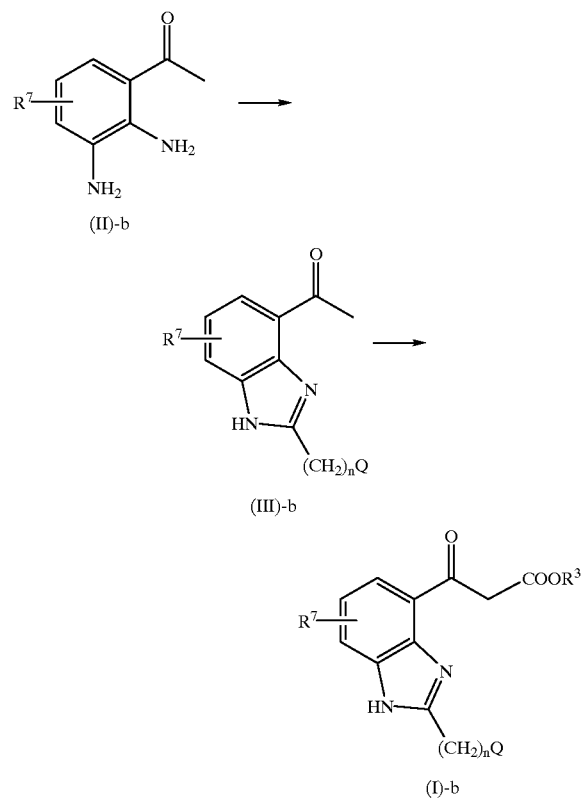

For example, a compound of the formula (I)-b in which $R^3$ is hydrogen atom (a carboxylic acid derivative) can be obtained by allowing a benzimidazole derivative represented the formula (III)-b, which is obtained from a 2,3-diaminoacetophenone derivative as a compound of the formula (II)-b, to react with carbon dioxide in a reaction inert solvent such as a halogenated hydrocarbon solvent (chloroform, dichloromethane or the like for example), an ether solvent (diethyl ether, tetrahydrofuran (THF) or the like for example) or acetonitrile, dimethyl sulfoxide (DMSO), N,N-dimethylformamide (DMF) or the like polar solvent, preferably in DMSO, in the presence of potassium carbonate, sodium carbonate, calcium carbonate, sodium hydride, sodium amide or the like inorganic base or triethylamine, 1,8-diazabicyclo[5.4.0]-7-undecene or the like organic base, preferably in the presence of potassium carbonate, if necessary by adding a phase-transfer catalyst such as 18-crown-6-ether or the like crown ether compound, or magnesium chloride, sodium iodide or diphenylurea, at a temperature of from −78° C. to reflux temperature of the solvent used, preferably from 0° C. to 30° C. The carboxylic acid derivative can also be obtained by allowing a carbamato complex, which is obtained for example by a combination of 2-imidazolidinthione, ethylmagnesium bromide and carbon dioxide, to react with the compound (III)-b in DMF or the like reaction inert solvent. The carboxylic acid derivative can also be converted into a compound of the formula (I)-b in which $R^3$ is a straight- or branched-chain alkyl group having 1 to 4 carbon atoms (an ester derivative), using diazomethane, trimethylsilyldiazomethane, diethyl sulfate or the like dialkyl sulfate or methyl iodide or the like alkyl halide as an alkylating agent. It can also be converted into the ester derivative by dehydrated and condensed reaction at a temperature of from −10° C. to reflux temperature of the solvent used, preferably from 0° C. to 30° C., using dicyclohexylcarbodiimide (DCC), 1,1'-carbonyldiimidazole (CDI), 2-chloro-1,3-dimethylimidazolinium hexafluorophosphate (CIP) or the like condensing agent, preferably using CIP, using an appropriate alcohol (methanol, ethanol, t-butanol or the like for example), a halogenated hydrocarbon solvent (chloroform, dichloromethane or the like for example), an aromatic hydrocarbon solvent (toluene or the like for example), an ether solvent (diethyl ether, THF or the like for example) or the like reaction inert solvent, preferably using dichloromethane or the like halogenated hydrocarbon solvent, and using potassium carbonate or the like inorganic base or pyridine, triethylamine or the like organic base, preferably using triethylamine or the like organic base. In addition, the ester derivative can also be synthesized using methanol, ethanol or the like appropriate alcohol in the presence of a catalyst such as sulfuric acid or the like mineral acid or boron trifluoride etherate ($BF_3 \cdot Et_2O$) or the like Lewis acid at a temperature of from 0° C. to reflux temperature of the solvent used, preferably with heating under reflux. Ester interchange of the thus obtained ester derivative can be effected by allowing it to react with an appropriate alcohol in the presence of the aforementioned mineral acid, Lewis acid or the like catalyst, and a desired ester can also be obtained by allowing the ester derivative to react with alkoxide of an appropriate alcohol.

In the aforementioned method, a compound represented by the formula (I)-b in which an alkoxycarbonyl group is introduced into the acetyl group and $R^3$ is a straight- or branched-chain alkyl group having 1 to 4 carbon atoms (an ester derivative) can be obtained by allowing a halogenoformic acid ester (ethyl chloroformate or the like for example), a carbonic acid diester (diethyl carbonate or the like for example), a phosphonoformic acid ester (ethyl phosphonoformate for example) or a oxalic acid ester (ethyl oxalate for example) and the like esters, in stead of carbon dioxide, to react with a compound represented by the formula (III)-b. A compound in which $R^3$ in the formula (I)-b is hydrogen atom (a carboxylic acid derivative) can be obtained for example by carrying out hydrolysis of these compounds (ester derivatives) at a temperature of from −78° C. to reflux temperature of the solvent used, preferably from 0° C. to reflux temperature of the solvent used, using an alkaline aqueous solution such as of sodium hydroxide, potassium hydroxide, sodium carbonate or the like, preferably using sodium hydroxide aqueous solution, and using an alcohol solvent (methanol, ethanol or the like for example) or an ether solvent (THF, dioxane or the like for example).
(Procedure A)

The compound represented by the formula (III)-b to be used in the procedure A can be obtained by the method shown in the following procedure A-1.

<Procedure A-1>

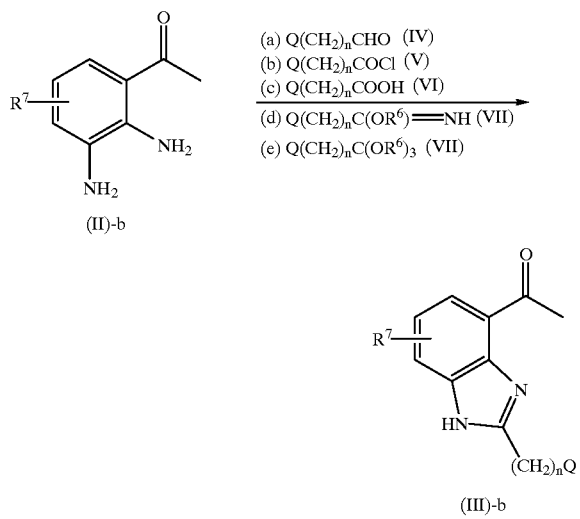

That is, it can be obtained by allowing a compound represented by the formula (II)-b to react with a compound represented by the following formula (IV)

$$Q(CH_2)_n\text{—CHO} \quad (IV)$$

(wherein Q and n are as defined in the aforementioned formula (I),
a compound represented by the following formula (V)

$$Q(CH_2)_n\text{—COCl} \quad (V)$$

(wherein Q and n are as defined in the aforementioned formula (I)),
a compound represented by the following formula (VI)

$$Q(CH_2)_n\text{—COOH} \quad (VI)$$

(wherein Q and n are as defined in the aforementioned formula (I)),
a compound represented by the following formula (VII)

$$Q(CH_2)_n\text{—C}(OR^6)\text{=NH} \quad (VII)$$

(wherein Q and n are as defined in the aforementioned formula (I), and $R^6$ is a straight- or branched-chain alkyl group having 1 to 4 carbon atoms), or
a compound represented by the following formula (VIII)

$$Q(CH_2)_n\text{—C}(OR^6)_3 \quad (VIII)$$

(wherein $R^6$, Q and n are as defined in the aforementioned formula (I)), under appropriate conditions. These reactions can be carried out in accordance with the methods disclosed in JP-A-3-27382 and WO 93/22313.

<Procedure B>

A compound represented by the formula (I)-b can also be synthesized using a benzimidazolylcarboxylic acid derivative represented by the formula (X) as the starting material which is obtained from a 2,3-diaminobenzoic acid derivative represented by the formula (IX). For example, a compound represented by the formula (I)-b can be synthesized by allowing a benzimidazolylcarboxylic acid ester derivative represented by the formula (X) to react with a malonic acid diester (diethyl malonate for example) or a malonic acid monoester (monoethyl malonate) in a reaction inert solvent such as an alcohol solvent (methanol, ethanol or the like for example), an ether solvent (diethyl ether, THF or the like for example) or DMSO, DMF or the like polar solvent, in the presence of sodium hydride, sodium alkoxide or the like base, subsequently hydrolyzing the ester to obtain a dicarboxylic acid monoester which is then subjected to decarboxylation. Alternatively, a compound in which $R^3$ in the formula (I)-b is hydrogen atom or a straight- or branched-chain alkyl group having 1 to 4 carbon atoms can be synthesized by preparing acetic acid or an acetic acid ester into a metal reagent using appropriate metalating agent such as butyl lithium and then allowing the reagent to react with a compound represented by the formula (X) in a reaction inert solvent such as an ether solvent (diethyl ether, THF or the like for example), an aromatic hydrocarbon solvent (benzene, toluene or the like for example) or DMSO, DMF or the like polar solvent, or by preparing a halogeno-acetic acid derivative (for example, ethyl chloroacetate, ethyl bromoacetate or ethyl iodoacetate) into Reformatsky reagent and then allowing the reagent to react with a compound represented by the formula (X). Also, a compound in which $R^3$ in the formula (I)-b is a straight or branched chain alkyl group having 1 to 4 carbon atoms (an ester derivative) can be obtained by allowing an acyl halide or an active amide (for example, an acylimidazole derivative or the like), which is obtained from a compound of the formula (IX) in which $R^3$ is hydrogen atom, to react with Meldrum's acid in a halogenated hydrocarbon solvent (chloroform, dichloromethane or the like for example) in the presence of pyridine, triethylamine or the like base, thereby converting it into acyl Meldrum's acid which is then subjected to solvolysis using an appropriate alcohol and subsequent decarboxylation. Also, the just described acyl halide or active amide can be converted into the ester derivative by allowing it to react with magnesium salt of a malonic acid monoester, magnesium salt of ethyl acetoacetate or lithium salt of ethyl acetate in a reaction inert solvent such as an ether solvent (diethyl ether, THF or the like for example), an aromatic hydrocarbon solvent (benzene, toluene or the like for example) or acetonitrile, if necessary in the presence of triethylamine or the like base, subsequently carrying out hydrolysis, decarboxylation by heating or deacetylation as occasion demands. In addition, a compound represented by the formula (I)-b ca n also be synthesized by allowing the aforementioned acyl halide or active amide to react with a malonic acid diester (diethyl malonate for example) or a malonic acid monoester (monoethyl malonate) in a reaction inert solvent such as an ether solvent (diethyl ether, THF or the like for example) or DMSO, DMF or the like polar solvent, in the presence of sodium hydride, sodium alkoxide or the like base, subsequently hydrolyzing the ester as occasion demands to obtain a dicarboxylic acid monoester which is then subjected to decarboxylation. (Procedure B)

<Procedure C>

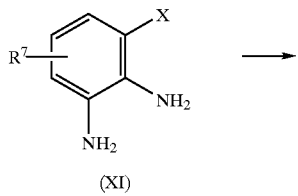

(XI)

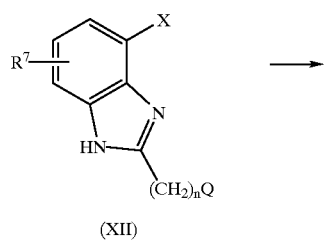

(XII)

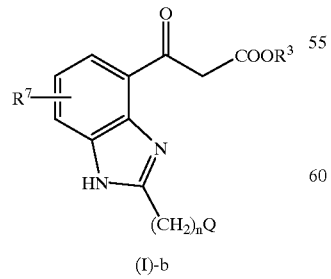

(I)-b

In addition, a compound in which $R^3$ in the formula (I)-b is a straight or branched chain alkyl group having 1 to 4 carbon atoms (an ester derivative) can be synthesized by allowing a halogeno-benzimidazole compound represented by the formula (XII) (X means a halogen atom), which can be obtained easily from a 2,3-diaminohalogenobenzene derivative represented by the formula (XI), directly as the compound (XII) or after preparing the compound (XII) into an organic metal reagent such as a boron reagent or tin reagent as occasion demands, to react with ethyl propionate or the like acetylene compound in an reaction inert solvent using a transition metal complex such as palladium acetate or the like palladium complex or tetrakis (triphenylphosphine)nickel (Ni(PPh$_3$)$_4$) or the like nickel complex, thereby effecting their cross-coupling reaction to introduce an acetylene side chain and then carrying out hydration of the acetylene group, for example using mercury oxide, or by preparing a compound represented by the formula (XII) into an organic metal reagent through a halogen-metal exchange reaction of its halogen atom using butyl lithium or the like organic lithium reagent and then allowing the resulting product to react with ethyl malonate chloride, subsequently carrying out its hydrolysis and decarboxylation in accordance with the aforementioned method. The ester derivative can be hydrolyzed in the usual way. (Procedure C)

A compound represented by a formula (I)-c in which A in the formula (I) is —CH(OH)—, W is methylene group, $R^1$ is hydrogen atom and $R^2$ is —COOR$^3$ ($R^3$ is as defined in the foregoing) can be synthesized in accordance with the methods described for example in "Shin Jikken Kagaku Koza, Vol. 14, Synthesis and Reaction of Organic Compounds" edited by The Chemical Society of Japan (published by Maruzen), "Experimental Chemistry Courses 4th Edition, Vol. 22, Organic Synthesis II" edited by The Chemical Society of Japan (published by Maruzen) or "Comprehensive Organic Transformations" edited by R. C. Larock (published by VCH, 1989). For example, it can be synthesized by the following procedure.

<Procedure D>

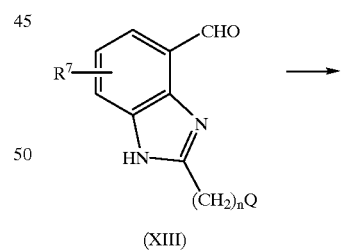

(XIII)

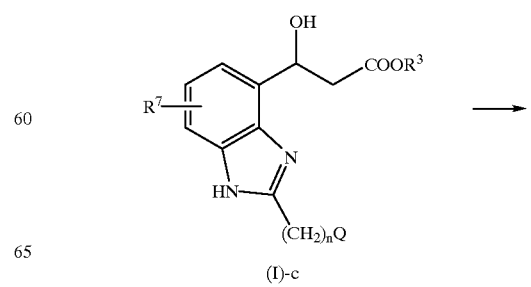

(I)-c

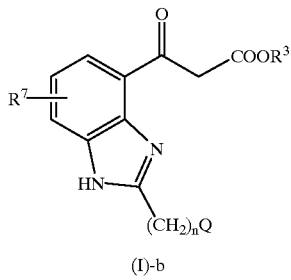

(I)-b

A compound represented by the formula (XIII) which is obtained from a 2,3-diaminobenzaldehyde derivative (as occasion demands, the formyl group may be protected with a protecting group described in "Protective Groups in Organic Synthesis 2nd Edition" edited by T. W. Greene and P. G. M. Wutz, published by John Wiley and Sons, 1991, or in "Protecting Groups" edited by P. J. Kocienski, published by Georg Thieme Verlag, 1994, during the reaction and then deprotected after completion of the reaction) can be converted into the compound (I)-c using the same reaction conditions and reagents described in the procedure B. That is, the compound of formula (I)-c can be obtained by preparing acetic acid or an acetic acid ester into a metal reagent using butyl lithium or the like appropriate metalation agent and then allowing the reagent to react with the compound of formula (XIII) in a reaction inert solvent such as an ether solvent (diethyl ether, THF or the like for example), an aromatic hydrocarbon solvent (benzene, toluene or the like for example) or DMSO, DMF or the like polar solvent. The compound of formula (I)-c can also be obtained by the use of a malonic acid ester derivative or Meldrum's acid as described in the procedure B. The thus obtained compound represented by the formula (I)-c can be converted into the compound of formula (I)-b using chromium oxide, potassium peroxide, manganese dioxide or the like metallic oxidizing agent or pyridinium chlorochromate, pyridinium dichromate or the like organic oxidizing agent or by Swern oxidation. (Procedure D)

<Procedure E>

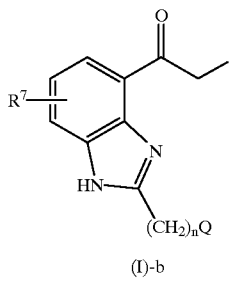

(I)-b

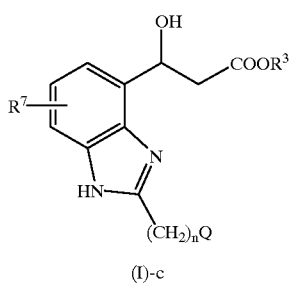

(I)-c

The compound represented by the formula (I)-b obtained by the procedure A, B, C or D can be converted into the compound of formula (I)-c by carrying out its reaction with sodium borohydride (NaBH$_4$), lithium aluminum hydride (LiAlH$_4$), borane (BH$_3$), alane (AlH$_3$) or the like metal hydride or a reducing reagent prepared therefrom by partial or entire appropriate substitution, preferably sodium borohydride, in methanol or ethanol at a temperature of from −50° C. to reflux temperature of the solvent used, preferably from 0° C. to 30° C. It can also be converted into a compound represented by the formula (I)-c in which R$^3$ is a straight- or branched-chain alkyl group having 1 to 4 carbon atoms (an ester derivative) for example by its hydrogenation through catalytic reduction using palladium/carbon or the like catalyst. The thus obtained ester derivative (I)-c can be converted into a carboxylic acid derivative by its hydrolysis in accordance with the aforementioned method.

(Procedure E)

The compound (I)-c may exist in optical isomer forms, and each of the optically active substances can be obtained by the methods described for example in "Asymmetric Synthesis and Advance in Optical Resolution" (edited by Otsuka and Mukaiyama, 1982, Kagaku Zokan 97, Kagaku Dojin Shuppan) or "High Selectivity Reaction" (edited by Nozaki, Mukaiyama and Noyori, 1981, Kagaku Zokan 91, Kagaku Dojin Shuppan). An example of asymmetric reduction is described in the following procedure F, and an example of optical resolution is described in procedure G.

<Procedure F>

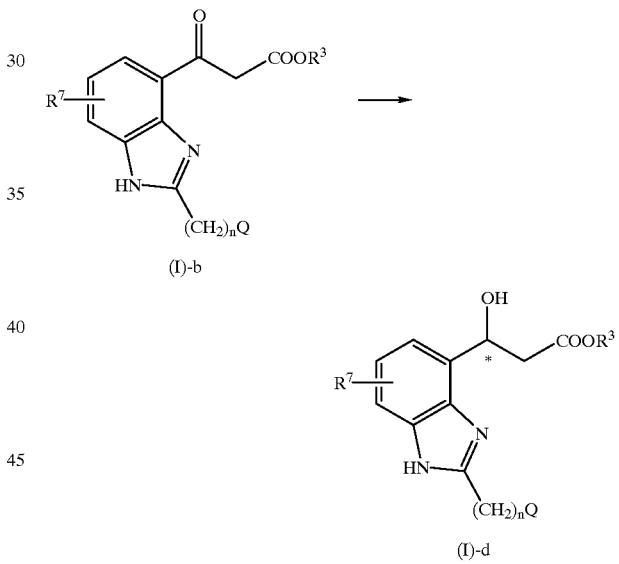

An optically active compound represented by the formula (I)-d can be obtained by allowing a β-ketocarboxylic acid derivative represented by the formula (I)-b to react with an appropriate reducing reagent shown below. In a first method, the compound is allowed to react with an asymmetric reducing agent (for example, BINAL-H, DIP-Cl or the like) prepared by modifying lithium aluminum hydride (LiAlH$_4$), sodium borohydride (NaBH$_4$), borane (BH$_3$) or the like metal hydride reducing agent partially or entirely with an asymmetric substituent group in a reaction inert solvent such as an ether solvent (diethyl ether, THF or the like for example) at a temperature of from −100° C. to reflux temperature of the solvent used. In a second method, catalytic asymmetric hydrogenation is carried out using a complex catalyst of ruthenium, rhodium or the like transition metal having an optically active phosphine as a ligand, typically BINAP-Ru(OCOMe)$_2$, in a reaction inert solvent such as an ether solvent (diethyl ether, THF or the like) at a temperature of from −100° C. to reflux temperature of the solvent used. In a third method, asymmetric reduction is carried out using an enzyme which catalyzes asymmetric reduction, or a microorganism (baker's yeast for example) which contains said enzyme, as the asymmetric catalyst. (Procedure F)

<Procedure G>

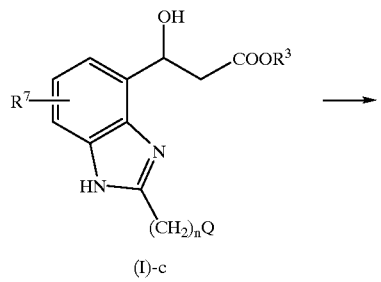

(I)-c

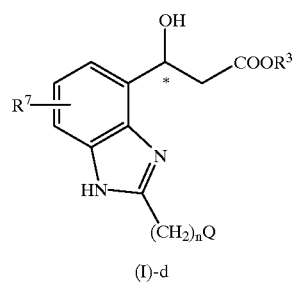

(I)-d

An optically active compound represented by the formula (I)-d can be obtained by carrying out optical resolution of the compound of formula (I)-c obtained by the procedure D or E.

Diastereomers are derived from the racemic compound (derivatizaion by covalent bond) using a reagent having asymmetric property (camphanic chloride, menthoxyacetyl chloride or the like for example), or diastereomer salts are formed (ionic bonding compound) by adding an acid or base having appropriate asymmetric property to the racemic compound, and then their separation is carried out based on the difference in their solubility and the like physical properties or by a chromatography and the like means. Thereafter, an optically active pure compound represented by the formula (I)-d can be obtained by removing the optically active modification group through chemical conversion and dissociation of the salt from the thus separated derivative.

As a direct method, an optically active compound represented by the formula (I)-d can also be separated from a compound represented by the formula (I)-c, for example, by a high performance liquid chromatography (HPLC) using CHIRALPAK AD™, CHIRALCEL OD™ (both manufactured by Daicel Chemical Industries, Ltd.) or other appropriate optically active column. The solvent used may be a mixed solvent of hexane with an alcohol such as ethylalcohol or isopropylalcohol, or such mixed solvent further supplemented with several percents of an amine such as diisopropylamine.

Alternatively, a diastereomeric salt may be derived by adding an acid or a base (such as cis-N-benzyl-2-(hydroxymethyl)cyclohexylamine) having an appropriate asymmetric property to the racemate, and conducing the separation on the bases of the difference in their solubility or other physical properties or by a chromatographic means or the like. The thus separated derivatives may be produced into the pure optically active compound by dissociation of the salt. (Procedure G)

Compounds in which $R^1$ in the formula (I) is a straight- or branched-chain alkyl group having 1 to 4 carbon atoms can be obtained by carrying out the reactions described in the procedures A to G, using a compound in which $R^1$ in the formula (II) is a straight- or branched-chain alkyl group having 1 to 4 carbon atoms and Y is acetyl group, —COOR$^3$ ($R^3$ is as defined in the foregoing), a halogen atom or formyl group, such as 2-amino-3-N-alkylaminoacetophenone, 2-amino-3-N-alkylaminobenzoic acid ester, 2-amino-3-N-alkylaminohalogenobenzene or 2-amino-3-N-alkylaminobenzaldehyde, in stead of the 2,3-diaminoacetophenone derivative, 2,3-diaminobenzoic acid ester derivative, 2,3-diaminohalogenobenzene derivative or 2,3-diaminobenzaldehyde derivative used as the material in the procedures A to G.

In consequence, compounds of the present invention can be produced by the procedure shown by the following reaction formula.

<Reaction Formula>

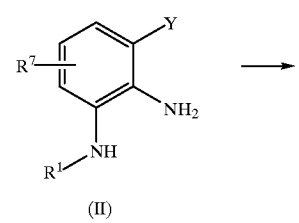

(II)

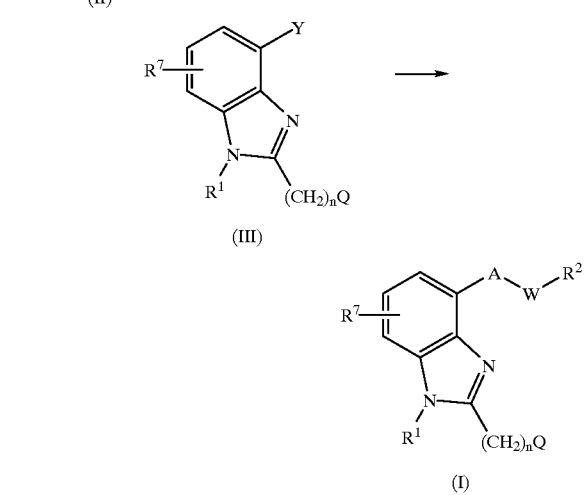

(III)

(I)

Compounds represented by the formula (I) can also be synthesized by the following methods.

<Procedure H>

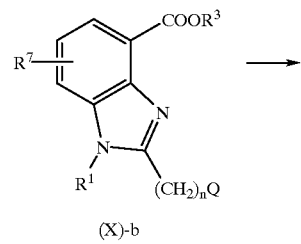

(X)-b

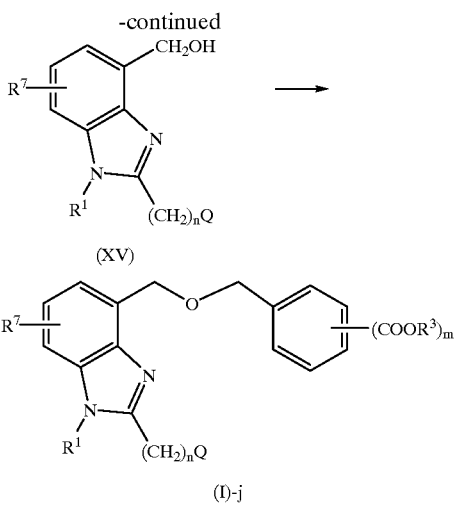

(XV)

(I)-j

A compound represented by the formula (X)-b can be converted into a compound represented by the formula (XV) by carrying out its reduction in a solvent such as an ether solvent (diethyl ether, THF or the like for example) using lithium aluminum hydride (LiAlH$_4$), borane (BH$_3$), alane (AlH$_3$) or the like metal hydride or a reducing agent prepared therefrom by partial or entire appropriate substitution, preferably lithium aluminum hydride.

A compound represented by the formula (I)-j in which A is a group —CH$_2$O— and W is a group —CH$_2$— (m is 1 or 2, and m means the number of substituent groups) can be obtained by allowing the compound of formula (XV) to react with a benzyl halide mono- or di-substituted by carboxyl group which may be protected, in an reaction inert solvent such as an ether solvent (diethyl ether, THF or the like for example) in the presence of sodium hydride or the like base at a temperature of from −100° C. to reflux temperature of the solvent used, preferably from −20° C. to room temperature. The thus obtained compound may be subjected to hydrolysis and the like treatment as occasion demands.

(Procedure H)

<Procedure J>

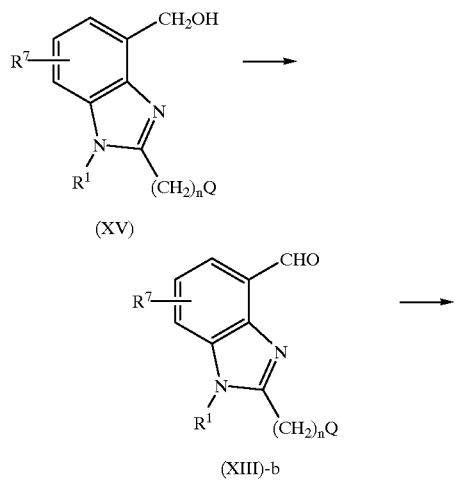

(XV)

(XIII)-b

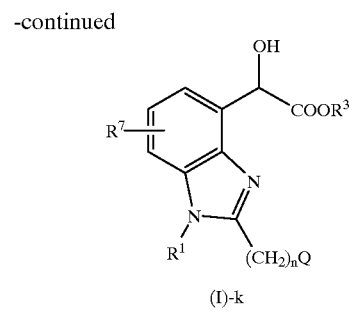

(I)-k

A compound represented by the formula (XIII)-b can be obtained by a method similar to the procedure D or by oxidizing the compound of formula (XV) using activated manganese dioxide, chromium trioxide or the like oxidizing agent in a reaction inert solvent such as an ether solvent (diethyl ether, THF or the like for example), a halogenated hydrocarbon solvent (chloroform, dichloromethane or the like for example), ethyl acetate or acetone.

A compound represented by the formula (I)-k can be obtained by allowing the compound of formula (XIII)-b to undergo the reaction in a halogenated hydrocarbon solvent (chloroform, dichloromethane or the like for example) in the presence of hydrogen cyanide or trimethylsilyl cyanide and zinc(II) iodide, cerium chloride or the like Lewis acid, thereby obtaining a cyanohydrin derivative which is subsequently hydrolyzed with hydrochloric acid or the like. The thus obtained carboxylic acid derivative may be subjected to its esterification in accordance with a method described in the procedure A.

(Procedure J)

<Procedure K>

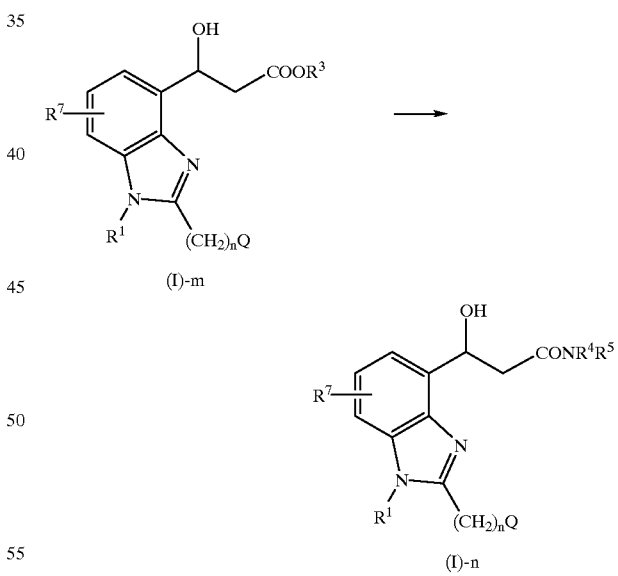

(I)-m (I)-n

A compound represented by the formula (I)-n can be obtained by allowing a compound represented by the formula (I)-m to react with ammonia, a primary amine or a secondary amine using water, an alcohol solvent (methanol, ethanol or the like for example) or the like as the solvent.

The compound of formula (I)-n can also be obtained by allowing a carboxylic acid of the formula (I)-m in which R$^3$ is H to react with a primary amine, a secondary amine, an amino acid or the like amine in DMF or the like reaction inert solvent using dicyclohexylcarbodiimide (DCC), benzotriazol-1-yloxytris(dimethylamino)phosphonium hexafluorophosphate (BOP) or the like condensing agent.
(Procedure K)
<Procedure L>

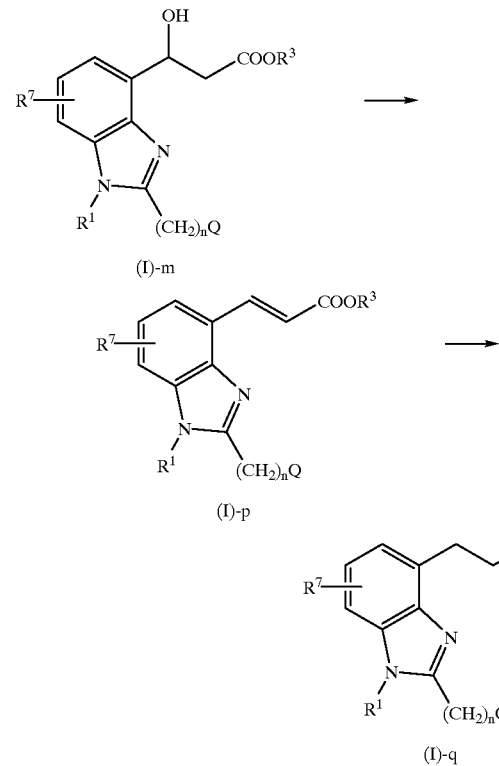

(I)-m (I)-p (I)-q

A compound represented by the formula (I)-p can be obtained by converting the compound of formula (I)-m into a halogeno compound by the use of a halogenating reagent such as thionyl chloride or phosphorus oxychloride or a corresponding bromide in a halogenated hydrocarbon solvent (dichloromethane, chloroform or the like for example) or the like reaction inert solvent, pyridine, triethylamine or the like basic solvent or a mixed solvent thereof, or into a corresponding sulfonyloxy compound using mesyl chloride, tosyl chloride or the like sulfonylating reagent, and then allowing the thus obtained compound to react with 1,8-diazabicyclo[5.4.0]-7-undecene (DBU) or the like base. The thus obtained compound represented by the formula (I)-p can be converted into a compound represented by the formula (I)-q by carrying out its hydrogenation under the same conditions of the procedure P which will be described later.
(Procedure L)
<Procedure M>

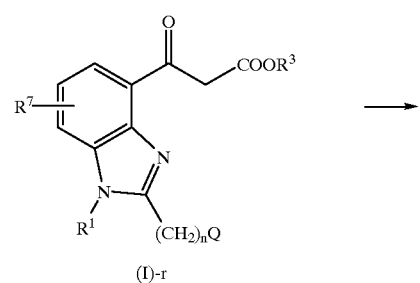

(I)-r

-continued

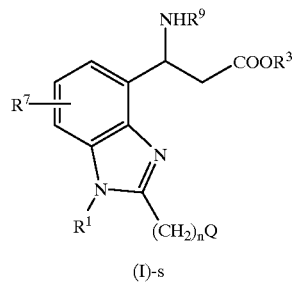

(I)-s

A compound represented by the formula (I)-s in which $R^9$ is H (an amino compound) can be obtained by converting a compound represented by the formula (I)-r into an oxime derivative by allowing it to react with hydroxylamine, O-benzylhydroxylamine or the like, if necessary in the presence of sodium hydroxide, triethylamine or the like base, in an alcohol solvent (methanol or ethanol for example) or the like reaction inert solvent, pyridine or the like basic solvent or a mixed solvent thereof, and then carrying out hydrogenation in an alcohol solvent (methanol, ethanol or the like for example), ethyl acetate or the like reaction inert solvent in the presence of palladium/carbon or the like catalyst. The compound of formula (I)-s can also be synthesized by effecting alkylation, acylation or sulfonylation of the thus obtained amino compound using an alkyl halide or the like alkylation reagent, acetyl chloride or the like acylating reagent or tosyl chloride or the like sulfonylating reagent in a reaction inert solvent such as a halogenated hydrocarbon solvent (chloroform, dichloromethane or the like for example) in the presence of pyridine or the like base.

Also, the compound of formula (I)-s can be synthesized by allowing the compound of formula (I)-r to form an imine with ammonium acetate or the like ammonium salt in a reaction inert solvent such as an alcohol solvent (methanol, ethanol or the like for example), and reducing the imine using sodium cyanoborohydride, sodium triacetoxyborohydride or the like reducing agent.

In addition, the compound of formula (I)-s can also be obtained by allowing the compound (I)-p obtained in the aforementioned procedure L to undergo addition reaction of an amine or addition of hydroxylamine and reduction.

(Procedure M)
<Procedure N>

(III)-c

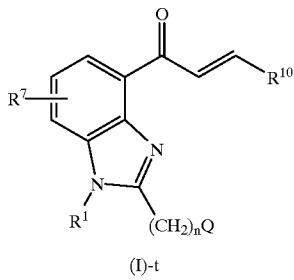

(I)-t

A compound represented by the formula (I)-t can be obtained by allowing a compound represented by the formula (III)-c to react with an aldehyde ($R^{10}CHO$ ($R^{10}$ represents 2-imidazolyl group)) in the presence of sodium hydroxide or the like base in water or an alcohol solvent (for example, methanol or ethanol) or the like reaction inert solvent at a temperature of from 0° C. to reflux temperature of the solvent used.
(Procedure N)
<Procedure P>

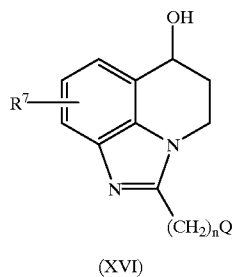

(XVI)

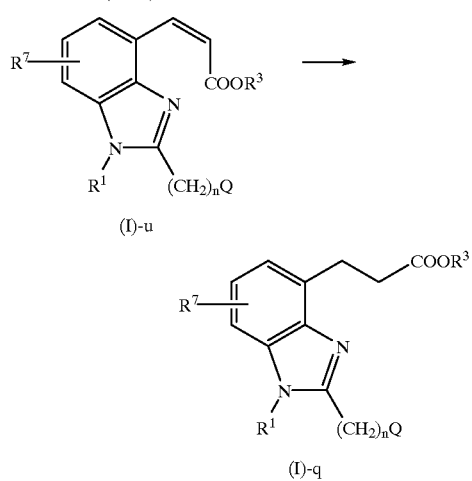

A compound represented by the formula (XVI) can be converted into a compound represented by the formula (I)-u by preparing it into a halogeno compound or a sulfonyloxy compound in accordance with a method described in the procedure L, forming a double bond through the elimination of a hydrogen halide or sulfonic acid by carrying out the reaction in DMF or the like reaction inert solvent at a temperature of from room temperature to reflux temperature of the solvent used in the presence of potassium carbonate, triethylamine, DBU or the like base as occasion demands and then allowing the resulting compound to react with potassium permanganate or the like oxidizing agent in a halogenated hydrocarbon solvent (chloroform or dichloromethane for example) or the like reaction inert solvent in the presence of butyltriethylammonium chloride or the like catalyst to obtain a compound represented by the formula (XVII) which is subsequently hydrolyzed. A compound represented by the formula (I)-q can be obtained by carrying out hydrogenation of the thus obtained compound in an alcohol solvent (methanol or ethanol for example) or the like reaction inert solvent in the presence of palladium/carbon or the like catalyst. The compound (I)-q can also be obtained by carrying out hydrogenation of the compound (I)-p described in the procedure L.
(Procedure P)
<Procedure Q>

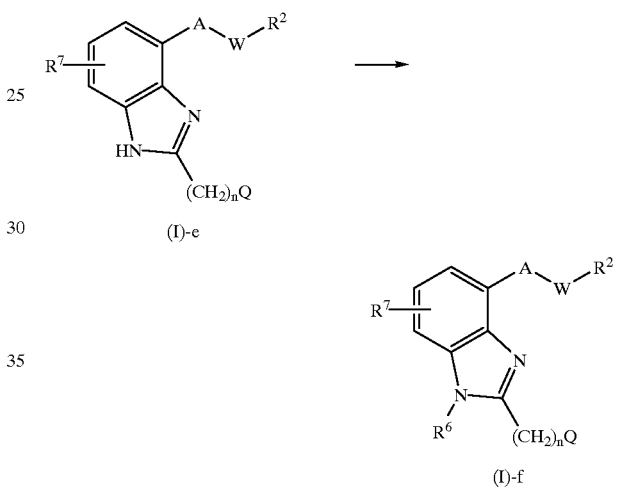

A compound represented by the formula (I)-f in which $R^1$ in the formula (I) is a straight or branched-chain alkyl group having 1 to 4 carbon atoms can be obtained by carrying out N-alkylation of a compound represented by the formula (I)-e in which $R^1$ is hydrogen atom. More illustratively, as shown in the above reaction formula, the compound represented by the formula (I)-f in which $R^1$ in the formula (I) is a straight or branched-chain alkyl group having 1 to 4 carbon atoms can be obtained by allowing the compound of formula (I)-e to react with dimethyl sulfate, methyl iodide or the like alkylating agent in a reaction inert solvent such as a halogenated hydrocarbon solvent (chloroform or dichloromethane for example), an ether solvent (diethyl ether or THF for example) or acetone, DMSO, DMF or the like polar solvent in the presence of potassium carbonate, sodium carbonate, sodium bicarbonate or the like inorganic base or pyridine, triethylamine or the like organic base, preferably by allowing it to react with dimethyl sulfate in acetone solvent in the presence of sodium bicarbonate. (Procedure Q)

When $R^1$ is H and NH group is present on the benzimidazole ring or when hydroxyl group, carboxyl group, carbonyl group or the like reactive group is present as a substituent group in the procedures A to Q of the present invention, these groups can be protected optionally and said protecting group can be removed at the final step or at a necessary step in each procedure. Methods for the introduction and removal of these protecting groups are optionally selected depending on the types of the groups to be protected or the protecting groups and can be carried out for example by the methods described in "Protective Groups in Organic Synthesis 2nd Edition" edited by T. W. Greene and P. G. M. Wutz, published by John Wiley and Sons (1991) or in "Protecting Groups" edited by P. J. Kocienski, published by Georg Thieme Verlag, 1994.

For example, various protecting groups can be cited as the protecting group of hydroxyl group or carboxyl group, such as methyl group, ethyl group, t-butyl group and the like lower alkyl groups, benzyl group, 4-nitrobenzyl group and the like aralkyl groups, trimethylsilyl group and the like substituted silyl groups, acetyl group, benzoyl group and the like acyl groups, benzenesulfonyl group, tosyl group and the like arylsulfonyl groups and methoxymethyl group, tetrahydropyranyl group and the like groups. As the protecting group of NH group on the benzimidazole ring, benzyl group, p-methoxybenzyl group, trityl group, tosyl group, mesyl group, formyl group, chloroacetyl group, t-butoxycarbonyl group and the like can be exemplified. Protection of carbonyl group can be effected for example by converting it into 1,3-dioxolan or 1,3-dithian.

When $R^1$ in the formula (I) is hydrogen atom (the following formula (I)-e), equilibrium may exist in the benzimidazole moiety between this formula and the following formula (I)-g as shown below. The existing ratio of each isomer in the following equilibrium varies depending on the conditions of the compound, such as its solid state or solution in an appropriate solvent. Isomers in the equilibrium shown below cannot be separated, but their existing ratio can be analyzed by a spectroscopic means such as nuclear magnetic resonance (NMR). However, since the measurement is carried out generally in a solution in the case of the NMR analysis, there is a possibility that the existing ratio will change depending on the difference in the measuring solvent.

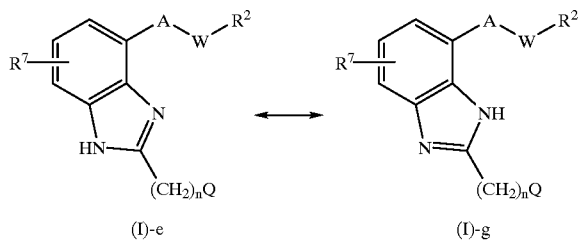

When A in the formula (I) is carbonyl group and W is methylene group (the following formula (I)-h), keto-enol equilibrium may exist between this formula and the following formula (XIV) as shown below. The existing ratio of each isomer in the following equilibrium varies depending on the conditions of the compound, such as its solid state or solution in an appropriate solvent or temperature. Isomers in the equilibrium shown below cannot be separated, but their existing ratio can be analyzed by a spectroscopic means such as nuclear magnetic resonance (NMR). However, since the measurement is carried out generally in a solution in the case of the NMR analysis, there is a possibility that the existing ratio will change depending on the difference in the measuring solvent.

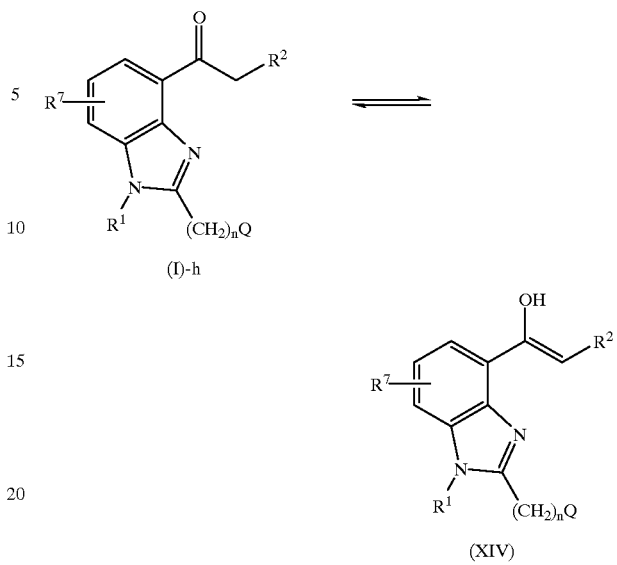

Next, actions of the compound of the present invention and pharmaceutical compositions of the present invention are described in detail. Actions of typical compounds are shown as test examples regarding their illustrative pharmacological actions, toxicity and the like, but the present invention is not restricted thereby.

TEST EXAMPLE 1

Action on Intraperitoneal Eosinophilia Model Mice

Using five animals per group of BALB/c male mice (about 25 g in body weight), 0.11 mL of physiological saline containing 0.1 mg of swine roundworm extract was administered into the peritoneal cavity of each mouse to sensitize. The same treatment was repeated 7 days after the administration and, 3 days thereafter, each animal was sacrificed by phlebotomy, 3 mL of physiological saline containing 1% dipotassium ethylenediaminetetraacetate (EDTA) was administered by intraperitoneal injection and its abdominal region was massaged for about 30 seconds. The abdominal region was incised to collect intraperitoneal fluid which was subsequently centrifuged at 130×g for 10 minutes, and the resulting precipitate was mixed with 500 μl of fetal calf serum containing 1% EDTA to prepare a cell suspension. A portion of the cell suspension was daubed on a slide glass using a spinner to carry out Diff-Quik staining, and then total leukocytes and eosinophils were counted to calculate the ratio of eosinophils in the total leukocytes. The number of total leukocytes in the cell suspension was measured using an automatic blood cell counter. The number of eosinophils in the cell suspension was calculated by multiplying the ratio of eosinophils in the total leukocytes by the number of total leukocytes.

Each of the compounds to be tested was suspended in 5% acacia aqueous solution and orally administered once a day for a total of 10 times starting immediately after the initial sensitization (test compound-administered group). Also, 5% acacia aqueous solution was orally administered to a group of mice in which sensitization and administration of test compounds were not carried out (non-treated group) and another group of mice in which sensitization was carried out but test compounds were not administered (control group).

The dose of each compound to be tested and the intraperitoneal eosinophilia inhibition rate calculated by the following formula are shown in Table 1.

Eosinophilia inhibition rate (%)={1−(test compound-administered group−non-treated group)/(control group−non-treated group)}× 100

TABLE 1

| Test compound (Example No.) | Dose (mg/kg/day) | Intraperitoneal eosinophilia inhibition rate (%) |
|---|---|---|
| 1 | 3 | 67 |
|   | 30 | 78 |
| 2 | 100 | 42 |
| 3 | 10 | 67 |
|   | 30 | 75 |
| 5 | 100 | 62 |
| 6 | 3 | 35 |
|   | 10 | 59 |
| 7 | 0.3 | 55 |
| Prednisolone acetate | 10 | 61–85 |

Prednisolone acetate: 11β, 17α, 21-trihydroxypregna-1, 4-diene-3, 20-dione 21-acetate Each of compounds of the present invention showed significant inhibitory action on intraperitoneal eosinophilia in BALB/c mice sensitized with the parasite extract.

The optically active compounds of the present invention showed inhibitory action on intraperitoneal eosinophilia of equivalent level for both their (+) isomer and (−) isomer.

TEST EXAMPLE 2

Action of IFN-γ Production Enhancement in Tumor-bearing Mouse

B16F10 cells cultivated in DMEM (Dulbecco's medium) supplemented with 10% FCS (fetal calf serum) were treated with trypsin, washed with PBS (phosphate buffered saline, pH 7.4), and adjusted in PBS to $1 \times 10^7$ cells/ml. The cells were subcutaneously injected in the abdomen of male C57BL/6 mouse (7 week old; body weight, about 23 g) at a dose of 0.1 ml/mouse. The day of tumor inoculation was designated day 0, and the tumor diameter was measured at day 7 with a vernier caliper. The tumor volume was calculated in terms of (minor diameter)$^2$×(major diameter), and the mice were grouped by using this value and the body weight for the indexes. The grouping was conducted for the mice which showed sufficient tumor growth at day 7, and the mice used in the test had an average tumor diameter of about 70 mm$^3$ and an average body weight of about 22 to about 23 g. The test compound was orally administered from day 7 to day 21. The solvent used was 0.5% HPMC (Hydroxy propyl methyl cellurose), and the control group was administered only with the solvent. At day 22, the mice were decapitated and the spleens were removed. After weighing the organs, the spleen was homogenized with a glass homogenizer, adjusted to $5 \times 10^6$ cells/ml, and cultivated in S-Clone SF-B medium (Sanko Pure Chemicals). The culture supernatant was collected after 24 hours, and lyophilized at −80° C. The supernatant was measured for its IFN-γ concentration (pg/mL) by EIA (Enzyme Immunoassay). The measurement was conducted with an assay kit of ENDOGEN. The dose of the test compound and IFN-γ concentration are shown in Table 2.

TABLE 2

| Test compound (Inventive Example No.) | Dose (mg/kg/day) | IFN-γ concentration (pg/ml) |
|---|---|---|
|   |   | (N = 7) |
| 6 | 10 | 125 |
| 6 | 30 | 194 |
| 6 | 100 | 263 |
| Control | — | 40 |

As evident from the results as described above, enhancement of the IFN-γ production of the spleen cell was observed when the tumor-bearing mouse was orally administered with the compound of the present invention and the spleen cells were cultivated with no immunostimulation (with no stimulation).

The optically active compound of the present invention showed enhancement of the IFN-γ production of equivalent level for both the (+) isomer and the (−) isomer.

TEST EXAMPLE 3

Toxicity Test

Toxicity of compounds of the present invention was examined. BALB/c male mice (about 25 g in body weight) were orally treated with the compounds of Inventive Examples 1, 2, 5, 7 and 10 suspended in 5% acacia aqueous solution at a dose of 100 mg/kg/day for 7 days, and the animals were observed for 3 days after completion of the administration, no mortal case was found and no abnormality was observed in terms of the body weight and general symptoms.

BALB/c male mice (about 25 g in body weight) were orally treated with the compounds of Inventive Examples 6, 7, 54 and 55 suspended in 0.5% aqueous solution of HPMC at a dose of 100 mg/kg/day for 4 days, and the animals were observed. No mortal case was found and no abnormality was observed in terms of the body weight and general symptoms.

SD female rats were orally treated with the compounds of Inventive Examples 54 and 55 suspended in 0.5% aqueous solution of HPMC at a dose of 300 mg/kg/day for 14 days. A significant increase in the relative liver weight was observed in the group administered with the compound of Inventive Example 54 while no such increase was observed for the compound of the Inventive Example 55, indicating the superior safety of the (−) isomer for the compound of the present invention.

Since the ester bond of the compounds of Inventive Examples 54 and 55 is hydrolyzed in the rat to generate carboxyl group, (−) isomer of Inventive Example 9 is more preferable for the compounds in the Inventive Examples 8 and 9.

As is evident from the above description and results of the test examples, the compound of the present invention strongly inhibits intraperitoneal eosinophilia in the experimental animal model sensitized with a parasite extract. Also, the compound of the present invention has a selective IgE antibody production inhibition action and shows its efficacy in a bronchoconstrictive reaction model of sensitized animals.

The compound of the present invention was also indicated to have the action of enhancing the IFN-γ production of the immunocompetent cell when orally administered.

In addition, the compound of the present invention shows excellent oral bioavailability and high safety with extremely low toxicity. Of the optically active compounds of the present invention, use of the (−) isomer is more preferable for use in a pharmaceutical composition.

The compound of the present invention having benzimidazole nucleus is effective for the prevention, protection against onset, protection against worsening of symptoms, improvement of symptoms and treatment, including remedy, of diseases which exhibit eosinophilia, namely parasite infection, hypereosinophilic syndrome (HES), eosinophilic pneumonia (PIE syndrome), eosinophilic enterogastritis, bronchial asthma, atopic dermatitis, allergic rhinitis, nettle rash, hypersensitivity pneumonitis, pulmonary aspergillosis, eosinophilic leukemia and the like diseases, and is particularly effective for the prevention or treatment of various allergic diseases including bronchial asthma.

In addition to the above diseases, it is possible to use the compound of the present invention in IgE antibody-induced diseases, namely various allergic diseases such as hay fever, angioneurotic edema, serous otitis media, pollinosis, allergic enterogastritis, food allergy, drug allergy and the like.

The pharmaceutical composition of the present invention is effective in controlling various symptoms of the diseases cited above and also can be used in preventive administration; for example, in the case of its administration to a patient suffering from a seasonal allergic disease (pollinosis for example), the patient can go through the season showing substantially no symptoms or with markedly slight symptoms when its administration is started just before the required season and continued until the end of the season.

When the enhancer for IFN-γ production containing the compound of the present invention is administered to animal or human, the immunocompetent cells are allowed to acquire the character of increased basal IFN-γ production rate under stationary conditions. As a consequence, stable IFN-γ production is expected in the absence of drug administration or stimulation, and increased IFN-γ production is expected in the presence of the drug administration or stimulation. Production of a safe drug with reduced side effects is thereby enabled in contrast to the case of direct IFN-γ administration or induction of the IFN-γ production by direct immuno-stimulation.

The enhancer for IFN-γ production of the present invention is also capable of enhancing the ability of inducing the IFN-γ production in those suffering from reduced ability of inducing the IFN-γ production.

The pharmaceutical composition of the present invention may also be used for prevention or treatment of the diseases wherein enhancement of the IFN-γ production is effective, for example, tumors, viral diseases (for example, viral hepatitis (type A, B, C, E, etc.), influenza, viral pneumonia, viral bronchitis, herpes infections (herpes simplex virus, EB virus (infectious mononucleosis), herpes zoster, polio, HIV infections, etc.), bacterial infections (for example, liver tumor, liver amebiasis), and the like. The pharmaceutical composition of the present invention is particularly suitable for use as an antitumor agent. The type of the organs and tissues applied are not limited, and exemplary such organs and tissues include liver, kidney, spleen, pancreas, brain, lung, digestive organs (stomach, small intestine, duodenum, large intestine, rectum, and the like), and also blood.

The enhancer for IFN-γ production of the present invention may be used also for prophylactic purposes. For example, gene diagnosis has recently enabled to diagnose diseases like familial tumor before their onset and at a fairly high accuracy. The pharmaceutical composition of the present invention can be administered to such patients of familial tumor for the purpose of preventing the onset of the disease. The compound of the present invention may be administered also to patients after the extirpation of the tumor to thereby prevent recurrence and metasitasis of the tumor. The pharmaceutical composition of the present invention may be also administered to the patient who is positive for the viral infection when diagnosed by a direct assay detecting the substance that is specific to the virus of the viral infection (antigen, nucleic acid) or an assay detecting the antibody against the virus to thereby prevent the onset of the viral infection. For example, the compound of the present invention can be used for symptomatic and asymptomatic HIV infections in the case of AIDS.

In general, the compound of the present invention or a salt thereof is orally administered as a medicament to human and other animals, but it can also be administered parenterally (for example, intravenous injection, intramuscular injection, subcutaneous injection, rectal administration, percutaneous absorption, transmucosal absorption and the like).

The medicament of the present invention is administered in the form of a pharmaceutical composition.

The pharmaceutical composition of the present invention contains at least one of the compounds of formula (I) of the present invention and is prepared in combination with a pharmaceutically acceptable carrier. More illustratively, various dosage forms can be obtained by optionally combining the compound of the present invention with a filler (for example, lactose, sucrose, mannitol, crystalline cellulose or silicic acid), a binder (for example, crystalline cellulose, sugar (mannitol or sucrose), dextrin, hydroxypropylcellulose (HPC), hydroxypropylmethylcellulose (HPMC), polyvinyl pyrrolidone (PVP) or macrogol), a lubricant (for example, magnesium stearate, calcium stearate or talc), a coloring agent, a flavoring agent, a disintegrating agent (for example, corn starch or carboxymethylcellulose), an antiseptic agent, a tonicity agent, a stabilizing agent (for example, a sugar or a sugar alcohol), a dispersing agent, an antioxidant (for example, ascorbic acid, butylhydroxyanisole (BHA), propyl gallate or dl-α-tocopherol), a buffer agent, a preservative agent (for example, paraben, benzyl alcohol or benzalkonium chloride), an aromatic agent (for example, vanillin, 1-menthol or rose oil), a solubility assisting agent (for example, cholesterol or triethanolamine), a suspending agent or an emulsifying agent and a pharmacologically acceptable appropriate carrier or solvent.

Examples of such dosage forms include capsules, pills, tablets, granules, fine subtilaes and powders, as well as suspensions, emulsions, lemonades, elixirs, syrups and the like mixtures for internal use, inhalations, sprays, aerosols, spreading preparations and the like mixtures for external use, solutions for eye-drops and nasal drops, adhesive preparations, ointments, lotions, liniments, poultices, suppositories, aqueous or non-aqueous injections, emulsions or suspensions for injection use and solid injections which are dissolved, emulsified or suspended when used.

Dose of the compound of the present invention when used as a medicament is an amount sufficient enough for treating each disease to be treated, which is optionally changed depending on the dosage form of the medicament, administration method, the number of times of administration per day, degree of symptoms, body weight, age and the like factors. Dose of the compound of the present invention as a medicament is within the range of from 0.01 to 5,000 mg, preferably from 0.1 to 500 mg, more preferably from 0.1 to 100 mg, per day per adult. In the case of oral administration, its dose is within the range of from 0.01 to 5,000 mg, preferably from 0.1 to 300 mg, more preferably from 0.1 to 100 mg, per day per adult. It may be administered once a day or by dividing the daily dose into 2 to 6 doses per day. The compound of the present invention may be used jointly with conventional therapeutic drugs.

EXAMPLES

Next, the present invention is described further in detail with reference to Inventive and Reference Examples, which by no means limit the present invention.

NMR was conducted with JNM-EX270 (manufactured by JEOL) or JEOL JNM-LA300 (manufactured by JEOL) and expressed by δ (ppm) using TMS (tetramethylsilane) for the internal standard. IR was measured by pellet method using potassium bromide or liquid film method (indicated as neat) using HORIBA FT-200 (manufactured by Horiba) and expressed by $cm^{-1}$. Melting point was measured using Mettler FP80 or FP90 (both manufactured by Mettler-Trade). Optical purity was measured by high performance liquid chromatography on LC-10 (manufactured by Shimadzu Corp.) using CHIRALCEL OD™ (Daicel Chemical Industries, Ltd.) and using hexane/isopropanol/diethylamine (80/20/1) for the eluent at a wavelength of 254 nm and temperature of 40° C., and indicated in terms of % e.e. Optical rotation was measured using JASCO DIP- 1000 (manufactured by JASCO) and expressed by specific rotation $[\alpha]_D$.

Reference Example 1

Synthesis of 4-acetyl-2-(2-phenylethyl) benzimidazole 2,3-Diaminoacetophenone (16.8 g) was dissolved in dry dichloromethane (170 mL) to which was subsequently added triethylamine (16.4 mL) while cooling in an ice bath. To this, cooled in the ice bath, was added dropwise dry dichloromethane (30 mL) solution of 3-phenylpropionic acid chloride (17.5 mL). After stirring for 40 minutes, the mixture was added to ice water (150 mL), and the layer was separated. The water layer was extracted with dichloromethane (150 mL) and the resulting organic layer was washed with brine. The combined organic layer was dried over anhydrous sodium sulfate and then the solvent was evaporated under a reduced pressure. The resulting residue was crystallized from ether and collected by filtration (26.5 g). The thus obtained crystal was suspended in toluene (530 mL) and added p-toluenesulfonic acid monohydrate (19.6 g). After heating under reflux for 30 minutes, the solvent was evaporated. The resulting residue was crystallized from ether and collected by filtration. The thus obtained crystal was suspended in ethyl acetate (200 mL), saturated sodium bicarbonate aqueous solution (150 mL) added and then the mixture was stirred. After separation of layers, the water layer was extracted with ethyl acetate (150 mL). The organic layer was combined and washed with water (100 mL) and brine (100 mL) in that order. After drying over anhydrous sodium sulfate, the solvent was evaporated under a reduced pressure. The resulting residue was dissolved in ethanol and activated charcoal (5 g) added. The activated charcoal was removed by filtration, and the resulting filtrate was concentrated under a reduced pressure. The resulting residue was crystallized from ether and hexane collected by filtration to obtain the title compound (21.9 g).

NMR (CDCl$_3$) δ [ppm]: 10.58 (1H, bs), 7.96 (1H, d, J=8 Hz), 7.77 (1H, d, J=8 Hz), 7.4–7.2 (6H, m), 3.3–3.2 (4H, m), 2.69 (3H, s)

IR (KBr) [$cm^{-1}$]: 3294, 3024, 1655, 1595, 1524, 1429, 1269, 1134, 744

Melting point: 102.3–105.9° C.

Reference Example 2

Synthesis of ethyl 2-(2-phenylethyl)benzimidazole-4-carboxylate

Ethyl 2,3-diaminobenzoate (25.3 g) was dissolved in dry dichloromethane (210 mL). While cooling in an ice bath and under an atmosphere of argon, to this solution was added triethylamine (19.7 mL), and to the reaction mixture was then added dropwise dry dichloromethane (38 mL) solution of 3-phenylpropionic acid chloride (21 mL) spending 1 hour, subsequently stirring the resulting mixture for 1 hour at the same temperature. Water (100 mL) was added to the reaction mixture and the layer was separated, and the water layer was extracted with dichloromethane. The organic layer was washed with brine and dried over anhydrous sodium sulfate and then the solvent was evaporated under a reduced pressure. To the resulting residue was added ether and a small amount of hexane, and to the amide compound collected by filtration (35.2 g) was added p-toluenesulfonic acid monohydrate (23.6 g) and toluene (352 mL), and the mixture was heated under reflux for 1 hour. The suspension was concentrated under a reduced pressure, and the resulting residue was crystallized from ether and collected by filtration. The thus obtained crystal was suspended in ethyl acetate (200 mL) and washed by stirring. The crystal was collected by filtration to obtain ethyl 2-(2-phenylethyl)benzimidazole-4-carboxylate p-toluenesulfonate (49.8 g). The thus obtained crystal was suspended in ethyl acetate (600 mL), and the suspension, cooled in an ice bath, was alkalified by adding saturated sodium bicarbonate aqueous solution (300 mL) to carry out separation of layers. The water layer was extracted with ethyl acetate. The organic layers were combined, washed with water (100 mL×2) and brine (100 mL), dried over anhydrous sodium sulfate and then mixed with activated charcoal. The drying agent and activated charcoal were removed by filtration, and the resulting filtrate was concentrated under a reduced pressure. The resulting residue was crystallized from hexane and collected by filtration to obtain the title compound (26.7 g).

NMR (CDCl$_3$) δ [ppm]: 10.04 (1H, bs), 7.93 (1H, d, J=8 Hz), 7.87 (1H, d, J=8 Hz), 7.4–7.2 (6H, m), 4.43 (2H, q, J=7 Hz), 3.3–3.1 (4H, m), 1.43 (3H, t, J=7 Hz)

Reference Example 3

Synthesis of 2-(2-phenylethyl)benzimidazole-4-carboxylic acid

To ethyl 2-(2-phenylethyl)benzimidazole-4-carboxylate (10 g) obtained in Reference Example 2 was added ethanol (46 mL) and water (68 mL) solution of sodium hydroxide (2.72 g), and the mixture was heated under reflux for 1 hour. After spontaneous cooling, this was mixed with water (100 mL) and washed with ether (200 mL). While cooling in an ice bath, the water layer was adjusted to pH 5. The thus formed precipitate was collected by filtration and washed with ether and ethanol (40 mL). The obtained precipitate was dried under a reduced pressure to obtain the title compound (8.49 g).

NMR (DMSO-d$_6$) δ [ppm]: 12.25 (1H, bs), 7.80 (1H, d, J=8 Hz), 7.74 (1H, d, J=8 Hz), 7.4–7.1 (6H, m), 3.3–3.0 (4H, m)

Reference Example 4

Synthesis of 4-acetyl-2-benzylbenzimidazole

According to Reference Example 1, using 2,3-diaminoacetophenone (20 g) and phenylacetyl chloride (18.5 mL), the title compound was obtained as crystal (19.2 g).

NMR (CDCl$_3$) δ [ppm]: 10.56 (1H, bs), 7.97 (1H, d, J=8 Hz), 7.76 (1H, dd, J=8, 1H), 7.4–7.3 (6H, m), 4.33 (2H, s), 2.67 (3H, s)

Reference Example 5

Synthesis of 3-(2-benzylbenzimidazol-4-yl)-3-oxopropanoic acid

According to Inventive Example 1, which is described later, using 4-acetyl-2-benzylbenzimidazole (19 g) obtained in Reference Example 4, the title compound was obtained as crystal (5.33 g).

NMR (DMSO-d$_6$) δ [ppm]: 12.74 (1H, bs), 7.9–7.8 (2H, m), 7.4–7.2 (7H, m), 4.27 (2H, s), 4.14 (1H, bs)

Reference Example 6

Synthesis of ethyl 2-phenylbenzimidazole-4-carboxylate

To a solution of ethyl 2,3-diaminobenzoate (3.0 g) in methanol (60 mL) was added 1 N hydrochloric acid (0.6 mL) and benzaldehyde (1.7 mL), and the mixture was stirred at room temperature for 1 hour. After evaporation of the solvent under a reduced pressure, to the solution of the obtained residue in dichloromethane was added silica gel. The solvent was evaporated under a reduced pressure, and the resulting residue was heated at 100° C. for 1 hour. By purifying the reaction mixture by a silica gel column chromatography (eluent:hexane/ethyl acetate), the title compound was obtained as crystal (1.8 g).

NMR (CDCl$_3$) δ [ppm]: 10.71 (1H, bs), 8.1–8.0 (2H, m), 8.03 (1H, d, J=8 Hz), 7.93 (1H, dd, J=8, 1 Hz), 7.6–7.5 (3H, m), 7.33 (1H, t, J=8 Hz), 4.50 (2H, q, J=7 Hz), 1.49 (3H, t, J=7 Hz)

Reference Example 7

Synthesis of 2-phenylbenzimidazole-4-carboxylic acid

According to Reference Example 3, using ethyl 2-phenylbenzimidazole-4-carboxylate (1.8 g) obtained in Reference Example 6, the title compound was obtained as crystal (1.5 g).

NMR (DMSO-d$_6$) δ [ppm]: 13.26 (1H, bs), 12.34 (1H, bs), 8.4–8.3 (2H, m), 7.93 (1H, d, J=8 Hz), 7.83 (1H, d, J=8 Hz), 7.6–7.5 (3H, m), 7.34 (1H, t, J=8 Hz)

Reference Example 8

Synthesis of ethyl 2-(2-(4-benzyloxyphenyl)ethyl)benzimidazole-4-carboxylate To a solution of ethyl 2,3-diaminobenzoate (2.5 g) in dry dichloromethane (20 mL) to which, while cooling in an ice bath, was subsequently added triethylamine (2.1 mL). To this was added dropwise dry dichloromethane (6 mL) solution of 4-benzyloxyphenylpropionic acid chloride (4 g). After stirring for 75 minutes in an ice bath, the reaction solution was poured into ice water (100 mL) extracted with dichloromethane. The resulting organic layers were combined, washed with water and brine in that order and then dried over anhydrous sodium sulfate. After evaporation of the solvent under a reduced pressure, the resulting residue was crystallized from hexane and collected by filtration to obtain crystal (5.57 g). The thus obtained crystal was added to toluene (50 mL) and p-toluenesulfonic acid monohydrate (2.8 g) and heated under reflux for 30 minutes. After evaporation of the solvent under a reduced pressure, the thus obtained residue was alkalified by adding saturated sodium bicarbonate aqueous solution. Ethyl acetate was added to the solution and the layer was separated. The water layer was extracted with ethyl acetate, and the resulting organic layers were combined and washed with water and brine in that order. After drying the thus treated organic layer over anhydrous sodium sulfate, the solvent was evaporated under a reduced pressure. The resulting residue was crystallized from ether and hexane and collected by filtration to obtain the title compound as crystal (3.3 g).

NMR (CDCl$_3$) δ [ppm]: 10.04 (1H, bs), 7.93 (1H, d, J=8 Hz), 7.87 (1H, d, J=8 Hz), 7.5–7.3 (6H, m), 7.17 (2H, d, J=8 Hz), 6.93 (2H, d, J=8 Hz), 5.05 (2H, s), 4.43 (2H, q, J=7 Hz), 3.3–3.1 (4H, m), 1.43 (3H, t, J=7 Hz)

Reference Example 9

Synthesis of 2-(2-(4-benzyloxyphenyl)ethyl)benzimidazole-4-carboxylic acid

Ethyl 2-(2-(4-benzyloxyphenyl)ethyl)benzimidazole-4-carboxylate (3.3 g) obtained in Reference Example 8 was added to ethanol (15 mL) and 1 N sodium hydroxide aqueous solution (16.5 mL), and the mixture was heated under reflux for 40 minutes.

The reaction solution was diluted with water and washed with ether, and the thus separated water layer was adjusted to pH 4 to 5 with 4 N hydrochloric acid. The thus precipitate was collected by filtration to obtain the title compound as crystal (2.72 g).

NMR (DMSO-d$_6$) δ [ppm]: 12.23 (1H, bs), 7.79 (1H, d, J=9 Hz), 7.73 (1H, d, J=9 Hz), 7.5–7.1 (8H, m), 6.91 (2H, d, J=9 Hz), 5.05 (2H, s), 3.2–3.0 (4H, m)

Reference Example 10

Synthesis of ethyl 3-(2-(2-(4-benzyloxyphenyl)ethyl)benzimidazol-4-yl)-3-oxopropanoate According to Inventive Example 12 which is described later, using 2-(2-(4-benzyloxyphenyl)ethyl)benzimidazole-4-carboxylic acid (2.72 g) obtained in Reference Example 9, the title compound was obtained (1.8 g).

NMR (CDCl$_3$) δ [ppm]: 10.55 (1H, bs), 7.99 (1H, d, J=8 Hz), 7.72 (1H, dd, J=8, 1 Hz), 7.5–7.3 (6H, m), 7.16 (2H, d, J=9 Hz), 6.92 (2H, d, J=9 Hz), 5.05 (2H, s), 4.24 (2H, q, J=7 Hz), 4.10 (2H, s), 3.3–3.1 (4H, m), 1.28 (3H, t, J=7 Hz)

Reference Example 11

Synthesis of 6-chloro-4,5-dihydro-2-(2-phenylethyl)-6H-imidazo[4,5,1-i,j]-quinoline hydrochloride To a solution of 4,5-dihydro-2-(2-phenylethyl)-6H-imidazo[4,5,1-i,j]quinolin-6-ol (118 g) was dissolved in dichloromethane (1.2 L) to which, cooled in an ice bath, was subsequently added dropwise thionyl chloride (95 mL). After 30 minutes of reaction at room temperature, the solvent was evaporated under a reduced pressure. Ether was added to the resulting residue, and the thus formed crystal was collected by filtration to obtain the title compound (139 g).

NMR (DMSO-d$_6$) δ [ppm]: 7.8–7.7 (1H, m), 7.6–7.5 (2H, m), 7.4–7.2 (5H, m), 5.81 (1H, t, J=3 Hz), 4.6–4.5 (1H, m), 4.2–4.0 (1H, m), 3.6–3.4 (2H, m), 3.3–3.1 (2H, m)

Reference Example 12

Synthesis of 2-(2-phenylethyl)-4H-imidazo[4,5,1-i,j] quinoline

6-Chloro-4,5-dihydro-2-(2-phenylethyl)-6H-imidazo[4,5, 1-i,j]-quinoline hydrochloride (10 g) obtained in Reference Example 11 and potassium carbonate (4.1 g) were suspended in N,N-dimethylformamide (20 mL), and the suspension was heated at 130° C. for 50 minutes. After spontaneous cooling, this was mixed with saturated sodium bicarbonate aqueous solution and extracted with ethyl acetate. The organic layer was washed with brine and then dried over anhydrous sodium sulfate. After evaporation of the solvent under a reduced pressure, the resulting residue was purified by a silica gel column chromatography (eluent: hexane/ethyl acetate) to obtain the title compound as crystal (5.6 g).

NMR (CDCl$_3$) δ [ppm]: 7.48 (1H, d, J=8 Hz), 7.4–7.2 (5H, m), 7.1–7.0 (1H, m), 6.82 (1H, d, J=7 Hz), 6.6–6.5 (1H, m), 5.8–5.7 (1H, m), 4.76 (2H, bs), 3.3–3.0 (4H, m)

Reference Example 13

Synthesis of 2-(2-phenylethyl)-4H-imidazo[4,5,1-i,j] quinolin-4-on

While stirring and cooling in an ice bath, to dichloromethane (100 mL) solution of 2-(2-phenylethyl)-4H-imidazo[4,5,1-i,j]-quinoline (5.0 g) obtained in Reference Example 12 was added dichloromethane (300 mL) suspension of potassium permanganate (4.56 g) and butyltriethylammonium chloride (6.56 g) spending 1 hour. After stirring at room temperature for 1 hour, to the reaction mixture was added potassium permanganate (1.52 g) and butyltriethylammonium chloride (2.19 g). After stirring overnight at room temperature, the reaction solution was added to 1 N sodium hydroxide aqueous solution (200 mL) and stirred at room temperature. The insoluble material was removed by filtration, and the resulting filtrate was separated. The water layer was extracted with dichloromethane, and the resulting organic layers were combined.

The combined organic layer was washed with water and brine in that order and then dried over anhydrous sodium sulfate. After evaporation of the solvent under a reduced pressure, the resulting residue was purified by a silica gel column chromatography (eluent: hexane/ethyl acetate) to obtain the title compound as colorless crystal (2.61 g).

NMR (DMSO-d$_6$) δ [ppm]: 8.18 (1H, d, J=9 Hz), 7.95 (1H, d, J=8 Hz), 7.79 (1H, d, J=8 Hz), 7.55 (1H, t, J=8 Hz), 7.4–7.2 (5H, m), 6.74 (1H, d, J=9 Hz), 3.60 (2H, t, J=8 Hz), 3.19 (2H, t, J=8 Hz)

Reference Example 14

Synthesis of ethyl 1-(4-methoxybenzyl)-2-(2-phenylethyl)benzimidazole-4-carboxylate Ethyl 2-(2-phenylethyl)benzimidazole-4-carboxylate (10 g) obtained in Reference Example 2, potassium carbonate (7.05 g) and p-methoxybenzyl chloride (7.99 g) were stirred in N,N-dimethylformamide (150 mL) at room temperature for 20 hours. The reaction solution was diluted with water and extracted with ether. The organic layer was washed with water and brine and dried over anhydrous sodium sulfate and then the solvent was evaporated under a reduced pressure. The resulting residue was purified by a silica gel column chromatography (eluent: hexane/ethyl acetate) and the desired fraction was concentrated under a reduced pressure to obtain the title compound as oil (10.1 g).

NMR (CDCl$_3$) δ [ppm]: 7.92 (1H, dd, J=8, 1 Hz), 7.38 (1H, dd, J=8, 1 Hz), 7.3–7.2 (6H, m), 6.88 (2H, d, J=9 Hz), 6.78 (2H, d, J=9 Hz), 5.15 (2H, s), 4.52 (2H, q, J=7 Hz), 3.76 (3H, s), 3.21 (4H, s), 1.48 (3H, t, J=7 Hz)

Reference Example 15

Synthesis of 4-hydroxymethyl-1-(4-methoxybenzyl)-2-(2-phenylethyl)benzimidazole

Ethyl 1-(4-methoxybenzyl)-2-(2-phenylethyl) benzimidazole-4-carboxylate (5.5 g) obtained in Reference Example 14 was dissolved in anhydrous tetrahydrofuran (55 mL). While cooling in an ice bath, lithium aluminum hydride (0.30 g) was added in small portions to the solution, and the mixture was stirred at the same temperature for 1 hour. The reaction solution was poured into ice water and mixed with ethyl acetate and then the insoluble material was removed by filtration. The resulting filtrate was separated, the organic layer was washed with brine and dried with anhydrous sodium sulfate, and then the solvent was evaporated under a reduced pressure. The resulting residue was crystallized from ether and hexane and collected by filtration to obtain the title compound (4.35 g).

NMR (CDCl$_3$) δ [ppm]: 7.3–7.1 (8H, m), 6.92 (2H, d, J=9 Hz), 6.80 (2H, d, J=9 Hz), 5.16 (2H, bs), 5.13 (2H, s), 4.35 (1H, bs), 3.76 (3H, s), 3.13 (4H, bs)

Reference Example 16

Synthesis of dimethyl (1-(4-methoxybenzyl)-3-(2-(2-phenylethyl)benzimidazol-4-yl)methoxymethyl) phthalate 4-Hydroxymethyl-1-(4-methoxybenzyl)-2-(2-phenylethyl)benzimidazole (1.0 g) obtained in Reference Example 15 was dissolved in anhydrous tetrahydrofuran (15 mL), and 60% sodium hydride (237 mg) was added in small portions to the thus prepared solution which was cooled in an ice bath. After stirring for 20 minutes at the same temperature, this was added to anhydrous tetrahydrofuran (2 mL) solution of dimethyl 3-bromomethylphthalate (927 mg) and stirred at the same temperature for 1.5 hours. The reaction solution was diluted with ice water and extracted with ethyl acetate. The organic layer was washed with brine and dried over anhydrous sodium sulfate, and then the solvent was evaporated under a reduced pressure. The resulting residue was purified by a silica gel column chromatography (eluent: hexane/ethyl acetate) and the desired fraction was concentrated under a reduced pressure to obtain the title compound as oil (1.03 g).

NMR (CDCl$_3$) δ [ppm]: 7.91 (1H, d, J=8 Hz), 7.87 (1H, d, J=8 Hz), 7.49 (1H, t, J=8 Hz), 7.4–7.2 (8H, m), 6.92 (2H, d, J=9 Hz), 6.80 (2H, d, J=9 Hz), 5.11 (4H, s), 4.79 (2H, s), 3.90 (3H, s), 3.87 (3H, s), 3.76 (3H, s), 3.2–3.1 (4H, m)

Reference Example 17

Synthesis of 2-bromo-4-methoxy-6-nitroaniline

To a solution of 4-methoxy-2-nitroaniline (35 g) in dichloromethane (350 mL) was subsequently added dropwise bromine (12.9 mL) at −20° C. After stirring for 30 minutes at the same temperature, this was poured into ice water, adjusted to pH 7 to 8 with saturated sodium bicarbonate aqueous solution and then extracted with dichloromethane. The organic layer was washed with brine and dried over anhydrous sodium sulfate, and then the solvent was evaporated under a reduced pressure. The resulting residue was purified by a silica gel column chromatography (eluent: hexane/ethyl acetate). After concentration of the desired fraction, the resulting residue was crystallized from hexane and ethyl acetate and then collected by filtration to obtain the title compound as reddish orange crystals (29.6 g).

NMR (CDCl$_3$) δ [ppm]: 7.63 (1H, d, J=3 Hz), 7.44 (1H, d, J=3 Hz), 6.38 (2H, bs), 3.80 (3H, s)

Reference Example 18

Synthesis of 2-amino-5-methoxy-3-nitrobenzonitrile

To a solution of 2-bromo-4-methoxy-6-nitroaniline (45 g) obtained in Reference Example 17 in N-methyl-2-pyrrolidone (225 mL) was subsequently added copper(I) cyanide (33 g). This was stirred at 150° C. for 5.5 hours. After spontaneous cooling, aqueous ammonia was added to the mixture and the resulting mixture was stirred for 20 minutes, and then insoluble material was separated by filtration. The thus separated residue was washed with ethyl acetate, and the filtrate and washed solution were combined to carry out separation of layers. The organic layer was dried over anhydrous sodium sulfate and then the solvent was evaporated under a reduced pressure to obtain the title compound as crystal (14.1 g).

NMR (CDCl$_3$) δ [ppm]: 7.90 (1H, d, J=3 Hz), 7.38 (1H, d, J=3 Hz), 6.45 (2H, bs), 3.83 (3H, s)

Reference Example 19

Synthesis of 2,3-diamino-5-methoxybenzonitrile

2-Amino-5-methoxy-3-nitrobenzonitrile (9.6 g) obtained in Reference Example 18 and 10% palladium/carbon (0.96 g) were suspended in methanol (96 mL). The suspension was stirred at room temperature for 16 hours under an atmosphere of hydrogen. The catalyst was removed by filtration, and the resulting filtrate was evaporated under a reduced pressure. The resulting residue was crystallized from ether and collected by filtration to obtain the title compound as crystal (7.0 g).

NMR (DMSO-d$_6$) δ [ppm]: 6.37 (1H, d, J=2 Hz), 6.21 (1H, d, J=2 Hz), 5.13 (2H, bs), 4.97 (2H, bs), 3.60 (3H, s)

Reference Example 20

Synthesis of 4-cyano-6-methoxy-2-(2-phenylethyl) benzimidazole

To a solution of 2,3-diamino-5-methoxybenzonitrile (7.0 g) obtained in Reference Example 19 in dry dichloromethane (140 mL), was added triethylamine (6.0 mL). While cooling in an ice bath, to this was added dropwise dry dichloromethane (70 mL) solution of 3-phenylpropionic acid chloride (6.4 mL) spending 2 hours. After stirring for 20 minutes at the same temperature, ice water (200 mL) was added thereto. Separation of layers was carried out, and the water layer was extracted with dichloromethane. The organic layer was combined and washed with brine and dried over anhydrous sodium sulfate, and the solvent was then evaporated under a reduced pressure. The thus obtained residue was crystallized from ether to obtain an amide compound (10.8 g). The thus obtained amide compound and p-toluenesulfonic acid monohydrate (7.7 g) were suspended in toluene (108 mL). After stirring for 30 minutes at 100° C., the solvent was evaporated under a reduced pressure. The thus obtained residue was crystallized from acetone and collected by filtration to obtain toluenesulfonate of the desired compound. The thus obtained salt was suspended in ethyl acetate (500 mL) and alkalified by adding saturated sodium bicarbonate aqueous solution (200 mL) to carry out separation of layers. The organic layer was washed with brine and dried over anhydrous sodium sulfate, and then the solvent was evaporated under a reduced pressure. The resulting residue was crystallized from ether and collected by filtration to obtain the title compound (5.9 g).

NMR (DMSO-d$_6$) δ [ppm]: 12.65 (1H, bs), 7.3–7.2 (7H, m), 3.83 (3H, s), 3.12 (4H, bs)

Reference Example 21

Synthesis of 6-methoxy-2-(2-phenylethyl) benzimidazole-4-carboxylic acid

4-Cyano-6-methoxy-2-(2-phenylethyl)benzimidazole (1.23 g) obtained in Reference Example 20 was added to 90% KOH aqueous solution (40 mL) and ethylene glycol (60 mL), and the mixture was heated under reflux for 8 hours. This was diluted with water and washed with ethyl acetate. The resulting water layer was adjusted to pH 6 with concentrated hydrochloric acid, and the thus precipitate was collected by filtration to obtain the title compound (1.27 g).

NMR (DMSO-d$_6$) δ [ppm]: 7.3–7.1 (7H, m), 3.81 (3H, s), 3.2–3.0 (4H, m)

Reference Example 22

Synthesis of 6-hydroxy-2-(2-phenylethyl) benzimidazole-4-carboxylic acid

4-Cyano-6-methoxy-2-(2-phenylethyl)benzimidazole (5.4 g) obtained in Reference Example 20 was dissolved in acetic acid (135 mL), and to the solution was added 48% hydrobromic acid (135 mL) and the mixture was heated under reflux for 8 hours. The reaction solution was poured into ice water (200 mL) and adjusted to pH 4 with 6 N sodium hydroxide. The thus precipitate was collected by filtration and washed with ethanol and ether to obtain the title compound as gray crystals (5.3 g).

NMR (DMSO-d$_6$) δ [ppm]: 11.95 (1H, bs), 9.28 (1H, bs), 7.3–7.1 (7H, m), 3.2–3.0 (4H, m)

Reference Example 23

Synthesis of 6-t-butyldimethylsilyloxy-2-(2-phenylethyl)benzimidazole-4-carboxylic acid Dry N,N-dimethylformamide (28 mL) was added to a mixture consisting of 6-hydroxy-2-(2-phenylethyl) benzimidazole-4-carboxylic acid (2.8 g) obtained in Reference Example 22, t-butyldimethylsilyl chloride (6.0 g) and N,N-dimethyl-4-aminopyridine (0.24 g). Triethylamine (5.5 mL) was added to the resulting mixture which was cooled in an ice bath, and then the mixture was stirred at room temperature for 2 hours. This was diluted with ice water (60 mL) and adjusted to pH 4 to 5 with 4 N hydrochloric acid. The thus precipitate was collected by filtration and washed with water. The thus obtained crystal was dissolved in tetrahydrofuran and dried over anhydrous sodium sulfate, and then the solvent was evaporated under a reduced pressure. The resulting residue was crystallized from hexane to obtain the title compound as crystal (3.4 g).

NMR (DMSO-d$_6$) δ [ppm]: 12.14 (1H, bs), 7.3–7.2 (7H, m), 3.2–3.0 (4H, m), 0.97 (9H, s), 0.19 (6H, s)

Reference Example 24

Synthesis of ethyl 3-(6-t-butyldimethylsilyloxy-2-(2-phenylethyl)benzimidazol-4-yl)-3-oxopropanoate Triethylamine (2.65 mL) and magnesium chloride (2.16 g) were added to dry acetonitrile (37.5 mL) suspension of potassium ethylmalonate (3.23 g), and the mixture was vigorously stirred at room temperature for 16 hours under in an atmosphere of argon. Next, a catalytically effective amount of N,N-dimethylaminopyridine and 1,1'-carbonyldiimidazole (1.35 g) were added to anhydrous tetrahydrofuran (30 mL) solution of 6-t-butyldimethylsilyloxy-2-(2-phenylethyl)benzimidazole-4-carboxylic acid (3.0 g) obtained in Reference Example 23, and the mixture was stirred for 1 hour under an atmosphere of argon. This was diluted to the previously prepared suspension of ethyl malonate magnesium salt while cooling in an ice bath, and the mixture was stirred at room temperature for 2 hours. This was diluted with ice water (50 mL) and, while cooling in an ice bath, adjusted to pH 1 with 4 N hydrochloric acid. While cooling in an ice bath, this was adjusted to pH 8 to 9 with saturated sodium bicarbonate aqueous solution and extracted with ethyl acetate. The organic layer was washed with brine and dried over anhydrous sodium sulfate, and then the solvent was evaporated under a reduced pressure. The resulting residue was purified by a silica gel column chromatography (eluent: hexane/ethyl acetate) and the desired fraction was concentrated to obtain the title compound as colorless oil (3.44 g).

Reference Example 25

Synthesis of ethyl 3-(6-t-butyldimethylsilyloxy-2-(2-phenylethyl)benzimidazol-4-yl)-3-hydroxypropanoate Ethyl 3-(6-t-butyldimethylsilyloxy-2-(2-phenylethyl) benzimidazol-4-yl)-3-oxopropanoate (2.0 g) obtained in Reference Example 24 was dissolved in anhydrous tetrahydrofuran (30 mL). Sodium borohydride (49 mg) was added to the solution which was cooled in an ice bath, and the mixture was stirred at room temperature for 3 hours. This was diluted with ice water, extracted with ethyl acetate and then washed with brine. The organic layer was dried over anhydrous sodium sulfate, and then the solvent was evaporated under a reduced pressure. The resulting residue was purified by a silica gel column chromatography (eluent: hexane/ethyl acetate). By concentrating the desired fraction, the title compound was obtained as colorless oil (700 mg).

NMR (CDCl$_3$) δ [ppm]: 9.46 (1H, bs), 7.3–7.0 (6H, m), 6.50 (1H, s), 5.34 (1H, bs), 4.22 (2H, q, J=7 Hz), 3.17 (4H, s), 2.76 (2H, d, J=6 Hz), 1.30 (3H, t, J=7 Hz)

Reference Example 26

Synthesis of ethyl 3-(6-t-butyldimethylsilyloxy-2-(2-phenylethyl)benzimidazol-4-yl)propenoate Ethyl 3-(6-t-butyldimethylsilyloxy-2-(2-phenylethyl) benzimidazol-4-yl)-3-hydroxypropanoate (530 mg) obtained in Reference Example 25 was dissolved in dichloromethane (8 mL). To this was added pyridine (0.14 mL) and then, while cooling in an ice bath, thionyl chloride (0.11 mL), and the mixture was stirred at the same temperature for 10 minutes. The reaction solution was diluted with ice water, adjusted to pH 7 to 8 with saturated sodium bicarbonate aqueous solution and then extracted with dichloromethane. The organic layer was washed with water and brine and dried over anhydrous sodium sulfate, and then the solvent was evaporated to obtain a chloro compound as oil. The thus obtained oily product was dissolved in dichloromethane (8 mL), and the solution which was cooled in an ice bath was mixed with 1,8-diazabicyclo[5.4.0]-7-undecene (0.17 mL) and stirred at the same temperature for 5 minutes. The reaction solution was mixed with ice water and extracted with dichloromethane. The organic layer was washed with water and brine and dried over anhydrous sodium sulfate and then the solvent was evaporated. The resulting residue was purified by a silica gel column chromatography (eluent: hexane/ethyl acetate). By concentrating the desired fraction, the title compound was obtained as oil (318 mg).

NMR (CDCl$_3$) δ [ppm]: 8.60 (1H, bs), 8.02 (1H, d, J=16 Hz), 7.4–7.2 (5H, m), 6.90 (1H, d, J=2 Hz), 6.79 (1H, d, J=2 Hz), 4.29 (2H, q, J=7 Hz), 3.3–3.2 (4H, m), 1.36 (3H, t, J=7 Hz), 0.99 (9H, s), 0.19 (6H, s)

Reference Example 27

Synthesis of ethyl 6-chloro-2-(2-phenylethyl) benzimidazole-4-carboxylate

According to Reference Example 2, using ethyl 2,3-diamino-5-chlorobenzoate (2.3 g), the title compound was obtained as crystal (3.10 g).

NMR (CDCl$_3$) δ [ppm]: 10.00 (1H, bs), 7.88 (1H, d, J=2 Hz), 7.83 (1H, d, J=2 Hz), 7.4–7.2 (5H, m), 4.43 (2H, q, J=7 Hz), 3.3–3.2 (4H, m), 1.43 (3H, t, J=7 Hz)

Reference Example 28

Synthesis of 6-chloro-2-(2-phenylethyl) benzimidazole-4-carboxylic acid

According to Reference Example 3, using ethyl 6-chloro-2-(2-phenylethyl)benzimidazole-4-carboxylate (3.09 g) obtained in Reference Example 27, the title compound was obtained as crystal (2.8 g).

NMR (DMSO-d$_6$) δ [ppm]: 8.02 (1H, d, J=2 Hz), 7.80 (1H, d, J=2 Hz), 7.3–7.2 (6H, m), 3.4–3.3 (2H, m), 3.3–3.1 (2H, m)

Reference Example 29

Synthesis of 4-hydroxymethyl-2-(2-phenylethyl) benzimidazole

While cooling in an ice bath, anhydrous tetrahydrofuran (63 mL) solution of ethyl 2-(2-phenylethyl)benzimidazole-4-carboxylate (20 g) obtained in Reference Example 2 was added dropwise to anhydrous tetrahydrofuran (63 mL) suspension of lithium aluminum hydride (5.2 g), and the mixture was stirred at room temperature for 15 minutes. After addition of ice water (200 mL) in small portions, ethyl acetate (400 mL) was added and insoluble material was removed by filtration. The resulting filtrate was separated, the organic layer was washed with water and brine and dried over anhydrous sodium sulfate, and then the solvent was evaporated under a reduced pressure. The resulting residue was crystallized from ether and collected by filtration to obtain the title compound as crystal (15.7 g).

NMR (DMSO-d$_6$) δ [ppm]: 12.22 (0.4H, bs), 12.11 (0.6H, bs), 7.5–7.0 (8H, m), 5.22 (0.6H, t, J=6 Hz), 5.08 (0.4H, t, J=6 Hz), 4.88 (0.8H, d, J=6 Hz), 4.74 (1.2 H, d, J=6 Hz), 3.2–3.1 (4H, m)

Reference Example 30

Synthesis of 4-formyl-2-(2-phenylethyl) benzimidazole

Anhydrous tetrahydrofuran (45 mL) was added to 4-hydroxymethyl-2-(2-phenylethyl)benzimidazole (5.0 g) obtained in Reference Example 29 and activated manganese dioxide (51.7 g), and the mixture was vigorously stirred at room temperature for 45 minutes. Insoluble material was removed by filtration and the resulting filtrate was concentrated under a reduced pressure. The thus obtained residue was purified by a column chromatography (eluent: hexane/ethyl acetate) and the desired fraction was concentrated under a reduced pressure. The resulting residue was crystallized from hexane and collected by filtration to obtain the title compound as crystal (12.2 g).

NMR (CDCl$_3$) δ [ppm]: 10.35 (1H, bs), 10.08 (1H, s), 8.01 (1H, d, J=8 Hz), 7.69 (1H, d, J=8 Hz), 7.4–7.2 (4H, m), 3.4–3.1 (4H, m)

Reference Example 31

Synthesis of methyl 5-fluoro-2-(2-phenylethyl)benzimidazole-4-carboxylate

According to Reference Example 2, using methyl 2,3-diamino-6-fluorobenzoate (3.9 g), the title compound was obtained as oil (2.53 g).

NMR (CDCl$_3$) δ [ppm]: 10.15 (1H, bs), 7.83 (1H, dd, J=9, 4 Hz), 7.4–7.2 (5H, m), 7.02 (1H, dd, J=12, 9 Hz), 3.98 (3H, s), 3.3–3.1 (4H, m)

Reference Example 32

Synthesis of 5-fluoro-2-(2-phenylethyl)benzimidazole-4-carboxylic acid

According to Reference Example 3, using methyl 5-fluoro-2-(2-phenylethyl)benzimidazole-4-carboxylate (2.53 g) obtained in Reference Example 31, the title compound was obtained as crystal (2.3 g).

NMR (DMSO-d$_6$) δ [ppm]: 7.77 (1H, dd, J=9, 4 Hz), 7.3–7.1 (5H, m), 7.08 (1H, dd, J=12, 9 Hz), 3.3–2.9 (4H, m)

Inventive Example 1

Synthesis of 3-(2-(2-phenylethyl)benzimidazol-4-yl)-3-oxopropanoic acid

4-Acetyl-2-(2-phenylethyl)benzimidazole (16 g) obtained in Reference Example 1 was dissolved in dimethyl sulfoxide (150 mL), and to the solution was added 18-crown-6 ether (16 g) and potassium carbonate (50 g). Carbon dioxide was bubbled for 6 hours into the resulting mixture which was stirred at room temperature. The reaction solution was poured into ice water (700 mL) and extracted with ethyl acetate. The water layer was adjusted to pH 5 to 6 by adding 6 N hydrochloric acid, and the precipitate was collected by filtration. The thus precipitate was dissolved in 1 N sodium hydroxide aqueous solution (150 mL), and the solution was washed with ether and then adjusted to pH 5 to 6 with 6 N hydrochloric acid. The resulting precipitate was collected by filtration to obtain the title compound (8.46 g).

NMR (DMSO-d$_6$) δ [ppm]: 12.71 (1H, bs), 7.9–7.8 (2H, m), 7.3–7.2 (6H, m), 4.23 (2H, s), 3.2–3.0 (4H, m)

IR (KBr) [cm$^{-1}$]: 3379, 1701, 1651, 1275, 1200, 1115

Melting point: 107.1–107.5° C.

Inventive Example 2

Synthesis of methyl 3-(2-(2-phenylethyl)benzimidazol-4-yl)-3-oxopropanoate 3-(2-(2-Phenylethyl)benzimidazol-4-yl)-3-oxopropanoic acid (4.0 g) obtained in Inventive Example 1 was suspended in methanol (25 mL) and tetrahydrofuran (100 mL), to which was subsequently added 2 M trimethylsilyldiazomethane-hexane solution (8.45 mL) in small portions. After stirring for 45 minutes at room temperature, the reaction solution was concentrated under a reduced pressure. The resulting residue was purified by a silica gel column chromatography (eluent: hexane/ethyl acetate) to obtain the title compound as slightly yellow crystal (3.45 g).

NMR (CDCl$_3$) δ [ppm]: 10.60 (1H, bs), 7.99 (1H, d, J=8 Hz), 7.71 (1H, d, J=8 Hz), 7.3–7.2 (6H, m), 4.11 (2H, s), 3.77 (3H, s), 3.3–3.2 (4H, m)

IR (KBr) [cm$^{-1}$]: 2939, 1740, 1674, 1518, 1271, 1109

Melting point: 56.8–59.1° C.

Inventive Example 3

Synthesis of ethyl 3-(2-(2-phenylethyl)benzimidazol-4-yl)-3-oxopropanoate 3-(2-(2-Phenylethyl)benzimidazol-4-yl)-3-oxopropanoic acid (6.0 g) obtained in Inventive Example 1 was added to 25% hydrochloric acid-ethanol (120 mL) and the mixture was stirred overnight at room temperature. The reaction solution was concentrated under a reduced pressure and adjusted to pH 7 to 8 by adding saturated sodium bicarbonate aqueous solution. This was extracted with ethyl acetate and washed with water and brine in that order. The organic layer was dried over anhydrous sodium sulfate and then concentrated under a reduced pressure. The resulting residue was crystallized from ether and hexane and collected by filtration to obtain the title compound as slightly reddish white crystal (4.3 g).

NMR (CDCl$_3$) δ [ppm]: 10.56 (1H, bs), 7.99 (1H, d, J=8 Hz), 7.72 (1H, d, J=8 Hz), 7.3–7.2 (6H, m), 4.24 (2H, q, J=7 Hz), 4.09 (2H, s), 3.3–3.2 (4H, m), 1.28 (3H, t, J=7 Hz)

IR (KBr) [cm$^{-1}$]: 2974, 1738, 1662, 1271, 1188, 1142

Melting point: 108.0–109.7° C.

Inventive Example 4

Synthesis of t-butyl 3-(2-(2-phenylethyl)benzimidazol-4-yl)-3-oxopropanoate

2-Chloro-1,3-dimethylimidazolinium hexafluorophosphate (1.9 g), t-butanol (0.50 g) and triethylamine (0.94 mL) were added to dichloromethane (20 mL), and the mixture was stirred at room temperature for 1 hour. 3-(2-(2-Phenylethyl)benzimidazol-4-yl)-3-oxopropanoic acid (0.60 g) obtained in Inventive Example 1 was dissolved in dichloromethane (20 mL) and added dropwise to the just described solution which was cooled in an ice bath. After stirring for 1 hour, the reaction solution was mixed with saturated sodium bicarbonate aqueous solution and dichloromethane to carry out separation of layers. The organic layer was washed with brine and dried over anhydrous sodium sulfate. After evaporation of the solvent under a reduced pressure, the resulting residue was purified by a silica gel column chromatography (eluent: hexane/ethyl acetate). The title compound was obtained as white crystal (0.26 g).

NMR (CDCl$_3$) δ [ppm]: 10.57 (1H, bs), 7.98 (1H, d, J=8 Hz), 7.71 (1H, d, J=7 Hz), 7.4–7.2 (6H, m), 4.00 (2H, s), 3.3–3.2 (4H, m), 1.46 (9H, s)

IR (KBr) [cm$^{-1}$]: 2974, 1749, 1728, 1670, 1524, 1375, 1273, 1111

Melting point: 121.5–123.0° C.

Inventive Example 5

Synthesis of methyl 3-(2-(2-phenylethyl)benzimidazol-4-yl)-3-hydroxypropanoate

Methyl 3-(2-(2-phenylethyl)benzimidazol-4-yl)-3-oxopropanoate (3.4 g) obtained in Inventive Example 2 was dissolved in anhydrous methanol (40 mL), and sodium borohydride (203 mg) was added in small portions to the resulting solution which was cooled in an ice bath. After stirring for 30 minutes in an ice bath and subsequent stirring for 40 minutes at room temperature, water (100 mL) was added to the reaction solution. This was extracted with ethyl acetate, and the organic layer was washed with brine. The organic layer was dried over anhydrous sodium sulfate and then the solvent was evaporated under a reduced pressure. The resulting residue was purified by a silica gel column chromatography (eluent: hexane/ethyl acetate). The desired fraction was concentrated, and the resulting residue was crystallized from hexane and ether and collected by filtration to obtain the title compound as crystal (2.72 g).

NMR (CDCl$_3$) δ [ppm]: 9.57 (1H, s), 7.64 (1H, d, J=8 Hz), 7.3–7.1 (6H, m), 6.93 (1H, d, J=7 Hz), 5.43 (1H, t, J=5 Hz), 3.87 (1H, s), 3.77 (3H, s), 3.3–3.2 (4H, m), 2.80 (2H, d, J=6 Hz)

IR (KBr) [cm$^{-1}$]: 3028, 1740, 1433, 1032, 1003, 756

Melting point: 156.4–157.4° C.

Inventive Example 6

Synthesis of ethyl 3-(2-(2-phenylethyl) benzimidazol-4-yl)3-hydroxypropanoate

Ethyl 3-(2-(2-phenylethyl)benzimidazol-4-yl)-3-oxopropanoate (0.20 g) obtained in Inventive Example 3 was dissolved in ethanol (5 mL), and to the solution was added sodium borohydride (8 mg) while cooling in an ice bath and then the mixture was stirred at room temperature for 30 minutes. The reaction solution was diluted with water, and ethanol was removed under a reduced pressure. The remaining aqueous solution was extracted with ethyl acetate. The organic layer was washed with brine and then dried over anhydrous sodium sulfate. After evaporation of the solvent under a reduced pressure, the resulting residue was purified by a silica gel column chromatography (eluent: hexane/ethyl acetate) to obtain the title compound as white crystal (0.13 g). NMR (CDCl$_3$) δ [ppm]: 9.60 (1H, s), 7.63 (1H, d, J=8 Hz), 7.3–7.1 (6H, m), 6.93 (1H, d, J=7 Hz), 5.43 (1H, t, J=6 Hz), 4.23 (2H, q, J=7 Hz), 3.95 (1H, s), 3.3–3.1 (4H, m), 2.78 (2H, d, J=6 Hz), 1.30 (3H, t, J=7 Hz)

IR (KBr) [cm$^{-1}$]: 3433, 3182, 1736, 1433, 1030, 748

Melting point: 125.8–127.7° C.

Inventive Example 7

Synthesis of 3-(2-(2-phenylethyl)benzimidazol-4-yl)-3-hydroxypropanoic Acid

Methyl 3-(2-(2-phenylethyl)benzimidazol-4-yl)-3-hydroxypropanoate (3.4 g) obtained in Inventive Example 5 was suspended in ethanol (5 mL), and to the suspension was added 1 N sodium hydroxide aqueous solution (10 mL). After stirring for 1 hour at room temperature, the reaction solution was concentrated under a reduced pressure. The thus obtained residue was diluted with water and extracted with ethyl acetate. The water layer was adjusted to pH 5 to 6 with 1 N hydrochloric acid, and the thus precipitate was collected by filtration to obtain the title compound as crystal (3.0 g).

NMR (CD$_3$OD) δ [ppm]: 7.44 (1H, d, J=8 Hz), 7.3–7.1 (7H, m), 5.51 (1H, t, J=7 Hz), 3.3–3.1 (4H, m), 2.77 (2H, d, J=7 Hz)

IR (KBr) [cm$^{-1}$]: 3396, 1635, 1581, 1412, 1389, 754

Melting point: 104.5–109.6° C.

Inventive Examples 8 and 9

Synthesis of (+)-3-(2-(2-phenylethyl)benzimidazol-4-yl)-3-hydroxypropanoic Acid (Inventive Example 8 and (-)-3-(2-(2-phenylethyl)benzimidazol-4-yl)-3-hydroxypropanoic Acid

Inventive Example 9

To a solution of methyl 3-(2-(2-phenylethyl) benzimidazol4-yl)-3-hydroxypropanoate (2.65 g) obtained in Inventive Example 5 in pyridine (25 mL) was added camphoric acid chloride (3.19 g) while cooling in an ice bath. After stirring for 1.5 hours in an ice bath and subsequent 6 hours of stirring at room temperature, this was mixed with ethyl acetate and 1 N hydrochloric acid. After separation of layers, the organic layer was washed with brine. The organic layer was dried over anhydrous sodium sulfate and then concentrated under a reduced pressure. The thus obtained residue was crystallized from hexane and ether and collected by filtration (4.0 g). The thus obtained crystal was separated (first fraction and second fraction) by a high performance liquid chromatography (CHIRALCEL OD™, manufactured by Daicel Chemical Industries, Ltd.; eluent: hexane/ethanol). The first fraction (0.80 g) was dissolved in methanol (80 mL) to which, cooled in an ice bath, was subsequently added 2 N sodium hydroxide (20 mL) in small portions. After stirring for 1 hour in an ice bath, the reaction solution was adjusted to pH 6 to 7 with 1 N hydrochloric acid and then extracted with ethyl acetate. The organic layer was combined, washed with brine and then dried over anhydrous sodium sulfate. After concentration of the organic layer under a reduced pressure, the resulting residue was purified by a silica gel column chromatography (eluent: dichloromethane/methanol) to obtain the intended (+)-3-(2-(2-phenylethyl)benzimidazol-4-yl)-3-hydroxypropanoic acid as crystal (0.23g). In the same manner, the intended (-)-3-(2-(2-phenylethyl)benzimidazol-4-yl)-3-hydroxypropanoic acid was obtained from the second fraction (0.24 g). (+)-3-(2-(2-Phenylethyl)benzimidazol-4-yl)-3-hydroxypropanoic acid (Inventive Example 8)

NMR (CD$_3$OD) δ [ppm]: 7.44 (1H, dd, J=8, 1 Hz), 7.3–7.1 (7H, m), 5.51 (1H, t, J=7 Hz), 3.3–3.1 (4H, m), 2.77 (2H, d, J=7 Hz)

IR (KBr) [cm$^{-1}$]: 1637, 1581, 1497, 1395, 750, 700

Melting point: 103.0–105.3° C.

Optical rotation: [α]$_D$=+12.74° (c 1.01, MeOH) (-)-3-(2-(2-Phenylethyl)benzimidazol-4-yl)-3-hydroxypropanoic acid (Inventive Example 9)

NMR (CD$_3$OD) δ [ppm]: 7.44 (1H, dd, J=8, 1 Hz), 7.3–7.1 (7H, m), 5.51 (1H, t, J=7 Hz), 3.3–3.1 (4H, m), 2.77 (2H, d, J=7 Hz)

IR (KBr) [cm$^{-1}$]: 1637, 1581, 1497, 1396, 750, 700

Melting point: 100.6–102.6° C.

Optical rotation: [α]$_D$=-12.03° (c 1.01, MeOH)

Inventive Example 10

Synthesis of ethyl 3-(1-methyl-2-(2-phenylethyl) benzimidazol-4-yl)-3-oxopropanoate To a solution of ethyl 3-(2-(2-phenylethyl)benzimidazol-4-yl)-3-oxopropanoate (3.2 g) obtained in Inventive Example 3 in acetone (150 mL) was added sodium bicarbonate (2.2 g) and dimethyl sulfate (2.3 mL) and the mixture was heated under reflux for 4 hours. After allowing the reaction solution to stand overnight, the insoluble material was removed by filtration and the resulting filtrate was concentrated under a reduced pressure. The thus obtained residue was dissolved in dichloromethane and washed with water and brine in that order. The organic layer was dried over anhydrous sodium sulfate, and the solvent was evaporated under a reduced pressure. The resulting residue was purified by a silica gel column chromatography (eluent: dichloromethane) to obtain the title compound as crystal (2.3 g).

NMR (CDCl$_3$) δ [ppm]: 7.95 (1H, dd, J=8, 1 Hz), 7.46 (1H, dd, J=8, 1 Hz), 7.3–7.2 (6H, m), 4.68 (2H, s), 4.22 (2H, q, J=7 Hz), 3.56 (3H, s), 3.3–3.1 (4H, m), 1.26 (3H, t, J=7 Hz)

IR (KBr) [cm$^{-1}$]: 2941, 1720, 1668, 1466, 1244, 1217, 1036, 756

Melting point: 143.2–145.5° C.

Inventive Example 11

Synthesis of ethyl 3-(1-methyl-2-(2-phenylethyl) benzimidazol-4-yl)-3-hydroxypropanoate To a suspension of ethyl 3-(1-methyl-2-(2-phenylethyl) benzimidazol-4-yl)-3-oxopropanoate (0.80 g) obtained in Inventive Example 10 in anhydrous methanol (16 mL), was added sodium borohydride in small portions which was cooled in an ice bath. After stirring for 20 minutes at room temperature, the reaction solution was poured into water and concentrated under a reduced pressure. The thus obtained residue was extracted with ethyl acetate, and the organic layer was washed with water and brine in that order. The organic layer was dried over anhydrous sodium sulfate and then the solvent was evaporated under a reduced pressure. The resulting residue was purified by a silica gel column chromatography (eluent: hexane/ethyl acetate) to obtain the title compound as white crystal (0.39 g).

NMR (CDCl$_3$) δ [ppm]: 7.3–7.1 (8H, m), 5.7–5.6 (1H, m), 5.27 (1H, d, J=7 Hz), 4.19 (2H, q, J=7 Hz), 3.53 (3H, s), 3.2–3.1 (4H, m), 3.1–2.9 (2H, m), 1.27 (3H, t, J=7 Hz)

IR (KBr) [cm$^{-1}$]: 3452, 1730, 1427, 1331, 1284, 1161, 756, 704

Melting point: 126.8–127.8° C.

Inventive Example 12

Synthesis of ethyl 3-(2-(2-phenylethyl) benzimidazol-4-yl)3-oxopropanoate (Compound of Inventive Example 3)

Potassium ethylmalonate (72.4 g) was suspended in anhydrous acetonitrile (1 L). Triethylamine (59.3 mL) and magnesium chloride (48.6 g) were added to the suspension and vigorously stirred at room temperature for 3 hours under an atmosphere of argon. Next, a catalytically effective amount of N,N-dimethylaminopyridine and 1,1'-carbonyldiimidazole (30.3 g) were added to anhydrous tetrahydrofuran (450 mL) suspension of 2-(2-phenylethyl) benzimidazole-4-carboxylic acid (45.3 g) obtained in Reference Example 3, and the mixture was stirred for 2 hours under an atmosphere of argon. The reaction solution was added to the previously prepared suspension of ethyl malonate magnesium salt while cooling in an ice bath, and the mixture was stirred at room temperature for 1 hour. This was adjusted to pH 1 with concentrated hydrochloric acid while cooling in an ice bath. At the same temperature, this was alkalified with saturated sodium bicarbonate aqueous solution and extracted with ethyl acetate. The organic layer was washed with water and brine and dried over anhydrous sodium sulfate, and then the solvent was evaporated under a reduced pressure. The resulting residue was crystallized from hexane and collected by filtration to obtain the title compound as crystal (43 g). Respective spectra and melting point of the thus obtained crystal coincided with the data obtained in Inventive Example 3.

Inventive Example 13

Synthesis of ethyl 3-(2-(2-phenylethyl) benzimidazol-4-yl)-3-acetyloxypropionate Ethyl 3-(2-(2-phenylethyl)benzimidazol-4-yl)-3-hydroxypropionate (3.0 g) obtained in Inventive Example 6 was suspended in dichloromethane (25 mL). While cooling in an ice bath, pyridine (2.2 mL) and acetic anhydride (1.7 mL) were added to the suspension and stirred at the same temperature for 40 minutes. The reaction solution was diluted with dichloromethane, washed with saturated sodium bicarbonate aqueous solution, water and brine and dried over anhydrous sodium sulfate, and then the solvent was evaporated. The resulting residue was purified by a silica gel column chromatography (eluent: hexane/ethyl acetate) and the desired fraction was concentrated to obtain the title compound as colorless crystal (1.14 g).

Inventive Example 14

Synthesis of ethyl 3-(2-benzylbenzimidazol-3-yl)-3-oxopropanoate

According to Inventive Example 3, using 2-benzylbenzimidazole-3-oxopropanoic acid (1.3 g) obtained in Reference Example 5, the title compound was obtained as colorless crystal (1.0 g).

Inventive Example 15

Synthesis of ethyl 3-(2-benzylbenzimidazol-3-yl)-3-hydroxypropanoate

According to Inventive Example 6, using ethyl 3-(2-benzylbenzimidazol-3-yl)-3-oxopropanoate (0.68 g) obtained in Inventive Example 14, the title compound was obtained as colorless crystals (0.38 g).

Inventive Example 16

Synthesis of ethyl 3-(2-phenylbenzimidazol-3-yl)-3-oxopropanoate

According to Inventive Example 12, using 2-phenylbenzimidazole-3-carboxylic acid (1.46 g) obtained in Reference Example 7, the title compound was obtained as oil (1.28 g).

Inventive Example 17

Synthesis of ethyl 3-(2-phenylbenzimidazol-3-yl)-3-hydroxypropanoate

According to Inventive Example 6, using ethyl 3-(2-phenylbenzimidazol-3-yl)-3-oxopropanoate (0.80 g) obtained in Inventive Example 16, the title compound was obtained as colorless crystal (0.44 g).

Inventive Example 18

Synthesis of ethyl 3-(2-(2-(4-hydroxyphenyl)ethyl) benzimidazol-4-yl)-3-oxopropanoate Ethyl 3-(2-(2-(4-benzyloxyphenyl)ethyl)benzimidazol-4-yl)-3-oxopropanoate (1.8 g) obtained in Reference Example 10 was dissolved in ethanol (10 mL) and dichloromethane (5 mL), and to the solution was added with acetic acid (1 mL) and 10% palladium/carbon (0.09 g) and the mixture was stirred overnight at room temperature under an atmosphere of hydrogen. After removal of the catalyst by filtration, the resulting filtrate was concentrated under a reduced pressure. The thus obtained residue was diluted with water, adjusted to pH 8 with saturated sodium bicarbonate aqueous solution and then extracted with ethyl acetate. The organic layer was washed with water and brine in that order and then dried over anhydrous sodium sulfate. After evaporation of the solvent under a reduced pressure, the resulting residue was purified by a silica gel column chromatography (eluent: hexane/ethyl acetate) to obtain the title compound as crystal (1.0 g).

Inventive Example 19

Synthesis of ethyl 3-(2-(2-(4-hydroxyphenyl)ethyl) benzimidazol-4-yl)-3-hydroxypropanoate According to Inventive Example 6, using ethyl 3-(2-(2-(4-benzyloxyphenyl)ethyl)benzimidazol-4-yl)-3-oxopropanoate (0.75 g) obtained in Inventive Example 18, the title compound was obtained as colorless crystal (0.50 g).

Inventive Example 20

Synthesis of ethyl 3-(2-(2-phenylethyl) benzimidazol-4-yl)-3-aminopropanoate dihydrochloride To a suspension of ethyl 3-(2-(2-phenylethyl) benzimidazol-4-yl)-3-oxopropanoate (3.5 g) obtained in Inventive Example 12 and O-benzylhydroxylamine hydrochloride (4.15 mL) in methanol was added pyridine (2.1 mL), and the mixture was stirred at room temperature for 16 hours. The mixture was diluted with water and extracted with ethyl acetate. The organic layer was washed with water and brine and dried over anhydrous sodium sulfate, and then the solvent was evaporated under a reduced pressure. The thus obtained residue was crystallized from ether and hexane and collected by filtration to obtain a benzyloxime compound as colorless crystals. The thus obtained crystal was dissolved in methanol (100 mL) and acetic acid (100 mL). 10% Palladium/carbon (2.5 g) was added to the resulting solution and the mixture was stirred for 16 hours under an atmosphere of hydrogen. The catalyst was removed by filtration, and the resulting filtrate was alkalified with saturated sodium bicarbonate aqueous solution and then extracted with dichloromethane. The organic layer was washed with brine and dried over anhydrous sodium sulfate, and then the solvent was evaporated. Ethyl 3-(2-(2-phenylethyl)benzimidazol-4-yl)-3-aminopropanoate was obtained as the resulting residue of oil (3.0 g). The thus obtained oil was dissolved in hydrochloric acid/ethanol and concentrated. This was crystallized from ether and collected by filtration to obtain the title compound.

Inventive Example 21

Synthesis of ethyl 3-(2-(2-phenylethyl) benzimidazol-4-yl)3-acetylaminopropanoate To a solution of ethyl 3-(2-(2-phenylethyl)benzimidazol-4-yl)-3-aminopropanoate (400 mg) obtained in Inventive Example 20 in dichloromethane (50 mL) was added pyridine (0.096 mL), cooled in an ice bath and then added acetyl chloride (0.084 mL). The mixture was diluted with water and extracted with dichloromethane. The organic layer was washed with brine and dried with anhydrous sodium sulfate, and then the solvent was evaporated. The resulting residue was purified by a silica gel column chromatography (eluent: hexane/ethyl acetate) and the desired fraction was concentrated to obtain the title compound as crystal (330 mg).

Inventive Example 22

Synthesis of ethyl 3-(2-(2-phenylethyl) benzimidazol-4-yl)3-benzenesulfonylaminopropanoate hydrochloride According to Inventive Example 21, ethyl 3-(2-(2-phenylethyl)benzimidazol-4-yl)-3-aminopropanoate (400 mg) obtained in Inventive Example 20 and benzenesulfonyl chloride (0.15 mL) were reacted, and the thus obtained oil was dissolved in hydrochloric acid/ethanol. The solvent was evaporated under a reduced pressure, and the resulting residue was crystallized from ether and collected by filtration to obtain the title compound as crystal (110 mg).

Inventive Example 23

Synthesis of ethyl 3-(2-(2-phenylethyl) benzimidazol-4-yl)3-(2-methoxybenzoylamino) propanoate According to Inventive Example 21, using ethyl 3-(2-(2-phenylethyl)benzimidazol-4-yl)-3-aminopropanoate (500 mg) obtained in Reference Example 20 and 2-methoxybenzoyl chloride (0.22 mL), the title compound was obtained (530 mg).

Inventive Example 24

Synthesis of 3-(2-(2-phenylethyl)benzimidazol-4-yl)-3-oxopropanoic acid dimethylamide Pyridine (0.365 mL) and magnesium chloride (215 mg) were added to dry dichloromethane (2.2 mL) solution of N,N-dimethylacetamide, and the mixture was vigorously stirred at room temperature for 1.5 hours under an atmosphere of argon. Next, a catalytically effective amount of N,N-dimethylaminopyridine and 1,1'-carbonyldiimidazole (134 mg) were added to anhydrous tetrahydrofuran (2 mL) suspension of 2-(2-phenylethyl)benzimidazole-4-carboxylic acid (0.2 g) obtained in Reference Example 3, and the mixture was stirred for 1.5 hours under an atmosphere of argon. The reaction solution was added to the previously prepared N,N-dimethylacetamide suspension of magnesium salt while cooling in an ice bath, and the mixture was stirred at room temperature for 2 hours. This was diluted with ice water and adjusted to pH 1 with 1 N hydrochloric acid while cooling in an ice bath. At the same temperature, this was neutralized with saturated sodium bicarbonate aqueous solution and extracted with ethyl acetate. The organic layer was washed with brine and dried over anhydrous sodium sulfate, and then the solvent was evaporated under a reduced pressure. The resulting residue was purified by a silica gel column chromatography (eluent: hexane/ethyl acetate) and the desired fraction was concentrated to obtain the title compound as colorless crystal (43 mg).

Inventive Example 25

Synthesis of 3-(2-(2-phenylethyl)benzimidazol-4-yl)-3-oxopropionitrile

Triethylamine (5.2 mL) and magnesium chloride (4.3 g) were added to dry acetonitrile (30 mL) solution of cyanoacetic acid (1.6 g), and the mixture was vigorously stirred at room temperature for 23 hours under an atmosphere of argon. Next, a catalytically effective amount of N,N-dimethylaminopyridine and 1,1'-carbonyldiimidazole (1.34 g) were added to anhydrous tetrahydrofuran (20 mL) suspension of 2-(2-phenylethyl)benzimidazole-4-carboxylic acid (2.0 g) obtained in Reference Example 3, and the mixture was stirred for 2.5 hours under an atmosphere of argon. The reaction solution was added to the previously prepared cyanoacetic acid suspension of magnesium salt while cooling in an ice bath, and the mixture was stirred at room temperature for 2 hours. The reaction mixture was diluted with ice water (30 mL) and, at the same temperature, adjusted to pH 1 with 4 N hydrochloric acid. At the same temperature, this was adjusted to pH 9 with saturated sodium bicarbonate aqueous solution and extracted with ethyl acetate. The organic layer was washed with water and brine and dried over anhydrous sodium sulfate, and then the solvent was evaporated under a reduced pressure. The resulting residue was purified by a silica gel column chromatography (eluent: hexane/ethyl acetate) and the desired fraction was concentrated to obtain the title compound as colorless crystal (1.03 g).

Inventive Example 26

Synthesis of 3-(2-(2-phenylethyl)benzimidazol-4-yl)-3-hydroxypropionitrile

To a suspension of 3-(2-(2-Phenylethyl)benzimidazol-4-yl)3-oxopropionitrile (400 mg) obtained in Inventive Example 25 in ethanol (4.8 mL), while cooling in an ice bath, was added sodium borohydride (26 mg), and the mixture was stirred at the same temperature for 1 hour. The reaction solution was poured into ice water (20 mL) and extracted with ethyl acetate. The organic layer was washed with water and brine and dried over anhydrous sodium sulfate, and then the solvent was evaporated under a reduced pressure. The resulting residue was crystallized from ether and collected by filtration to obtain the title compound as crystal (297 mg)

Inventive Example 27

Synthesis of 3-(2-(2-phenylethyl)benzimidazol-4-yl)-3-hydroxypropanoic acid amide maleate Ethyl 3-(2-(2-phenylethyl)benzimidazol-4-yl)-3-hydroxypropanoate (100 mg) obtained in Inventive Example 6 was dissolved in 20% ammonia/methanol (5 mL), and the solution was stirred at room temperature for 1 hour. Concentrated aqueous ammonia (5 mL) was added to the mixture and the mixture was stirred at room temperature for 19 hours. Methanol was evaporated, and the thus obtained residue was extracted with ethyl acetate. After drying over anhydrous sodium sulfate, the solvent was evaporated under a reduced pressure. The thus obtained residue was dissolved in ethyl acetate/ethanol and maleic acid (24 mg) was added to the mixture. After evaporation of the solvent under a reduced pressure, the resulting residue was crystallized from ether and collected by filtration to obtain the title compound as colorless crystal (68 mg).

Inventive Example 28

Synthesis of cis-3-(2-(2-phenylethyl)benzimidazol-4-yl)-2-propenoic acid 2-(2-Phenylethyl)-4H-imidazo[4,5,1-i,j]-quinolin-4-on (1.0 g) obtained in Reference Example 13 was dissolved in tetrahydrofuran (30 mL) and methanol (5 mL), and 10% sodium hydroxide aqueous solution (15 mL) was added in small portions to the solution which was cooled in an ice bath. After stirring for 2 hours at room temperature, the reaction solution was diluted with water (20 mL). This was adjusted to pH 2 using 1 N hydrochloric acid, and the thus precipitate was collected by filtration to obtain the title compound as colorless crystal (0.84 g).

Inventive Example 29

Synthesis of 3-(2-(2-phenylethyl)benzimidazol-4-yl)-propanoic acid

To a solution of cis-3-(2-(2-Phenylethyl)benzimidazol-4-yl)-2-propenoic acid (1.0 g) obtained in Inventive Example 28 in methanol (20 mL) was added 10% palladium/carbon (100 mg) and the mixture was stirred at room temperature for 2 hours under an atmosphere of hydrogen. The catalyst was removed by filtration and the resulting filtrate was concentrated. The resulting residue was crystallized from ethyl acetate and hexane and collected by filtration to obtain the title compound as colorless crystal (0.8 g).

Inventive Example 30

Synthesis of ethyl trans-3-(2-(2-phenylethyl) benzimidazol-4-yl)propenoate

To a solution of ethyl 3-(2-(2-phenylethyl)benzimidazol-4-yl)-3-hydroxypropionate (3.0 g) obtained in Inventive Example 6 in dichloromethane (50 mL) was added pyridine (1.08 mL). While cooling in an ice bath, thionyl chloride (0.87 mL) was added to the mixture, and the mixture was stirred at the same temperature for 5 minutes. The reaction solution was diluted with water, alkalified with saturated sodium bicarbonate aqueous solution and then extracted with dichloromethane. The organic layer was washed with water and brine and dried over anhydrous sodium sulfate, and then the solvent was evaporated under a reduced pressure. The thus obtained oil was dissolved in dichloromethane (50 mL). While cooling in an ice bath, this was mixed with 1,8-diazabicyclo[5.4.0]-7-undecene (1.34 mL) was added to the mixture and the mixture was stirred at the same temperature for 5 minutes. The reaction solution was diluted with dichloromethane, washed with water and brine and dried over anhydrous sodium sulfate, and then the solvent was evaporated under a reduced pressure. The resulting residue was purified by a silica gel column chromatography (eluent: hexane/ethyl acetate) and the title fraction was concentrated to obtain the desired compound as colorless crystal (2.0 g).

Inventive Example 31

Synthesis of 3-(2-(2-phenylethyl)benzimidazol-4-yl)-3-hydroxypropanoylglycine ethyl ester 3-(2-(2-Phenylethyl)benzimidazol-4-yl)-3-hydroxypropanoate (310 mg) obtained in Inventive Example 7, benzotriazol-1-yloxytris(dimethylamino)phosphonium hexafluorophosphate (490 mg) and ethylglycine hydrochloride (160 mg) were suspended in tetrahydrofuran (3 mL). While cooling in an ice bath, triethylamine (0.31 mL) was added to the mixture and the mixture was stirred at room temperature for 1 hour. The reaction solution was diluted with water (5 mL) and extracted with ethyl acetate. The organic layer was washed with water and brine and dried over anhydrous sodium sulfate, and then the solvent was evaporated under a reduced pressure. The resulting residue was purified by a silica gel column chromatography (eluent: hexane/ethyl acetate). The desired fraction was concentrated, and the resulting residue was crystallized from ether and collected by filtration to obtain the title compound as colorless crystal (170 mg).

Inventive Example 32

Synthesis of 3-(2-(2-phenylethyl)benzimidazol-4-yl)-3-hydroxypropanoyl(L)-phenylalanine ethyl ester 3-(2-(2-Phenylethyl)benzimidazol-4-yl)-3-hydroxypropanoate (310 mg) obtained in Inventive Example 7, benzotriazol-1-yloxytris(dimethylamino)phosphonium hexafluorophosphate (490 mg) and ethyl(L)-phenylalanine hydrochloride (252 mg) were dissolved in N,N-dimethylformamide (3 mL). While cooling in an ice bath, triethylamine (0.31 mL) was added to the mixture and the mixture was stirred at 70 to 80° C. for 2 hours. The reaction solution was diluted with water and extracted with ethyl acetate. The organic layer was washed with saturated sodium bicarbonate aqueous solution, 5% citric acid aqueous solution and brine and dried over anhydrous sodium sulfate, and then the solvent was evaporated under a reduced pressure. The resulting residue was purified by a silica gel column chromatography (eluent: hexane/ethyl acetate). The desired fraction was concentrated, and the resulting residue was crystallized from ethyl acetate/ether and collected by filtration to obtain the title compound as crystal (200 mg).

Inventive Example 33

Synthesis of 3-(2-(2-phenylethyl)benzimidazol-4-yl)-3-hydroxypropanoyl(D)-phenylalanine ethyl ester 3-(2-(2-Phenylethyl)benzimidazol-4-yl)-3-hydroxypropanoate (310 mg) obtained in Inventive Example 7, benzotriazol-1-yloxytris(dimethylamino)phosphonium hexafluorophosphate (490 mg) and ethyl(D)-phenylalanine hydrochloride (252 mg) were dissolved in N,N-dimethylformamide (3 mL). While cooling in an ice bath, triethylamine (0.31 mL) was added to the mixture and the mixture was stirred at 70 to 80° C. for 2 hours. The reaction solution was diluted with water and extracted with ethyl acetate. The organic layer was washed with saturated sodium bicarbonate aqueous solution, citric acid aqueous solution and brine and dried over anhydrous sodium sulfate, and then the solvent was evaporated under a reduced pressure. The resulting residue was purified by a silica gel column chromatography (eluent: hexane/ethyl acetate). The desired fraction was concentrated and the resulting residue was crystallized from ethyl acetate/ether. By recrystallizing from ethanol/ethyl acetate and collecting by filtration, the title compound was obtained as colorless crystal (340 mg).

Inventive Example 34

Synthesis of dimethyl 3-((2-(2-phenylethyl)benzimidazol-4-yl)methoxymethyl)phthalate To a solution of dimethyl (1-(4-methoxybenzyl)-3-(2-(2-phenylethyl)benzimidazol-4-yl)methoxymethyl)phthalate (970 mg) obtained in Reference Example 16 in acetonitrile:water=9:1 (10 mL) was added ammonium cerium nitrate (5.0 g), and the mixture was stirred at room temperature for 16 hours. The reaction solution was diluted with water and extracted with ethyl acetate. The organic layer was washed with brine and dried over anhydrous sodium sulfate, and then the solvent was evaporated under a reduced pressure. The resulting residue was purified by a silica gel column chromatography (eluent: hexane/ethyl acetate) and the desired fraction was concentrated under a reduced pressure to obtain the title compound as oil (630 mg).

Inventive Example 35

Synthesis of 3-((2-(2-phenylethyl)benzimidazol-4-yl)methoxymethyl)phthalic acid

To a solution of dimethyl 3-((2-(2-phenylethyl)benzimidazol-4-yl)methoxymethyl)phthalate (1.2 g) obtained in Inventive Example 34 in methanol was added water (10 mL) solution of potassium hydroxide (0.6 g), and the mixture was heated under reflux for 13 hours. Methanol was evaporated under a reduced pressure and the thus obtained residue was adjusted to pH 5 to 6 with 1 N hydrochloric acid. The thus precipitate was collected by filtration and washed with ethanol and ether to obtain the title compound as colorless crystal (730 mg).

Inventive Example 36

Synthesis of ethyl 2-((2-(2-phenylethyl)benzimidazol-4-yl)methoxymethyl)benzoate According to Reference Example 16 and Inventive Example 34, using 4-hydroxymethyl-1-p-methoxybenzyl-2-(2-phenylethyl)benzimidazole (1.0 g) obtained in Reference Example 15 and ethyl 2-bromomethylbenzoate (550 mg) the title compound was obtained as oil (470 mg).

Inventive Example 37

Synthesis of 2-((2-(2-phenylethyl)benzimidazol-4-yl)methoxymethyl)benzoic acid

According to Inventive Example 35, using ethyl 2-((2-(2-phenylethyl)benzimidazol-4-yl)methoxymethyl)benzoate (350 mg) obtained in Inventive Example 36, the title compound was obtained as crystal (280 mg).

Inventive Example 38

Synthesis of ethyl 4-((2-(2-phenylethyl)benzimidazol-4-)methoxymethyl)benzoate

According to Reference Example 16 and Inventive Example 34, using 4-hydroxymethyl-1-(4-methoxybenzyl)-2-(2-phenylethyl)benzimidazole (2.01 g) obtained in Reference Example 15 and ethyl 2-bromomethylbenzoate (1.36 g), the reaction was carried out. The thus obtained oil was mixed with 10% hydrochloric acid/ether and crystallized with ether to obtain the title compound (450 mg).

Inventive Example 39

Synthesis of methyl 2-((2-(2-phenylethyl)benzimidazol-4-)methoxymethyl)benzoate hydrochloride According to Reference Example 16 and Inventive Example 34, using 4-hydroxymethyl-1-(4-methoxybenzyl)-2-(2-phenylethyl)benzimidazole (2.54 g) obtained in Reference Example 15 and methyl 3-bromomethylbenzoate (1.78 g), the reaction was carried out. The thus obtained oil was dissolved in 10% hydrochloric acid/methanol, the solvent was evaporated under a reduced pressure and then the resulting residue was crystallized from ether to obtain the title compound as crystal (468 mg).

Inventive Example 40

Synthesis of ethyl 3-(6-methoxy-2-(2-phenylethyl)benzimidazol-4-yl)-3-oxopropanoate Triethylamine (1.3 mL) and magnesium chloride (1.06 g) were added to anhydrous acetonitrile (15 mL) suspension of potassium ethylmalonate (1.58 g), and the mixture was vigorously stirred at room temperature for 18 hours under an atmosphere of argon. Next, a catalytically effective amount of N,N-dimethylaminopyridine and N,N-carbonyldiimidazole (663 mg) were added to anhydrous tetrahydrofuran (12 mL) suspension of 6-methoxy-2-(2-phenylethyl)benzimidazole-4-carboxylic acid (1.1 g) obtained in Reference Example 21, and the mixture was stirred for 2 hours under an atmosphere of argon. The reaction solution was added to the previously prepared suspension of ethyl malonate magnesium salt while cooling in an ice bath, and the mixture was stirred at room temperature for 2 hours. While cooling in an ice bath, this was diluted with water and adjusted to pH 1 with 4 N hydrochloric acid. At the same temperature, this was adjusted to pH 7 to 8 with saturated sodium bicarbonate aqueous solution and extracted with ethyl acetate. The organic layer was washed with brine and dried over anhydrous sodium sulfate, and then the solvent was evaporated under a reduced pressure. The resulting residue was purified by a silica gel column chromatography (eluent: hexane/ethyl acetate) and the desired fraction was concentrated to obtain the title compound as crystal (620 mg).

Inventive Example 41

Synthesis of ethyl 3-(6-methoxy-2-(2-phenylethyl)benzimidazol-4-yl)-3-hydroxypropanoate To a solution of ethyl 3-(6-methoxy-2-(2-phenylethyl)benzimidazol-4-yl)-3-oxopropanoate (400 mg) obtained in Inventive Example 40 in anhydrous tetrahydrofuran (16 mL), while cooling in an ice bath, was added sodium borohydride (12.4 mg) and the mixture was stirred at room temperature for 3.5 hours. The reaction solution was diluted with ice water, extracted with ethyl acetate and then washed with brine. After drying the organic layer over anhydrous sodium sulfate, the solvent was evaporated under a reduced pressure. The resulting residue was purified by a silica gel column chromatography (eluent: hexane/ethyl acetate). Thereafter, the desired fraction was concentrated to obtain the title compound as colorless crystal (110 mg).

Inventive Example 42

Synthesis of ethyl 3-(6-hydroxy-2-(2-phenylethyl)benzimidazol-4-yl)-3-oxopropanoate Ethyl 3-(6-t-butyldimethylsilyloxy-2-(2-phenylethyl)benzimidazol-4-yl)-3-oxopropanoate (3.03 g) obtained in Reference Example 24 was dissolved in anhydrous tetrahydrofuran (31 mL). At a temperature of −40° C., to this was added dropwise 1.0 M tetrahydrofuran solution (7.1 mL) of tetra(n-butyl)ammonium fluoride. After stirring for 30 minutes at the same temperature, this was mixed with ice water (20 mL) and adjusted to pH 5 with 4 N hydrochloric acid. This was extracted with ethyl acetate and washed with water and brine. After drying over anhydrous sodium sulfate, the solvent was evaporated. The resulting residue was purified by a silica gel column chromatography (eluent: hexane/ethyl acetate) and the desired fraction was concentrated. The resulting residue was crystallized from ethyl acetate/ether and collected by filtration to obtain the title compound as crystal (1.71 g).

Inventive Example 43

Synthesis of ethyl 3-(6-hydroxy-2-(2-phenylethyl)benzimidazol-4-yl)-3-hydroxypropanoate hydrochloride To a suspension of ethyl 3-(6-hydroxy-2-(2-phenylethyl)benzimidazol-4-yl)-3-oxopropanoate (800 mg) obtained in Inventive Example 42 in anhydrous tetrahydrofuran (16 mL), while cooling in an ice bath, was added sodium borohydride (26 mg) and the mixture was stirred at room temperature for 3 hours. The reaction solution was diluted with ice water (10 mL) and adjusted to pH 1 with 4 N hydrochloric acid. This was neutralized with saturated sodium bicarbonate aqueous solution, extracted with ethyl acetate and then washed with brine. The organic layer was dried over anhydrous sodium sulfate and then the solvent was evaporated under a reduced pressure. The resulting residue was purified by a silica gel column chromatography (eluent: hexane/ethyl acetate). The desired fraction was concentrated and dissolved in hydrochloric acid/ethanol. The solvent was replaced by ether and then ether was evaporated to obtain the title compound as colorless crystal (350 mg).

Inventive Example 44

Synthesis of 1,3-dihydroxypropyl-6-hydroxy-2-(2-phenylethyl)benzimidazole

To a suspension of Ethyl 3-(6-hydroxy-2-(2-phenylethyl)benzimidazol-4-yl)-3-oxopropanoate (500 mg) obtained in Inventive Example 42 in anhydrous ethanol (10 mL), while cooling in an ice bath, was added sodium borohydride (81 mg), and the mixture was stirred at room temperature for 2 hours. The reaction solution was diluted with ice water (20 mL) and extracted with ethyl acetate. The organic layer was washed with water and brine and dried over anhydrous sodium sulfate, and then the solvent was evaporated under a reduced pressure. The resulting residue was crystallized from ether to obtain the desired compound as colorless crystal (424 mg).

Inventive Example 45

Synthesis of 1,3-dihydroxypropyl-2-(2-phenylethyl)benzimidazole

Using ethyl 3-(2-(2-phenylethyl)benzimidazol-4-yl)-3-oxopropanoate obtained in Inventive Example 12, the procedure of Inventive Example 44 was repeated to obtain the title compound.

Inventive Example 46

Synthesis of ethyl 3-(6-hydroxy-2-(2-phenylethyl)benzimidazol-4-yl)propenoate

To a solution of ethyl 3-(6-t-butyldimethylsilyloxy-2-(2-phenylethyl)benzimidazol-4-yl)propenoate (318 mg) obtained in Reference Example 26 in anhydrous tetrahydrofuran (4 mL), while cooling in an ice bath, was added 1.0 M tetrahydrofuran solution (0.85 mL) of tetra-(n-butyl) ammonium fluoride, and the mixture was stirred at the same temperature for 10 minutes. The reaction solution was diluted with water and adjusted to pH 5 with 4 N hydrochloric acid. This was adjusted to pH 7 to 8 with saturated sodium bicarbonate aqueous solution and extracted with ethyl acetate. The organic layer was washed with water and brine and dried over anhydrous sodium sulfate, and then the solvent was evaporated under a reduced pressure. The resulting residue was crystallized from hexane and collected by filtration to obtain the title compound as crystal (200 mg).

Inventive Example 47

Synthesis of ethyl 3-(6-chloro-2-(2-phenylethyl) benzimidazol-4-yl)-3-oxopropanoate According to Inventive Example 12, using 6-chloro-2-(2-phenylethyl)benzimidazole-4-carboxylic acid (2.8 g) obtained in Reference Example 28, the title compound was obtained as crystal (2.37 g).

Inventive Example 48

Synthesis of ethyl 3-(6-chloro-2-(2-phenylethyl) benzimidazol-4-yl)-3-hydroxopropanoate According to Inventive Example 6, using ethyl 3-(6-chloro-2-(2-phenylethyl)benzimidazol-4-yl)-3-oxopropanoate (1.5 g) obtained in Inventive Example 47, the title compound was obtained as crystal (620 mg).

Inventive Example 49

Synthesis of 4-(3-(imidazol-2-yl)-2-propenoyl)-2-(2-phenylethyl)benzimidazole

Ethanol (15 mL) was added to 4-acetyl-2-(2-phenylethyl) benzimidazole (1 g) obtained in Reference Example 1 and 2-imidazolecarboxyaldehyde (304 mg). Sodium hydroxide (405 mg) was added to the mixture and the mixture was stirred overnight at room temperature. The reaction solution was poured into ice water, adjusted to pH 8 with 4 N hydrochloric acid and then extracted with ethyl acetate. The organic layer was washed with water and brine in that order and then dried over anhydrous sodium sulfate. After evaporation of the solvent under a reduced pressure, the resulting residue was purified by a silica gel column chromatography (eluent: hexane/ethyl acetate) to obtain the title compound (0.35 g).

Inventive Example 50

Synthesis of 2-(2-(2-phenylethyl)benzimidazol-4-yl)-2-hydroxyacetic acid

To a solution of 4-formyl-2-(2-phenylethyl) benzimidazole (1.0 g) obtained in Reference Example 30 in dry dichloromethane was added trimethylsilyl cyanide (0.64 mL) and cerium chloride (100 mg), and the mixture was stirred at room temperature for 16 hours. The insoluble material was removed by filtration and the resulting filtrate was concentrated under a reduced pressure. To the solution of thus obtained residue was dissolved in ethanol (1.7 mL) was added concentrated hydrochloric acid (3.3 mL), and the mixture was heated under reflux for 13 hours. The reaction solution was adjusted to pH 5 with 1 N sodium hydroxide. The supernatant was discarded by decantation, and the resulting residue was crystallized by adding ether/methanol and collected by filtration to obtain the title compound as colorless crystal (510 mg).

Inventive Example 51

Synthesis of ethyl 2-(2-(2-phenylethyl) benzimidazol-4-yl)-2-hydroxyacetate

To the suspension of 2-(2-(2-Phenylethyl)benzimidazol-4-)-2-hydroxyacetic acid (400 mg) obtained in Inventive Example 50 in ethanol (4 mL), while cooling in an ice bath, was added 20% hydrochloric acid/ethanol (4 mL), and the mixture was stirred at room temperature for 40 hours. The reaction solution was poured into ice water (20 mL) and adjusted to pH 9 with saturated sodium bicarbonate aqueous solution. Thus precipitate was collected by filtration and the resulting filtrate was extracted with ethyl acetate. The organic layer was combined with the collected crystals and dissolved by adding dichloromethane/ethanol, and then the solution was washed with brine. The organic layer was dried over anhydrous sodium sulfate, and the solvent was evaporated under a reduced pressure. The resulting residue was crystallized from ethanol/ethyl acetate and collected by filtration to obtain the title compound as crystal (341 mg).

Inventive Example 52

Synthesis of ethyl 3-(5-fluoro-2-(2-phenylethyl) benzimidazol-4-yl)-3-oxopropanoate According to Inventive Example 12, using 5-fluoro-2-(2-phenylethyl)benzimidazole-4-carboxylic acid (1.7 g) obtained in Reference Example 32, the title compound was obtained as crystal (1.78 g).

Inventive Example 53

Synthesis of ethyl 3-(5-fluoro-2-(2-phenylethyl) benzimidazol-4-yl)-3-hydroxypropanoate According to Inventive Example 6, using ethyl 3-(5-fluoro-2-(2-phenylethyl)benzimidazol-4-yl)-3-oxopropanoate (1.2 g) obtained in Inventive Example 52, the title compound was obtained as colorless crystal (0.50 g).

Inventive Examples 54 and 55

Resolution of (+)-ethyl 3-(2-(2-phenylethyl) benzimidazol-4-yl)-3-hydroxypropanoate (Inventive Example 54) and (−)-ethyl 3-(2-(2-phenylethyl) benzimidazol-4-yl)-3-hydroxypropanoate (Inventive Example 55) with an Optically Active Column Ethyl 3-(2-(2-phenylethyl)benzimidazol-4-yl)-3-hydroxypropanoate synthesized in Inventive Example 6 was separated by high performance liquid chromatography (CHIRALCEL OD™, manufactured by Daicel Chemical Industries, Ltd.; eluent: hexane/isopropanol/diethylamine= 80/20/1).

(+)-ethyl 3-(2-(2-phenylethyl)benzimidazol-4-yl)-3-hydroxypropanoate (Example 54) was obtained as the first fraction.

$^1$H-NMR (CDCl$_3$) δ [ppm]: 9.60 (1H, brs), 7.7–7.5 (1H, m), 7.3–7.1 (6H, m), 7.0–6.9 (1H, m), 5.5–5.4 (1H, m), 4.22 (2H, q, J=7 Hz), 3.3–3.1 (4H, m), 2.9–2.7 (2H, m), 1.30 (3H, t, J–7 Hz)

IR (KBr) [cm$^{-1}$]: 3032, 1734, 1433, 1286, 1024, 748

Melting point: 89.5–90.5° C.

HPLC optical purity: >99.5% e.e.

Specific rotation: $[\alpha]_D$=+16.70° (c=1.023, EtOH)

(−)-ethyl 3-(2-(2-phenylethyl)benzimidazol-4-yl)-3-hydroxypropanoate (Inventive Example 55) was obtained as the second fraction.

¹H-NMR (CDCl₃) δ[ppm]: 7.7–7.5 (1H, m) , 7.3–7.1 (6H, m), 7.0–6.9 (1H, m), 5.5–5.4 (1H, m), 4.22 (2H, q, J=7 Hz), 3.3–3.1 (4H, m), 2.9–2.8 (2H, m), 1.30 (3H, t, J-7 Hz)

IR (KBr) [cm⁻¹]: 3032, 1734, 1435, 1286, 1024, 748

Melting point: 89.8–90.7° C.

HPLC optical purity: 98.3% e.e.

Specific rotation: [α]$_D$=−16.75° (c=1.012, EtOH)

Inventive Examples 56 and 57

Synthesis of (+)-3-(2-(2-phenylethyl)benzimidazol-4-)-3-hydroxypropanoic Acid (Inventive Example 56, Corresponding to Inventive Example 8) and (−)-3-(2-(2-phenylethyl)benzimidazol-4-yl)-3-hydroxypropanoic acid (Inventive Example 57, Corresponding to Inventive Example 9)

3-(2-(2-phenylethyl)benzimidazol-4-yl)-3-hydroxypropanoic acid (3.1 g) synthesized in Inventive Example 7 and (+)-cis-N-benzyl-2-(hydroxymethyl)cyclohexylamine (2.19 g) were dissolved in 5% ethanol/acetone (30 ml) at elevated temperature, and (−) isomer-excessive seed crystals (73% e.e.) were added to the solution. The solution was allowed stand for 3 hours at room temperature, and the precipitated crystals were collected by filtration (1.9 g, 74% e.e.). The crystals were dissolved in 5% ethanol/acetone at elevated temperature, and seed crystals (94% e.e.) were added to the solution to obtain a salt of (−)-3-(2-(2-phenylethyl)benzimidazol-4-yl)-3-hydroxypropanoic acid (1.4 g, 91% e.e.). The intended (−)3-(2-(2-phenylethyl)benzimidazol-4-yl)-3-hydroxypropanoic acid can be obtained by dissociating this salt. The intended (+)-3-(2-phenylethyl)benzimidazol-4-yl)-3-hydroxypropanoic acid can be similarly obtained by using (−)-cis-N-benzyl-2-(hydroxymethyl)cyclohexylamine.

Figure 2:
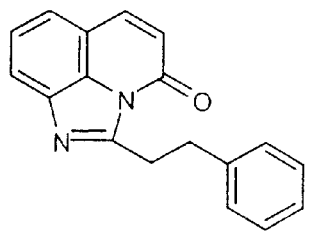
Figure 2:
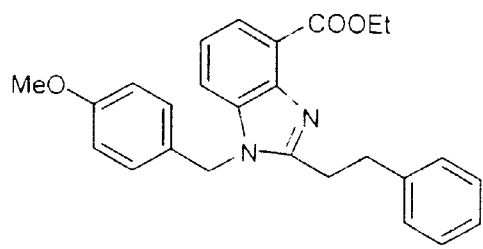
Figure 2:
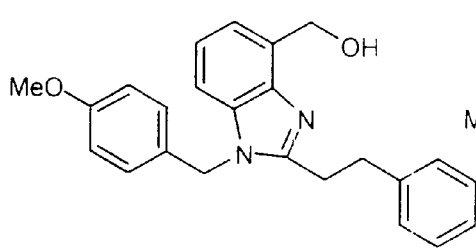
Figure 2:
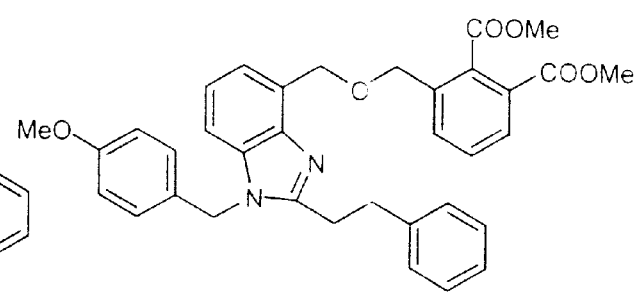
Figure 2:
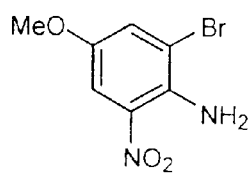
Figure 2:
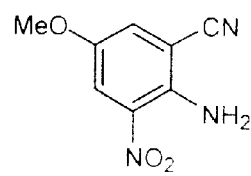
Figure 2:
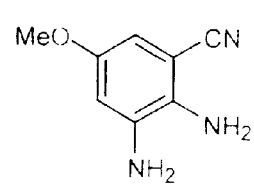
Figure 2:
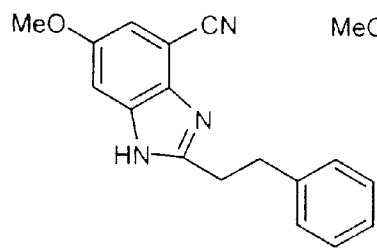
Figure 2:
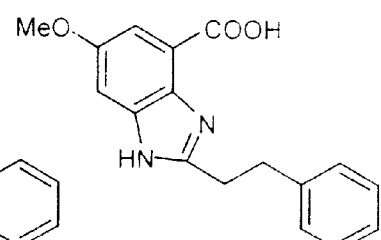
Figure 2:
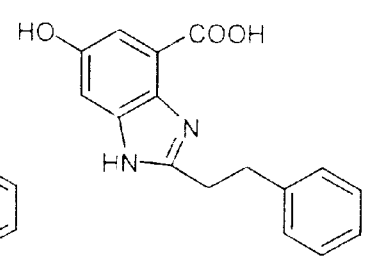
Figure 3:
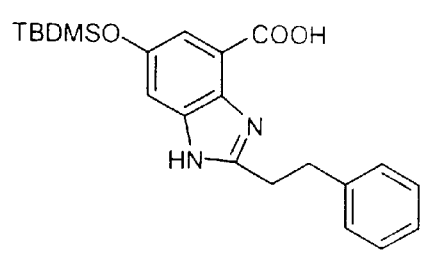
Figure 3:
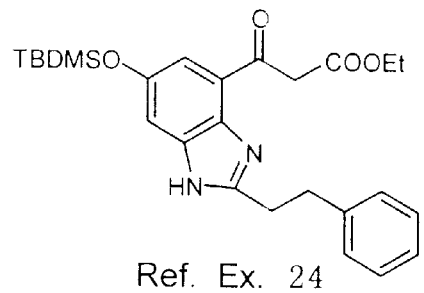
Figure 3:
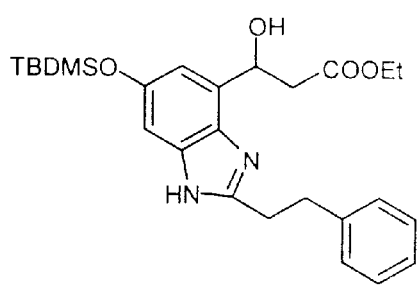
Figure 3:
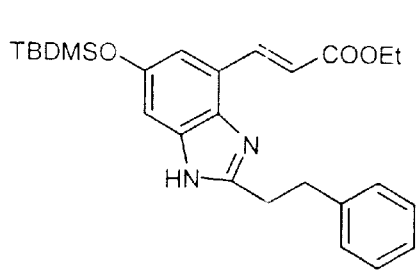
Figure 3:
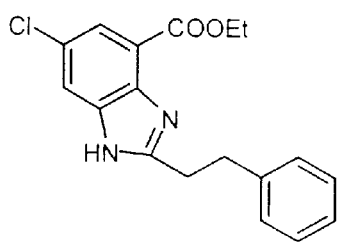
Figure 3:
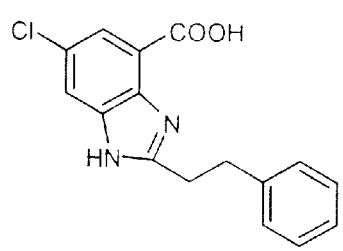
Figure 3:
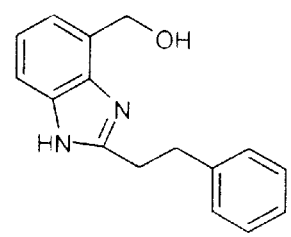
Figure 3:
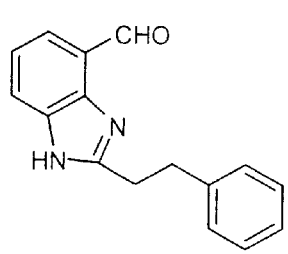
Figure 3:
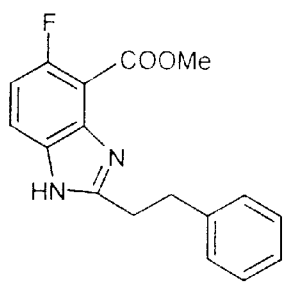
Figure 3:
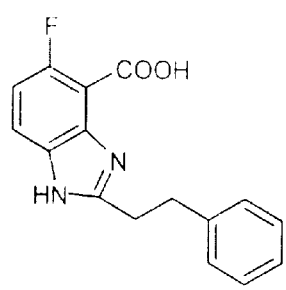
Figure 4:
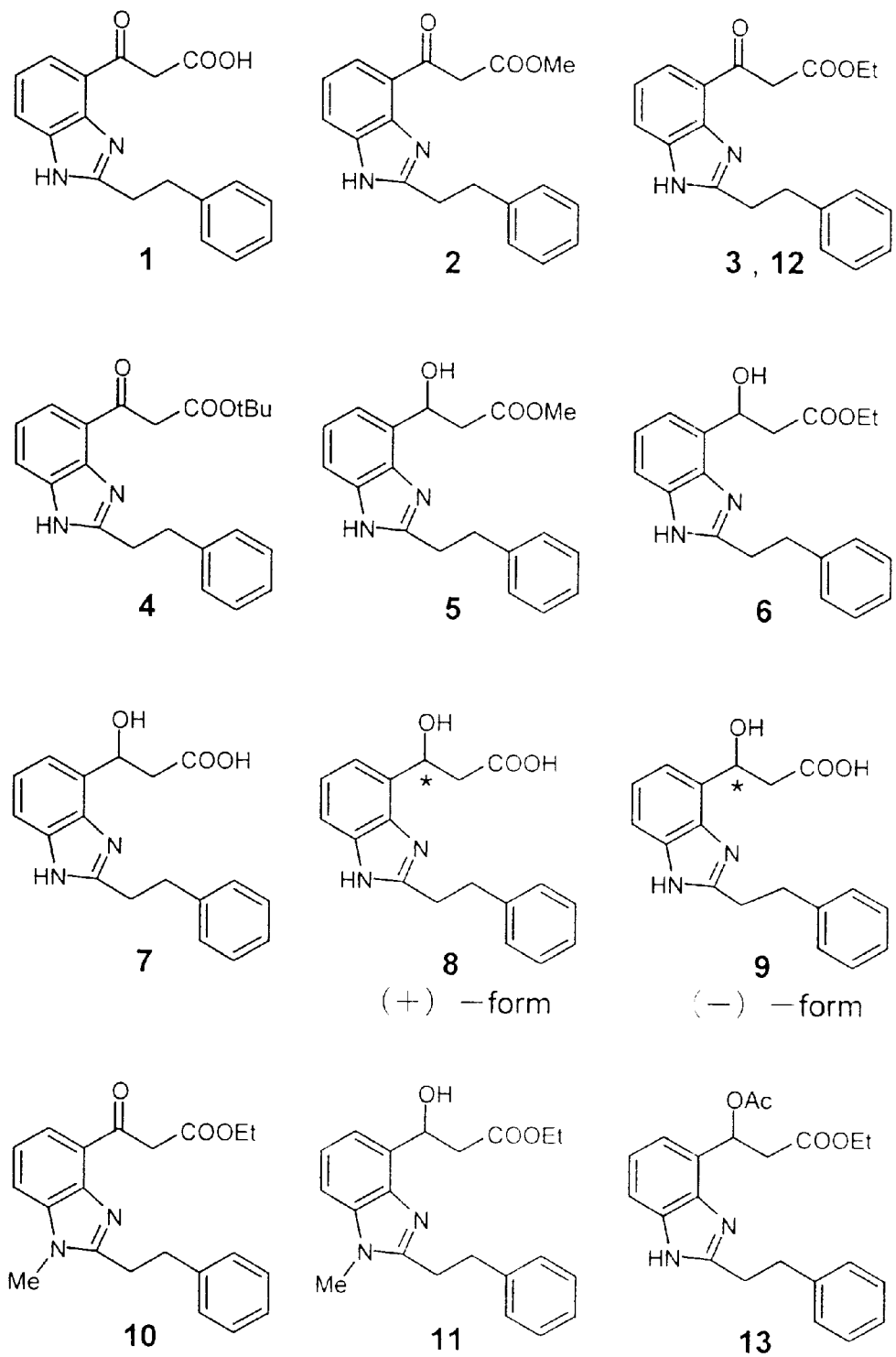
Figure 5:
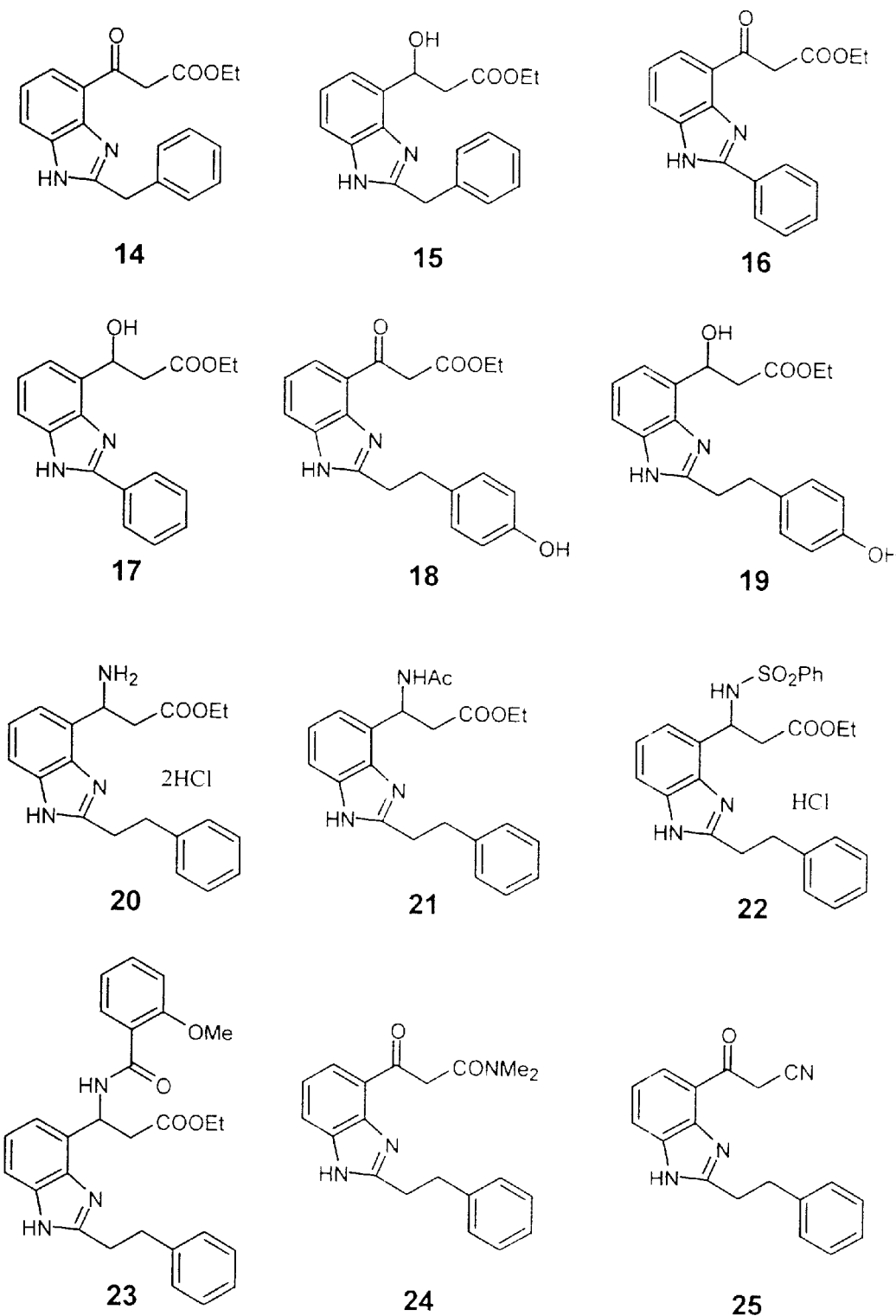
Figure 6:
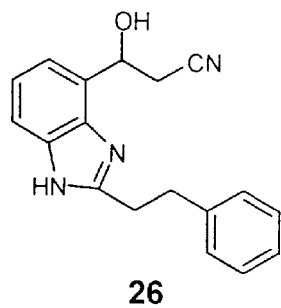
Figure 6:
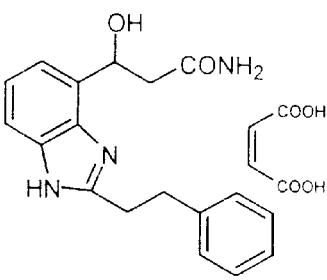
Figure 6:
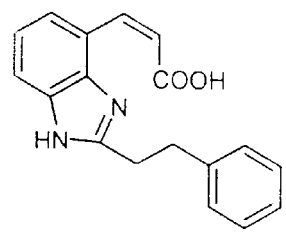
Figure 6:
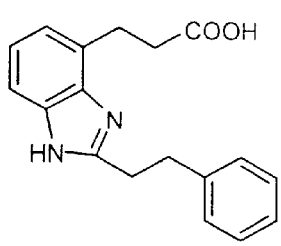
Figure 6:
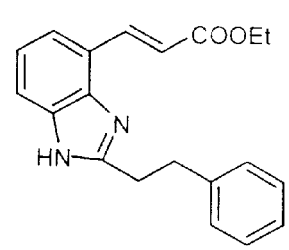
Figure 6:
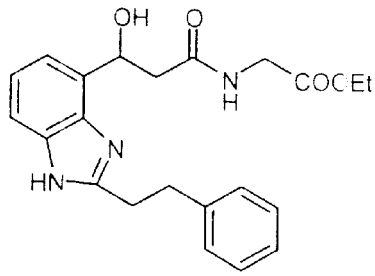
Figure 6:
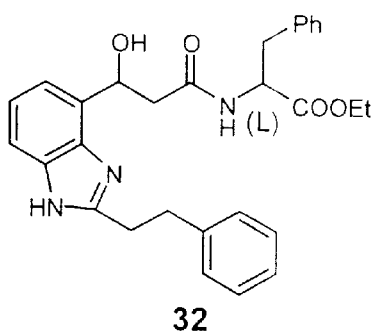
Figure 6:
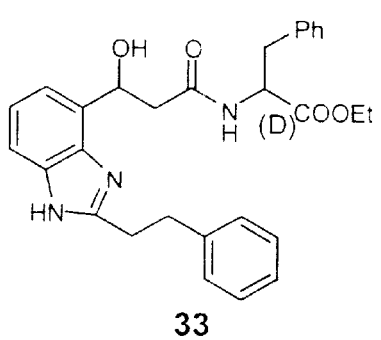
Figure 6:
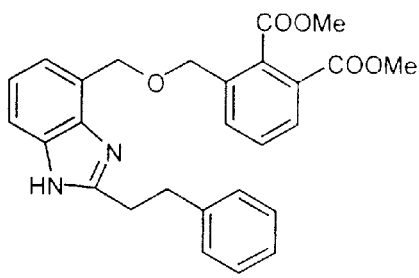
Figure 6:
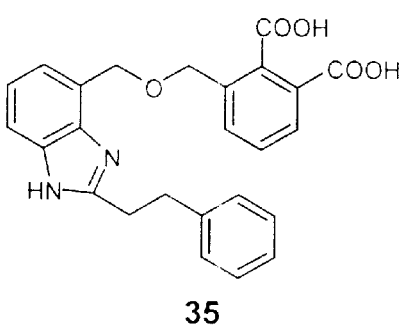
Figure 7:
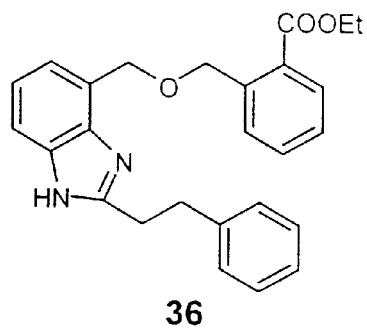
Figure 7:
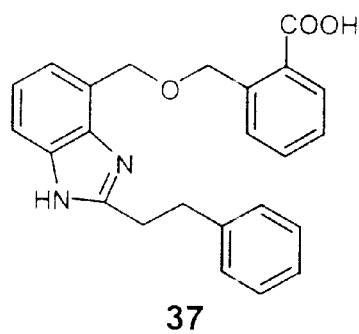
Figure 7:
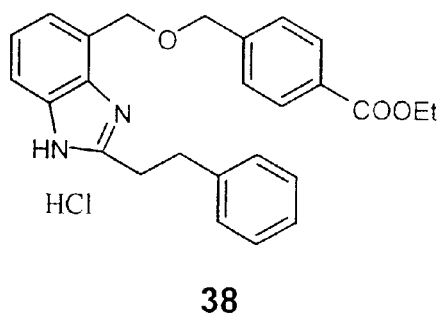
Figure 7:
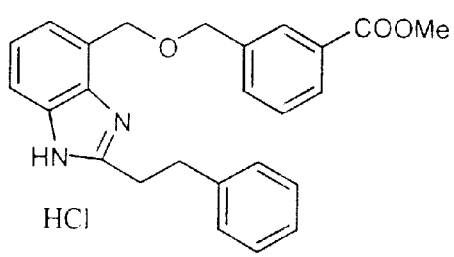
Figure 7:
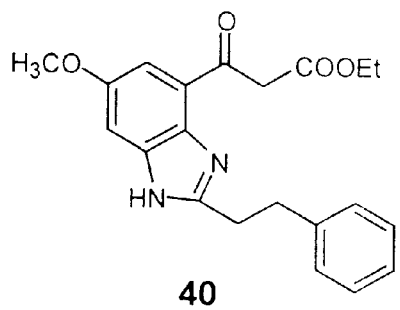
Figure 7:
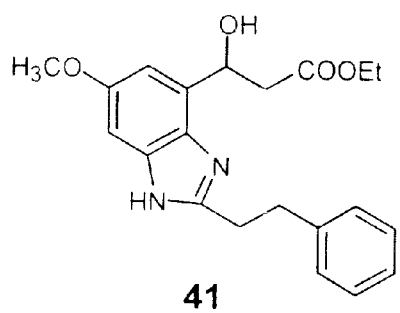
Figure 7:
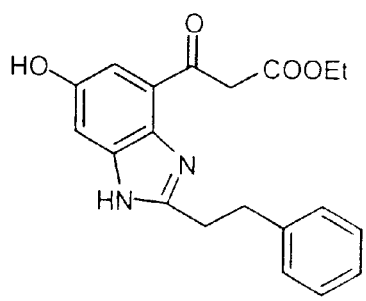
Figure 7:
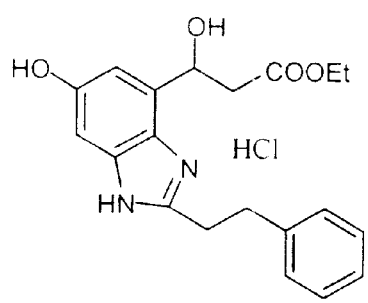
Figure 8:
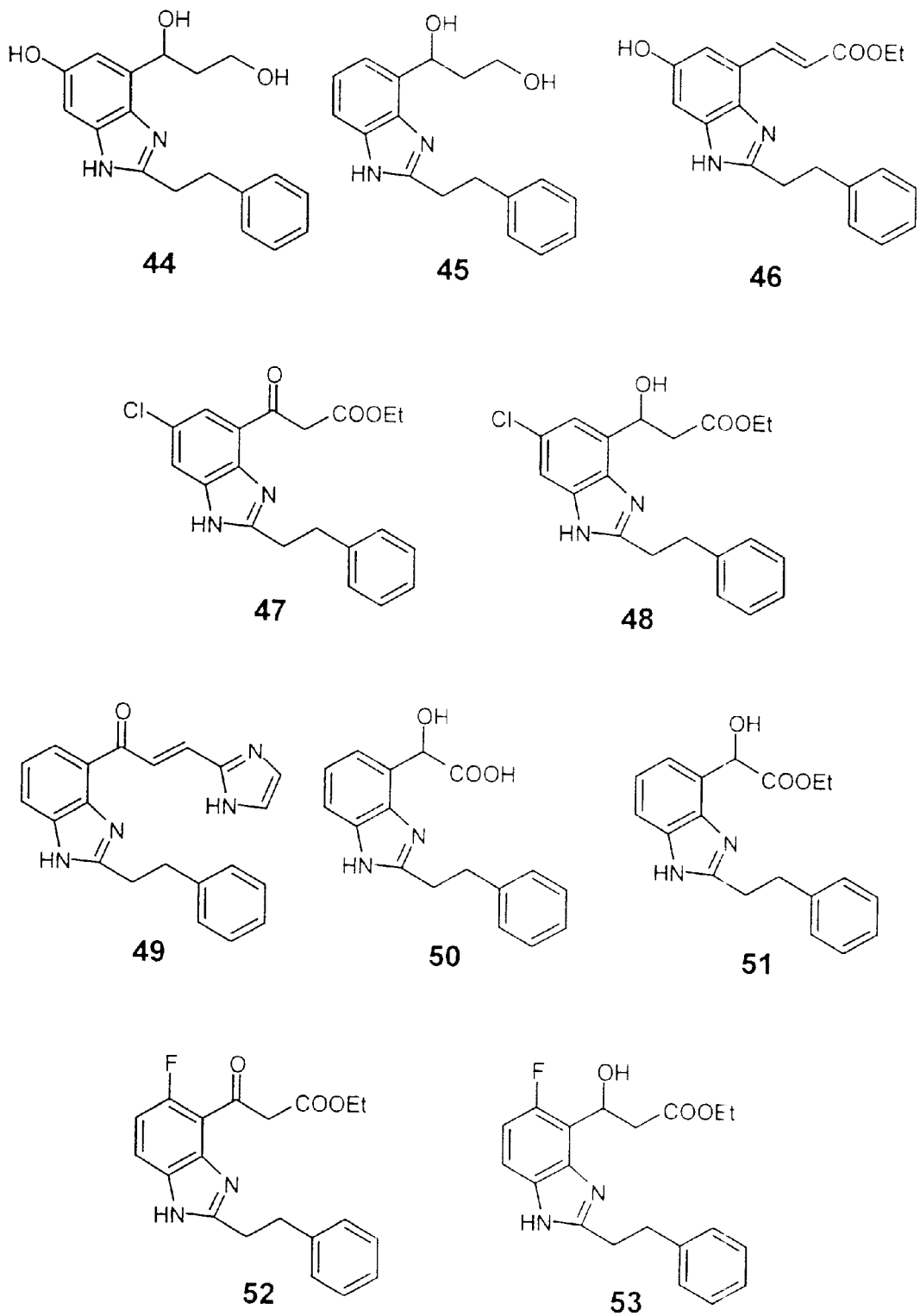

Structural formulae of the compounds synthesized in Reference Examples and Inventive Examples are shown in FIGS. 1 to 8. The number attached to each of the structural formula is the number of Inventive Example in which the corresponding compound has been synthesized, and this number is used as the compound number. Data on physical properties of the compounds synthesized in Inventive Examples 13 to 53, including NMR spectrum, IR spectrum and melting point, are shown in Table 3.

TABLE 3

| Inventive Example No. | IR cm⁻¹ | NMR ppm | M.P. (° C.) |
|---|---|---|---|
| 13 | KBr: 1747, 1736, 1416, 1238, 1217, 1180, 1024, 750 | CDCl₃: 7.8–7.6 (1 H, m), 7.4–7.2 (8 H, m), 6.6–6.5 (1 H, m), 4.15 (2H, q, J = 7 Hz), 3.3–2.8 (6 H, m), 2.05 (3 H, s), 1.23 (3 H, t, J = 7 Hz) | 96.4–97.7 |
| 14 | KBr: 3496, 1718, 1672, 1311, 1275, 1153, 1111, 1032 | CDCl₃: 10.52 (1 H, bs), 8.00 (1 H, d, J = 8 Hz), 7.71 (1 H, d, J = 8 Hz), 7.4–7.3 (6 H, m), 4.33 (2 H, s), 4.23 (2 H, q, J = 7 Hz), 4.07 (2 H, s), 1.27 (3 H, t, J = 7 Hz) | 85.6–89.9 |
| 15 | KBr: 1736, 1435, 1425, 1421, 1284, 1165, 1032, 750 | DMSO-d₆: 12.28 (1 H, bs), 7.5–7.0 (8 H, m), 5.67 (0.5 H, d, J = 4 Hz), 5.7–5.5 (0.5 H, m), 5.45 (0.5 H, d, J = 5 Hz), 5.4–5.2 (0.5 H, m), 4.19(2 H, s), 4.2–3.9 (2 H, m), 3.0–2.5 (2 H, m), 1.3–1.1 (3 H, m) | 123.7–124.8 |
| 16 | neat: 2981, 1740, 1734, 1666, 1477, 1454, 1367, 1302, 1286, 692 | CDCl₃: 11.16 (1 H, bs), 8.2–8.0 (3 H, m), 7.77 (1 H, d, J = 8 Hz), 7.6–7.5 (3 H, m), 7.36 (1 H, t, J = 8 Hz), 4.27 (2 H, q, J = 7 Hz), 4.14 (2 H, s), 1.30 (3 H, t, J = 7 Hz) | Oil |
| 17 | KBr: 3458, 3136, 1734, 1458, 1255, 756 | DMSO-d₆: 12.95 (0.7 H, bs), 12.57 (0.3 H, bs), 8.4–8.1 (2 H, m), 7.6–7.1 (6 H, m), 5.8–5.5 (2 H, m), 4.2–4.0 (2 H, m), 3.2–2.5 (2 H, m), 1.3–1.1 (3 H, m) | 154.7–156.0 |
| 18 | KBr: 3340, 1726, 1680, 1539, 1516, 1275, 1192, 1111, 739 | CDCl₃: 10.56 (1 H, bs), 7.96 (1 H, d, J = 8 Hz), 7.72 (1 H, d, J = 8 Hz), 7.31 (1 H, t, J = 8 Hz), 7.04 (2 H, d, J = 8 Hz), 6.70 (2 H, d, J = 8 Hz), 6.09 (1 H, bs), 4.25 (2 H, q, J = 7 Hz), 4.10 (2 H, s), 3.24 (2 H, t, J = 7 Hz), 3.12 (2 H, t, J = 7 Hz), 1.29 (3 H, t, J = 7 Hz) | 149.5–152.1 |
| 19 | KBr: 3462, 3429, 3408, 3392, 3365, 3342, 1713, 1516, 1024 | DMSO-d₆: 12.25 (0.5 H, bs), 12.10 (0.5 H, bs), 9.18 (1 H, s), 7.5–7.0 (5 H, m), 6.7–6.6 (2 H, m), 5.66 (0.5 H, d, J = 4 Hz), 5.6–5.5 (0.5 H, m), 5.45 (0.5 H, d, J = 5 Hz), 5.3–5.2 (0.5 H, m), 4.2–4.0 (2 H, m), 3.1–2.9 (4 H, m), 2.9–2.5 (2 H, m), 1.3–1.1(3 H, m) | 167.8–171.3 |
| 20 | KBr: 3408, 2872, 2623, 1741, 1497, 1205 | DMSO₆: 8.98 (2 H, bs), 7.8–7.7 (2 H, m), 7.54 (1 H, t, J = 8 Hz), 7.3–7.1 (5 H, m), 5.4–5.3 (1 H, m), 4.0–3.8 (2 H, m), 3.6–3.2 (6 H, m), 0.97 (3 H, t, J = 7 Hz) | 199.5 (dec.) |
| 21 | KBr: 3105, 3028, 1734, 1635, 1551, 1433, 1375, 1281, 748 | DMSO-d₆: 12.31 (0.7 H, bs), 12.21 (0.3 H, bs), 8.46 (0.3 H, d, J = 8 Hz), 8.38 (0.7 H, d, J = 9 Hz), 7.5–7.0 (8 H, m), 5.8–5.7 (0.7 H, m), 5.6–5.5 (0.3 H, m), 4.1–4.0 (2 H, m), 3.1–3.0 (5 H, m), 2.8–2.6 (1 H, m), 1.2–1.1 (3 H, m) | 159.6–162.1 |
| 22 | KBr: 1734, 1633, 1448, 1329, 1163, 1092, 752 | DMSO-d₆: 8.80 (1 H, d, J = 9 Hz), 7.44 (1 H, d, J = 8 Hz), 7.4–7.2 (11 H, m), 7.05 (1 H, t, J = 8 Hz), 5.16 (1 H, q, J = 8 Hz), 3.91 (2 H, q, J = 7 Hz), 3.44 (2 H, t, J = 8 Hz), 3.25 (2H, t, J = 8 Hz), 3.1–2.8 (2 H, m), 1.00 (3 H, t, J = 7 Hz) | 75.0–79.0 |
| 23 | KBr: 3201, 1730, 1637, 1533, 1483, 1244, 756 | DMSO-d₆: 12.41 (1 H, bs), 9.43 (1 H, d, J = 9 Hz), 7.87 (1 H, dd, J = 8, 2 Hz), 7.5–7.0 (11 H, m), 5.9–5.8 (1 H, m), 3.98 (2 H, q, J = 7 Hz), 3.90 (3 H, s), 3.2–3.0 (6 H, m), 1.05 (3H, t, J = 7 Hz) | 52.0–56.6 |
| 24 | KBr: 3300, 1659, 1633, 1427, 1271, 1122, 752 | CDCl₃: 10.81 (1 H, bs), 7.98 (1 H, d, J = 8 Hz), 7.83 (1 H, d, J = 8 Hz), 7.4–7.2 (6 H, m), 4.20 (2 H, s) 3.3–3.2 (4 H, m), 3.11 (3 H, s), 3.03 (3 H, s) | 97.3–101.7 |

TABLE 3-continued

| Inventive Example No. | IR cm$^{-1}$ | NMR ppm | M.P. (° C.) |
|---|---|---|---|
| 25 | KBr: 3028, 2918, 2260, 1682, 1525, 1269, 1113, 752 | CDCl$_3$: 10.46 (1 H, bs), 8.04 (1 H, d, J = 8 Hz), 7.63 (1 H, d, J = 8 Hz), 7.4–7.2 (6 H, m), 4.21 (2 H, s), 3.4–3.2 (4 H, m) | 144.9–145.5 |
| 26 | KBr: 3138, 2927, 2684, 2254, 1622, 1543, 1427, 1076, 1043, 762 | DMSO-d$_6$: 12.35 (0.6 H, bs), 12.16 (0.4 H, bs), 7.5–7.1(8 H, m), 6.14 (0.4 H, d, J = 4 Hz), 5.99 (0.6 H, d, J = 5 Hz), 5.5–5.4 (0.6 H, m), 5.3–5.2 (0.4 H, m), 3.12 (4 H, s), 3.2–2.8 (2H, m) | 136.3–138.0 |
| 27 | KBr: 3390, 3213, 1662, 1585, 1497, 1387, 1194, 1001, 702 | DMSO-d$_6$: 7.7–7.5 (1 H, m), 7.4–7.2 (8 H, m), 6.91 (1 H, bs), 6.12 (2 H, s), 5.73 (1 H, bs), 5.5–5.4 (1 H, m), 3.30 (2 H, t, J = 8 Hz), 3.14 (2 H, t, J = 8 Hz), 2.6–2.5 (2 H, m) | 118.6–121.8 |
| 28 | KBr: 3431, 3114, 2914, 2742, 1687, 1647, 1572, 1250, 822, 752 | DMSO-d$_6$: 7.73 (1 H, d, J = 8 Hz), 7.67 (1 H, d, J = 8 Hz), 7.48 (1 H, t, J = 8 Hz), 7.36 (1 H, d, J = 12 Hz), 7.3–7.2 (5 H, m), 6.31 (1 H, d, J = 12 Hz), 3.42 (2 H, t, J = 8 Hz), 3.20 (2 H, t, J = 8 Hz) | 98.8–100.9 |
| 29 | KBr: 2858, 1734, 1633, 1572, 1491, 1394, 1192, 1169, 752 | DMSO-d$_6$: 14.94 (1 H, bs), 7.61 (1 H, d, J = 8 Hz), 7.46 (1 H, t, J = 8 Hz), 7.4–7.2 (6 H, m), 3.44 (2 H, t, J = 8 Hz), 3.22 (2 H, t, J = 8 Hz), 3.15 (2 H, t, J = 8 Hz), 2.69 (2 H, t, J = 8 Hz) | 171.2–173.7 |
| 30 | KBr: 3273, 2980, 1699, 1632, 1535, 1423, 1321, 1211, 1184 | CDCl$_3$: 8.02 (1 H, d, J = 16 Hz), 7.6–6.9 (9 H, m), 4.29 (2 H, q, J = 7 Hz), 3.4–3.2 (4 H, m), 1.35 (3 H, t, J = 7 Hz) | 132.1–133.9 |
| 31 | KBr: 3290, 1749, 1737, 1649, 1545, 1425, 1201, 1038, 748, 702 | CDCl$_3$: 7.50 (1 H, bs), 7.4–6.9 (9 H, m), 5.5–5.4 (1 H, m), 4.23 (2 H, q, J = 7 Hz), 4.11 (1 H, dd, J = 18, 5 Hz), 4.03 (1 H, dd, J = 18, 5 Hz), 3.2–3.0 (4 H, m), 2.9–2.6 (2 H, m), 1.30 (3 H, t, J = 7 Hz) | 123.6–128.7 |
| 32 | KBr: 3317, 3180, 3166, 1732, 1645, 1533, 1417, 1203, 700 | DMSO-d$_6$: 12.26 (0.5 H, bs), 12.02 (0.5 H, bs), 8.4–8.3 (1 H, m), 7.5–7.0 (14 H, m), 5.7–5.5 (1 H, m), 5.36 (0.5 H, d, J = 4 Hz), 5.3–5.2 (0.5 H, m), 4.6–4.4 (1 H, m), 4.1–3.9 (2 H, m), 3.09 (4 H, s), 3.1–2.5 (4 H, m)1.2–1.0 (3 H, m) | 133.3–154.2 |
| 33 | KBr: 3340, 3192, 1732, 1643, 1533, 1417, 760, 700 | DMSO-d$_6$: 12.26 (0.5 H, bs), 12.04 (0.5 H, bs), 8.4–8.3 (1 H, m), 7.5–7.0 (14 H, m), 5.6–5.5 (1 H, m), 5.37 (0.5 H, d, J = 5 Hz), 5.3–5.2 (0.5 H, m), 4.6–4.4 (1 H, m), 4.1–3.9 (2H, m), 3.10 (4 H, s), 3.1–2.5 (4 H, m)1.2–1.0 (3 H, m) | 134.1–135.5 |
| 34 | neat: 3313, 2953, 1728, 1454, 1431, 1282, 1198, 1151, 1119, 1072, 750, 700 | CDCl$_3$: 10.54 (1 H, bs), 8.01 (1 H, d, J = 7 Hz), 7.65 (1 H, d, J = 8 Hz), 7.57 (1 H, d, J = 6 Hz), 7.49 (1 H, t, J = 8 Hz), 7.3–7.2 (5 H, m), 7.13 (1 H, t, J = 8 Hz), 7.00 (1 H, d, J = 7 Hz), 4.79 (2 H, s), 4.65 (2 H, s), 3.94 (3 H, s), 3.89 (3 H, s), 3.3–3.1 (4 H, m) | Oil |
| 35 | KBr: 2922, 2868, 1707, 1581, 1564, 1456, 1381, 1271, 752 | DMSO-d$_6$: 7.80 (1 H, d, J = 8 Hz), 7.74 (1 H, d, J = Hz), 7.51 (1 H, t, J = 8 Hz), 7.43 (1 H, d, J = 7 Hz), 7.4–7.1 (7 H, m), 4.84 (2 H, s), 4.66 (2 H, s), 3.12 (4 H, s) | 160.3–163.5 |
| 36 | neat: 1714, 1450, 1443, 1433, 1263, 1136, 1078, 744 | CDCl$_3$: 10.38 (1 H, bs), 7.97 (1 H, d, J = 8 Hz), 7.7–7.0 (11 H, m), 4.91 (2 H, s), 4.89 (2 H, s), 4.36 (2 H, q, J = 7 Hz), 3.20 (4 H, s), 1.36 (3 H, t, J = 7 Hz) | Oil |
| 37 | KBr: 2927, 2864, 1583, 1549, 1443, 1383, 1084, 750 | CDCl$_3$: 7.93–7.87 (1 H, m), 7.62 (1 H, d, J = 8 Hz), 7.4–7.3 (3 H, m), 7.21 (1 H, t, J = 8 Hz), 7.14 (1 H, d, J = 7 Hz), 6.9–6.7 (5 H, m), 4.88 (2 H, s), 4.81 (2 H, s), 3.28 (2 H, t, J = 8 Hz), 2.91 (2 H, t, J = 8 Hz) | 86.3–88.1 |
| 38 | KBr: 3490, 2856, 1718, 1277, 1109 | CDCl$_3$: 14.34 (1 H, bs), 7.94 (2 H, d, J = 8 Hz), 7.70 (1 H, s), 7.5–7.3 (4 H, m), 7.09 (2 H, s), 6.98 (3 H, s), 4.99 (2 H, s), 4.75 (2 H, s), 4.35 (2 H, q, J = 7 Hz), 3.53 (2 H, bs), 3.24 (2 H, bs), 1.37 (3 H, t, J = 7 Hz) | 145.4–148.6 |
| 39 | KBr: 3426, 2854, 1722, 1288, 1203, 1105, 748 | CDCl$_3$: 14.25 (1 H, bs), 7.98 (1 H, s), 7.90 (1 H, d, J = 7 Hz), 7.70 (1 H, d, J = 5 Hz), 7.54 (1 H, d, J = 7 Hz), 7.4–7.3 (3 H, m), 7.10 (2 H, s), 6.99 (3 H, s), 4.99 (2 H, s), 4.73 (2 H, s), 3.85 (3 H, s), 3.55 (2 H, bs), 3.25 (2 H, bs) | 83.7–87.5 |
| 40 | KBr: 3404, 2916, 1732, 1660, 1522, 1336, 1269, 1228, 1203, 1151 | CDCl$_3$: 10.34(1 H, bs), 7.53 (1 H, d, J = 2 Hz), 7.4–7.2 (6 H, m), 4.24 (2 H, q, J = 7 Hz), 4.05 (2 H, s), 3.90 (3 H, s), 3.3–3.1 (4 H, m), 1.29 (3 H, t, J = 7 Hz) | 138.5–139.2 |
| 41 | KBr: 3302, 1722, 1630, 1452, 1425, 1198, 1180, 1149 | CDCl$_3$: 9.47 (1 H, bs), 7.4–7.1 (7 H, m), 6.61 (1 H, bs), 5.37 (1 H, bs), 4.22 (2 H, q, J = 7 Hz), 3.83 (3 H, s), 3.3–3.1 (4 H, m), 2.9–2.7 (2 H, m), 1.30 (3 H, t, J = 7 Hz) | 126.9–127.7 |
| 42 | KBr: 3410, 2980, 1734, 1666, 1524, 1427, 1346, 1290, 1153, 1132, 700 | DMSO-d$_6$: 12.34 (0.4 H, bs), 12.32 (0.6 H, bs), 9.46 (0.4 H, s), 9.37 (0.6 H, s), 7.3–7.0 (6.6 H, m), 4.54 (0.8 H, s), 4.20 (12 H, s), 4.2–4.0 (2 H, m), 3.11 (4 H, s), 1.2–1.1 (3 H, m) | 169.1–170.0 |
| 43 | KBr: 3184, 3136, 1726, 1637, 1497, 1159, 700 | DMSO-d$_6$: 10.02 (1 H, bs), 7.3–7.2 (5 H, m), 7.0–6.8 (2 H, m), 6.07 (1 H, bs), 5.28 (1 H, t, J = 7 Hz), 4.05 (2 H, q, J = 7 Hz), 3.40 (2 H, t, J = 8 Hz), 3.16 (2 H, t, J = 8 Hz), 2.8–2.7 (2 H, m), 1.14 (3 H, t, J = 7 Hz) | 189.3–192.5 |
| 44 | KBr: 3304, 2931, 1632, 1606, 1454, | DMSO-d$_6$: 11.89 (0.6 H, bs), 11.69 (0.4 H, bs), 8.97 (0.6 H, bs), 8.78 (0.4 H, bs), 7.4–7.2 (5 H, m), 6.8–6.6 (2 H, | 77.2–80.2 |

TABLE 3-continued

| Inventive Example No. | IR cm$^{-1}$ | NMR ppm | M.P. (° C.) |
|---|---|---|---|
| | 1427, 1151, 700 | m), 5.4–5.3 (0.4 H, m), 5.3–5.2 (0.6 H, m), 5.2–5.0 (0.6 H, m), 5.0–4.8 (0.4 H, m), 4.8–4.6 (0.6 H, m), 4.5–4.4 (0.4 H, m),3.6–3.3 (2 H, m), 3.04 (4H, s), 1.9–1.7 (2 H, m) | |
| 45 | KBr: 3113, 3109, 3062, 2918, 1454, 1423, 1106, 1066 | DMSO-d$_6$: 12.26 (0.4 H, bs), 11.96 (0.6 H, bs), 7.5–7.0 (8 H, m), 5.35 (0.6 H, d, J = 4 Hz), 5.4–5.3 (0.4 H, m), 5.11 (0.4 H, d, J = 5 Hz), 5.0–4.9 (0.6 H, m), 4.61 (0.4 H, t, J = 5 Hz), 4.42 (0.6 H, t, J = 5 Hz), 3.6–3.4 (2 H, m), 3.10 (4 H, s), 2.1–1.7 (2 H, m) | 146.4–148.6 |
| 46 | KBr: 3481, 3427, 3398, 3367, 1697, 1635, 1417, 1288, 1180 | DMSO-d$_6$: 12.19 (1 H, s), 9.29 (1 H, s), 7.82 (1 H, d, J = 16 Hz), 7.4–7.1 (6 H, m), 6.86 (2 H, s), 4.20 (2 H, q, J = 7 H), 3.10 (4 H, s), 1.28 (3 H, t, J = 7 Hz) | 169.2–172.7 |
| 47 | KBr: 3348, 2985, 2939, 1732, 1666, 1522, 1281, 1257, 716 | CDCl$_3$: 10.48 (1 H, bs), 7.95 (1 H, d, J = 2 Hz), 7.68 (1 H, d, J = 2 Hz), 7.4–7.2 (5 H, m), 4.25 (2 H, q, J = 7 Hz), 4.05 (2 H, s), 3.3–3.2 (4 H, m), 1.30 (3 H, t, J = 7 Hz) | 118.8–119.7 |
| 48 | KBr: 3116, 1718, 1527, 1452, 1419, 1294, 1178, 1028, 854, 700 | DMSO-d$_6$: 12.46 (0.5 H, bs), 12.36 (0.5 H, bs), 7.5–7.1 (7 H, m), 5.82 (0.5 H, d, J = 4 Hz), 5.7–5.5 (1 H, m), 5.3–5.2 (0.5 H, m), 4.2–4.0 (2 H, m), 3.2–3.0 (4.5 H, m), 2.8–2.7 (1 H, m), 2.6–2.5 (0.5 H, m), 1.3–1.1 (3 H, m) | 106.1–107.3 |
| 49 | KBr: 3045, 1659, 1614, 1599, 1522, 1429, 1267, 1122, 739 | DMSO-d$_6$: 12.93 (1 H, bs), 12.70 (1 H, bs), 8.07 (1 H, d, J = 16 Hz), 8.01 (1 H, d, J = 8 Hz), 7.90 (1 H, J = 8 Hz), 7.58 (1 H, d, J = 16 Hz), 7.47 (1 H, brs), 7.4–7.2 (7 H, m), 3.3–3.1 (4 H, m) | 172.0–174.3 |
| 50 | KBr: 3398, 3061, 2927, 1633, 1601, 1439, 1369, 1080, 750 | DMSO-d$_6$: 7.47 (1 H, dd, J = 7, 1 Hz), 7.4–7.1 (7 H, m), 5.55 (1 H, s), 3.3–3.1 (4 H, m) | 127.6–130.2 |
| 51 | KBr: 2983, 2638, 1738, 1497, 1421, 1207, 1018, 760 | DMSO-d$_6$: 12.37 (0.5 H, bs), 12.14 (0.5 H, bs), 7.5–7.0 (8 H, m), 6.20 (0.5 H, d, J = 5 Hz), 5.97 (0.5 H, d, J = 6 Hz), 5.74 (0.5 H, d, J = 6 Hz), 5.51 (0.5 H, d, J = 5 Hz), 4.4–4.0 (2 H, m), 3.12 (4 H, s), 1.10 (3 H, t, J = 7 Hz) | 202.6–204.2 |
| 52 | KBr: 3430, 1751, 1670, 1601, 1373, 1157 | CDCl$_3$: 10.65 (1 H, brs), 7.89 (1 H, dd, J = 9, 5 Hz), 7.4–7.2 (5 H, m), 7.04 (1 H, dd, J = 12, 9 Hz), 4.25 (2 H, q, J = 7 Hz), 4.08 (2 H, d, J = 4 Hz), 3.3–3.1 (4 H, m), 1.29 (3 H, t, J = 7 Hz) | 83.9–85.1 |
| 53 | KBr: 3211, 2979, 1736, 1443, 1257, 1039, 812 | DMSO-d$_6$: 12.42 (0.3 H, bs), 12.11 (0.7 H, bs), 7.41 (0.7 H, dd, J = 9, 5 Hz); 7.4–7.2 (5.3 H, m), 7.0–6.9 (1 H, m), 5.96 (0.7 H, d, J = 4 Hz), 5.7–5.5 (1.3 H, m), 4.1–4.0 (2 H, m), 3.2–3.0 (4 H, m), 3.0–2.6 (2 H, m), 1.14 (3 H, t, J = 7 Hz) | 114.1–116.9 |

Examples of the formulation of pharmaceutical preparations which contain compounds of the present invention are shown in the following, but the invention is not restricted thereby.

Formulation Example 1 Capsules

| Components | Amount used (g) |
|---|---|
| Compound of Inventive Example 6 | 50 |
| Lactose | 935 |
| Magnesium stearate | 15 |

The above components were respectively weighed and uniformly mixed. By filling appropriate hard capsules with the thus obtained powder mixture in 200 mg portions, capsules were successfully produced.

Formulation Example 2 Capsules

The same preparation method in the Formulation Example 1 was used except that the Compound of Inventive Example 55 was used instead of the Compound of Inventive Example 6.

Formulation Example 3 Tablets

| Components | Amount used (g) |
|---|---|
| Compound of Inventive Example 2 | 100 |
| Lactose | 350 |
| Potato starch | 120 |
| Polyvinyl alcohol | 15 |
| Magnesium stearate | 15 |

After weighing each of the above components, the title compound was uniformly mixed with lactose and potato starch. Aqueous solution of polyvinyl alcohol was added to the mixture to prepare granules by a wet granulation method. The granules were dried, mixed with magnesium stearate and then made into tablets, each having 300 mg in weight, preparing use of a compressive tablet making machine.

Formulation Example 4 Tablets)

The same preparation method in the Formulation Example 3 was used except that the Compound of Inventive Example 9 was used instead of the Compound of Inventive Example 2.

Formulation Example 5 Granules

| Components | Amount used (g) |
|---|---|
| Compound of Inventive Example 3 | 200 |
| Lactose | 450 |
| Corn starch | 300 |
| Hydroxypropylcellulose | 50 |

After weighing and uniformly mixing the above components, granules were successfully produced in the usual way.

Formulation Example 6 Granules

The same preparation method in the Formulation Example 5 was used except that the Compound of Inventive Example 54 was used instead of the Compound of Inventive Example 3.

Formulation Example 7 Injections

| Components | Amount used (g) |
|---|---|
| Compound of Inventive Example 7 | 2 g |
| Sodium bicarbonate | 10 g |
| Distilled water for injection use | 1,000 mL |

Sodium bicarbonate was dissolved in distilled water for injection use, and the compound of Inventive Example 7 was dissolved in the solution. The resulting solution was sterilized by filtration and dispensed in 5 mL portions into 10 mL capacity ampoules which were then melt-sealed, thereby obtaining injections.

Formulation Example 8 Injections

The same preparation method in the Formulation Example 7 was used except that the Compound of Inventive Example 8 was used instead of the Compound of Inventive Example 7.

INDUSTRIAL APPLICABILITY

When the compound of the present invention having benzimidazole nucleus is used, the compound exerts strong action of inhibiting eosinophilia as well as the action of enhancing the IFN-γ production of the immunocompetent cells. Since the compound of the present invention having benzimidazole nucleus has high safety due to its extremely low toxicity, the compound is expected to exert strong action of inhibiting eosinophilia in the clinical practice (human) and in animals to produce excellent preventive and/or therapeutic effects on diseases exhibiting eosinophilia, bronchial asthma or allergic diseases. The compound is also expected to exert strong action of enhancing the IFN-γ production of the immunocompetent cells to thereby enable its therapeutic or prophylactic use on the diseases wherein enhancement of the IFN-γ production is effective, for example, tumors, viral diseases (for example, viral hepatitis (type A, B, C, E, etc.), influenza, viral pneumonia, viral bronchitis, herpes infections (herpes simplex virus, EB virus (infectious mononucleosis), herpes zoster, polio, HIV infections, etc.), bacterial infections (for example, liver tumor, liver amebiasis), or the like, or in particular as an antitumor agent.

In addition, prevention and/or treatment of diseases exhibiting eosinophilia, bronchial asthma and allergic diseases can be achieved by the medicaments and pharmaceutical compositions of the present invention. More specifically, the medicaments and pharmaceutical compositions of the present invention which strongly inhibit eosinophilia are effective for the prevention and/or treatment of diseases in which eosinophils are probably concerned in their pathophysiology, namely parasite infection, hypereosinophilic syndrome (HES), eosinophilic pneumonia, eosinophilic enterogastritis, bronchial asthma, atopic dermatitis, allergic rhinitis or the like diseases. In addition, it is also effective for the prevention and/or treatment of diseases caused by IgE antibody, such as hay fever, angioneurotic edema, serous otitis media, pollinosis, allergic enterogastritis, food allergy, drug allergy or the like allergic diseases.

In addition, prevention and/or treatment of diseases wherein enhancement of the IFN-γ production is effective can be achieved by the medicaments and pharmaceutical compositions of the present invention. More specifically, the medicaments and pharmaceutical compositions of the present invention are effective in coping with the diseases wherein enhancement of the IFN-γ production is effective, for example, tumors, viral diseases (for example, viral hepatitis (type A, B, C, E, etc.), influenza, viral pneumonia, viral bronchitis, herpes infections (herpes simplex virus, EB virus (infectious mononucleosis), herpes zoster, polio, HIV infections, etc.), bacterial infections (for example, liver tumor, liver amebiasis), or the like by prevention, prevention of the onset or worsening, amelioration, or healing of the disease. The medicaments and pharmaceutical compositions of the present invention are also effective for use in preventing or treating various tumors.

When the enhancer for the IFN-γ production containing the compound of the present invention is used, the immunocompetent cells is allowed to acquire the character of an increased basal IFN-γ production rate under stationary conditions, and consequently, stable IFN-γ production can be expected with no drug or stimulation, and increased IFN-γ production can be expected with the drug or stimulation. Production of a safe drug with reduced side effects is thereby enabled in contrast to the case of direct IFN-γ administration or induction of the IFN-γ production by direct stimulation.

What is claimed is:

1. A compound represented by the following formula (I)

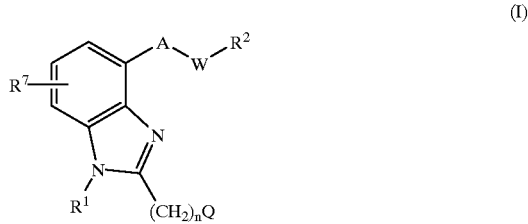

(I)

(wherein $R^1$ represents hydrogen atom or a straight- or branched-chain alkyl group having 1 to 4 carbon atoms, $R^2$ represents cyano group, hydroxymethyl group, 2-(2-imidazolyl)ethenyl group, a phenyl group substituted by one or two —$COOR^3$ groups, or a group —$COOR^3$ or —$CONR^4R^5$, $R^3$ represents hydrogen atom or a straight- or branched-chain alkyl group having 1 to 4 carbon atoms, each of $R^4$ and $R^5$ represents hydrogen atom, an alkyl group having 1 or 2 carbon atoms or a group —$CH_2COOR^6$ or —CH(CH$_2$Ph)COOR$^6$, wherein R$^4$ and R$^5$ may be the same or different from each other but, when one of R$^4$ and R$^5$ is a group —CH$_2$COOR$^6$ or —CH(CH$_2$Ph)COOR$^6$, the other one is hydrogen atom, A represents any one of groups selected from the class consisting of —CO—, —CH(OR$^8$)—, —CH$_2$O—, —CH(NHR$^9$)CH$_2$—, —CH=CH— and —CH$_2$CH$_2$—, W represents a group —CH$_2$— or a single bond, Q represents a phenyl group which may be substituted by one hydroxyl group, n is from 0 to 2, R$^6$ represents a straight- or branched-chain alkyl group having 1 to 4 carbon atoms, R$^7$ represents hydrogen atom, hydroxyl group, a halogen atom or a straight- or branched-chain alkoxyl group having 1 to 4 carbon atoms, R$^8$ represents hydrogen atom or acetyl group and R$^9$ represents hydrogen atom, acetyl group, phenylsulfonyl group or a benzoyl group which may be substituted by one methoxy group) or a salt thereof.

2. The compound or a salt thereof according to claim 1 wherein n is 2.

3. The compound or a salt thereof according to claim 1 or 2 wherein R$^2$ is a phenyl group substituted by one or two —COOR$^3$ groups or a group —COOR$^3$ or —CONR$^4$R$^5$.

4. The compound or a salt thereof according to claim 1 wherein R$^1$ is hydrogen atom, W is a group —CH$_2$—, A is any one of groups selected from the class consisting of —CO—, —CH (OR)— and —CH$_2$O—, and R$^2$ is a group —COOR$^3$ or a phenyl group substituted by one or two —COOR$^3$ groups.

5. An optically active compound represented by the following formula (I)-w

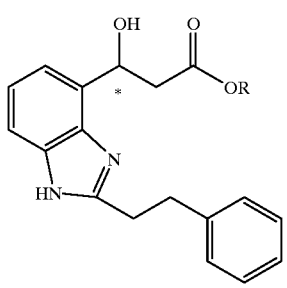

(I)-w (wherein R represents hydrogen atom or a lower alkyl group, and * is an asymmetric carbon atom) or a pharmaceutically acceptable salt thereof.

6. A process for producing the compound of formula (I) of claim 1 or a salt thereof, which comprises treating a compound represented by the following formula (III)

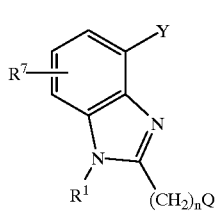

(III)

(wherein Y represents acetyl group, —COOR$^3$, a halogen atom, formyl group, chloroformyl group or bromoformyl group, R$^1$ and R$^3$ independently represents hydrogen atom or a straight- or branched-chain alkyl group having 1 to 4 carbon atoms, R$^7$ represents hydrogen atom, hydroxyl group, a halogen atom or a straight- or branched-chain alkoxyl group having 1 to 4 carbon atoms, Q represents a phenyl group which may be substituted by one hydroxyl group and n is from 0 to 2) or a salt thereof in accordance with any one of the steps selected from the group consisting of the following steps (a) to (k):

(a) the compound is allowed to react with carbon dioxide in the presence of an inorganic base or an organic base or with a carbamato complex in an inert solvent, thereby obtaining corresponding carboxylic acid derivatives, (b) the compound is allowed to react with halogenoformic acid ester, dialkyl carbonate, phosphonoformic acid ester or oxalic acid ester in the presence of a base, (c) the compound is allowed to react with malonic acid ester in the presence of a base, and then subjected to hydrolysis and subsequent decarboxylation, (d) an acetic acid or an acetic acid ester is prepared into a metal reagent using a metalating agent, and then the compound is allowed to react with the reagent, (e) a halogeno-acetic acid derivative is prepared into Reformatsky reagent, and then the compound is allowed to react with the reagent, (f) the compound is allowed to react with Meldrum's acid in the presence of a base to convert it into acyl Meldrum's acid which is then subjected to solvolysis and decarboxylation using an alcohol, (g) the compound is allowed to react with a malonic acid ester, (h) using a transition metal complex, the compound is allowed to undergo cross-coupling reaction with an acetylene compound, and then hydration is carried out, (i) the compound is subjected to halogen-metal exchange reaction using an organic lithium reagent, allowed to react with ethylmalonyl chloride and then subjected to hydrolysis and decarboxylation, (j) the compound is reduced using a metal hydride, allowed to react with substituted benzyl halides in the presence of a base, (k) the compound is allowed to react with hydrogen cyanide or trimethylsilyl cyanide in the presence of a Lewis acid, and then hydrolyzed.

7. The process according to claim 6 which comprises subjecting the compound obtained by treating said compound represented by formula (III) in accordance with any one of the steps selected from the group consisting of steps (a) to (k) to a reduction, an oxidation or a substituent change.

8. The process according to claim 6 wherein said compound represented by formula (III) is treated in accordance with step (a) and wherein the compound is allowed to react with carbon dioxide in the presence of an inorganic base or an organic base and in the presence of a phase-transfer catalyst, magnesium chloride, sodium iodide, or diphenyl urea.

9. The process according to claim 8 wherein the obtained corresponding carboxylic acid derivative is further subjected to esterification.

10. The process according to claim 6 wherein said compound represented by formula (III) is treated in accordance with step (b) and wherein the obtained compound is further subjected to hydrolysis.

11. The process according to claim 6 wherein said compound represented by formula (III) is treated in accordance with step (c) and wherein the obtained compound is further subjected to esterification.

12. The process according to claim 6 wherein said compound represented by formula (III) is treated in accordance with step (f) and wherein the obtained compound is subjected to hydrolysis.

13. The process according to claim 6 wherein said compound represented by formula (III) is treated in accordance with step (g) and wherein the obtained compound is subjected to hydrolysis and decarboxylation.

14. The process according to claim 6 wherein said compound represented by formula (III) is treated in accordance with step (j) and wherein the obtained compound is hydrolyzed in the substituted group.

15. The process according to claim 6 wherein said compound represented by formula (III) is treated in accordance with step (k) and wherein the obtained compound is subjected to esterification.

16. A pharmaceutical composition comprising an effective amount of the compound represented by the formula (I) of claim 1 or a pharmaceutically acceptable salt thereof as its active ingredient, and a pharmaceutically acceptable carrier.

17. A method of treating diseases exhibiting eosinophilia comprising administering to a patient in need thereof a therapeutically effective amount of the compound of claim 1 or a pharmaceutically acceptable salt thereof.

18. The method according to claim 17 wherein said disease is a disease selected from the group consisting of parasitical infections, hypereosinophilic syndrome, eosinophilic pneumonia, eosinophilic enterogastritis, bronchial asthma, atopic dermatitis, allergic rhinitis, urticaria, hypersensitivity pneumonitis, pulmonary aspergillosis, eosinophilic leukemia, hay fever, pollinosis, allergic enterogastritis, food allergy, and drug allergy.

19. A method of preventing or treating an allergic disease comprising administering to a patient in need thereof a therapeutically effective amount of the compound of claim 1 or a pharmaceutically acceptable salt thereof.

20. A method of preventing or treating bronchial asthma comprising administering to a patient in need thereof a therapeutically effective amount of the compound of claim 1 or a pharmaceutically acceptable salt thereof.

21. A method for inhibiting increase of eosinophils in a patient comprising administering to a patient in need thereof a therapeutically effective amount of the compound of claim 1 or a pharmaceutically acceptable salt thereof.

22. A composition for enhancing interferon γ production comprising at least one compound represented by the formula (I) of claim 1 or a pharmaceutically acceptable salt thereof, and a pharmaceutically acceptable carrier.

23. The composition according to claim 22 for oral administration.

24. A composition for enhancing production of interferon γ in an immunocompetent cell comprising at least one compound represented by the formula (I) of claim 1 or a pharmaceutically acceptable salt thereof, and a pharmaceutically acceptable carrier.

25. The composition according to claim 24 for oral administration.

26. A composition for treating tumors comprising at least one compound represented by the formula (I) of claim 1 or a pharmaceutically acceptable salt thereof, and a pharmaceutically acceptable carrier.

27. The composition according to claim 26 for oral administration.

28. A composition which is an antiviral agent comprising at least one compound represented by the formula (I) of claim 1 or a pharmaceutically acceptable salt thereof, and a pharmaceutically acceptable carrier.

29. A method for enhancing interferon γ production in an immunocompetent cell by using at least a compound represented by the formula (I) of claim 1 or a pharmaceutically acceptable salt thereof.

* * * * *